US008026245B2

(12) United States Patent
Janssen et al.

(10) Patent No.: US 8,026,245 B2
(45) Date of Patent: Sep. 27, 2011

(54) HIV REPLICATION INHIBITING PURINE DERIVATIVES

(75) Inventors: Paul Adriaan Jan Janssen, Vosselaar (BE); Frank Xavier Jozef Herwig Arts, legal representative, Beerse (BE); Paulus Joannes Lewi, Turnhout (BE); Marc René de Jonge, Tilburg (NL); Lucien Maria Henricus Koymans, Retie (BE); Frederik Frans Desiré Daeyaert, Beerse (BE); Jan Heeres, Vosselaar (BE); Hendrik Maarten Vinkers, Antwerp (BE); Ruben Gerardus George Leenders, Nijmegen (NL); Dirk Alfons Leo Vandenput, Cuijk (BE)

(73) Assignee: Janssen Pharmaceutica N.V., Beerse (BE)

( * ) Notice: Subject to any disclaimer, the term of this patent is extended or adjusted under 35 U.S.C. 154(b) by 558 days.

(21) Appl. No.: 10/573,364

(22) PCT Filed: Sep. 21, 2004

(86) PCT No.: PCT/EP2004/052262
§ 371 (c)(1),
(2), (4) Date: Mar. 24, 2006

(87) PCT Pub. No.: WO2005/028479
PCT Pub. Date: Mar. 31, 2005

(65) Prior Publication Data
US 2006/0293330 A1 Dec. 28, 2006

(30) Foreign Application Priority Data
Sep. 25, 2003 (EP) .......................... PCT/EP03/50659

(51) Int. Cl.
*C07D 473/16* (2006.01)
*C07D 473/18* (2006.01)
*A61K 31/52* (2006.01)
*A61K 31/522* (2006.01)
*A61P 31/18* (2006.01)
*C07D 473/40* (2006.01)

(52) U.S. Cl. ................ 514/263.37; 514/263.4; 544/276; 544/277; 558/389; 558/401; 558/403; 558/408; 556/417; 564/305

(58) Field of Classification Search ............. 514/263.37, 514/263.4; 544/276, 277
See application file for complete search history.

(56) References Cited

U.S. PATENT DOCUMENTS

| 3,459,731 | A | 8/1969 | Gramera | |
|---|---|---|---|---|
| 6,414,147 | B1 * | 7/2002 | Currie et al. | 544/276 |
| 6,589,950 | B1 * | 7/2003 | Hayler et al. | 514/234.2 |
| 6,897,307 | B2 * | 5/2005 | Ciszewski et al. | 544/277 |
| 2005/0124637 | A1 * | 6/2005 | Cheng et al. | 514/263.2 |

FOREIGN PATENT DOCUMENTS

| EP | 1002795 B1 | 3/2003 |
|---|---|---|
| WO | WO 97/18839 A1 | 5/1997 |
| WO | WO 98/05335 A1 | 2/1998 |
| WO | WO 99/50250 A1 | 10/1999 |
| WO | WO 00/27825 A1 | 5/2000 |
| WO | WO 00/43394 A1 | 7/2000 |
| WO | WO 01/09134 A1 | 2/2001 |
| WO | WO 01/49688 A1 | 7/2001 |
| WO | WO 03/016306 A1 | 2/2003 |
| WO | WO 2006122003 A2 * | 11/2006 |

OTHER PUBLICATIONS

International Search Report, International Application No. PCT/EP2004/052262 filing of International Search Report Mar. 17, 2005.
Greene et al. "*Protective Groups in Organic Synthesis*", $2^{nd}$ edition, Wiley Interscience, 1991.
Koyanogi et al., "Selective Cytotoxicity of Aids Virus Infection Towards HTLV-I-Transformed Cell Lines", *Int. J. Cancer*, 1985, pp. 445-451, vol. 36.
Larock, Richard C., "*Comprehensive Organic Transformations*", $2^{nd}$ edition, Wiley-VCH, 1999, pp. 1983-1985.
Nogradi, M., "Dimethyl-B-Cyclodextrin.", *Drugs of the Future*, 1984, vol. 9, No. 8, pp. 577-578.
"*Protective Groups in Organic Chemistry*", edited by J W F McOmie, 1973, Plenum Press.
Shang, Luis M., "Cyclin-Dependent Kinases as Cellular Targets for Antiviral Drugs", *Journal of Antimicrobial Chemotherapy*, 2002, pp. 779-792, vol. 50.
* cited by examiner

*Primary Examiner* — Mark Berch
(74) *Attorney, Agent, or Firm* — Patton Boggs LLP

(57) ABSTRACT

The present invention relates to the use of a compound of formula (I) for the manufacture of a medicament for the prevention or the treatment of HIV infection wherein the compound of formula (I) is a compound of formula

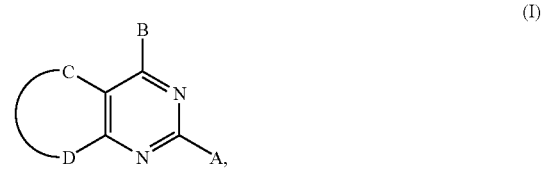

(I)

a N-oxide, a pharmaceutically acceptable addition salt, a quaternary amine or a stereochemically isomeric form thereof, wherein A and B each represents a radical of formula

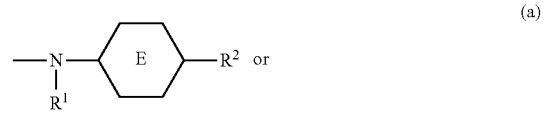

(a)

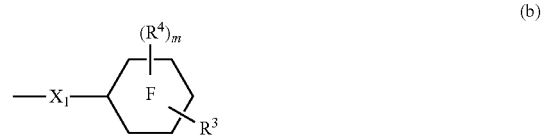

(b)

and wherein —C-D- represents a bivalent radical of formula

—N=CH—NR$^{17}$— (c-1); or

—NR$^{17}$—CH=N— (c-2);

provided that when A represents a radical of formula (a) then B represents a radical of formula (b) and when A represents a radical of formula (b) then B represents a radical of formula (a).

21 Claims, No Drawings

HIV REPLICATION INHIBITING PURINE DERIVATIVES

CROSS REFERENCE TO RELATED APPLICATIONS

This application is the national stage of PCT Application No. PCT/EP2004/052262 (WO2005/028479), filed Sep. 21, 2004, which application claims priority from PCT Patent Application No. PCT/EP03/50659, filed Sep. 25, 2003.

The present invention concerns purine derivatives having HIV (Human Immunodeficiency Virus) replication inhibiting properties. The invention further relates to methods for their preparation and pharmaceutical compositions comprising them.

The invention also relates to the use of said compounds for the manufacture of a medicament for the prevention or the treatment of HIV infection.

WO 98/05335 describes 2,6,9-trisubstituted purine derivatives as inhibitors of cyclin dependent kinase 2 and IκB-α.

WO 01/09134 describes purine derivatives as inhibitors of tyrosine protein kinase SYK.

The compounds of the invention differ from the prior art compounds in structure, pharmacological activity, pharmacological potency.

Unexpectedly, it has been found that the compounds of the invention have an improved ability to inhibit the replication of HIV, including an improved ability to inhibit the replication of mutant strains, i.e. strains which have become resistant to art-known drug(s) (drug or multidrug resistant HIV strains).

The present invention concerns the use of a compound of formula (I) for the manufacture of a medicament for the prevention or the treatment of HIV infection wherein the compound of formula (I) is a compound of formula

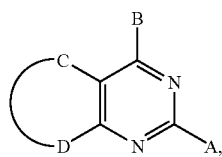

(I)

a N-oxide, a pharmaceutically acceptable addition salt, a quaternary amine or a stereochemically isomeric form thereof, wherein
A and B each represents a radical of formula

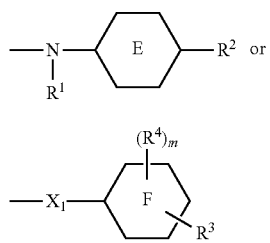

wherein
ring E represents phenyl, pyridyl, pyridazinyl, pyrimidinyl or pyrazinyl;
ring F represents phenyl, pyridyl, pyridazinyl, pyrimidinyl or pyrazinyl;

$R^1$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;

$R^2$ represents cyano; aminocarbonyl; mono- or di($C_{1-4}$alkyl)aminocarbonyl; $C_{1-6}$alkyl optionally substituted with cyano, aminocarbonyl or mono- or di($C_{1-4}$alkyl)aminocarbonyl; $C_{2-6}$alkenyl substituted with cyano, aminocarbonyl or mono- or di($C_{1-4}$alkyl)aminocarbonyl; or $C_{2-6}$alkynyl substituted with cyano, aminocarbonyl or mono- or di($C_{1-4}$alkyl)aminocarbonyl;

$X_1$ represents —$NR^5$—; —NH—NH—; —N=N—; —O—; —C(=O)—; —$C_{1-4}$alkanediyl-; —CHOH—; —S—; —S(=O)$_p$—; —$X_2$—$C_{1-4}$alkanediyl-; —$C_{1-4}$alkanediyl-$X_2$—; or —$C_{1-4}$alkanediyl-$X_2$—$C_{1-4}$alkanediyl-;

$X_2$ represents —$NR^5$—; —NH—NH—; —N=N—; —O—; —C(=O)—; —CHOH—; —S—; or —S(=O)$_p$—;

m represents an integer of value 1, 2, 3 or 4;

$R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from $R^{3a}$; $C_{1-6}$alkyloxy optionally substituted with one or more substituents each independently selected from $R^{3a}$; $C_{1-6}$alkyloxy$C_{1-6}$alkyl optionally substituted with one or more substituents each independently selected from $R^{3a}$; $C_{2-6}$alkenyl optionally substituted with one or more substituents each independently selected from $R^{3a}$; $C_{2-6}$alkynyl optionally substituted with one or more substituents each independently selected from $R^{3a}$; —C(=N—O—$R^8$)—$C_{1-4}$alkyl; $R^7$ or —$X_3$—$R^7$;

$R^{3a}$ represents halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$;

$X_3$ represents —$NR^S$—; —NH—NH—; —N=N—; —O—; —C(=O)—; —S—; —S(=O)$_p$—; —$X_{4a}$—$C_{1-4}$alkanediyl-; —$C_{1-4}$alkanediyl-$X_{4b}$—; —$C_{1-4}$alkanediyl-$X_{4a}$—$C_{1-4}$alkanediyl-; or —C(=N—$OR^8$)—$C_{1-4}$alkanediyl-;

$X_{4a}$ represents —$NR^5$—; —NH—NH—; —N=N—; —C(=O)—; —S—; or —S(=O)$_p$—;

$X_{4b}$ represents —NH—NH—; —N=N—; —O—; —C(=O)—; —S—; or —S(=O)$_p$—;

each $R^4$ independently represents hydroxy; halo; $C_{1-6}$alkyl optionally substituted with one or more substituents each independently selected from $R^{4a}$; $C_{2-6}$alkenyl optionally substituted with one or more substituents each independently selected from $R^{4a}$; $C_{2-6}$alkynyl optionally substituted with one or more substituents each independently selected from $R^{4a}$; $C_{3-7}$cycloalkyl; $C_{1-6}$alkyloxy; $C_{1-6}$alkyloxycarbonyl; $C_{1-6}$alkylcarbonyloxy; carboxyl; formyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; —S(=O)$_p$$R^6$; —NH—S(=O)$_p$$R^6$; —C(=O)$R^6$; —NHC(=O)H; —C(=O)$NHNH_2$; $NHC(=O)R^6$; $C(=NH)R^6$; or $R^7$;

$R^{4a}$ represents halo, cyano, $NR^9R^{10}$, hydroxy or —C(=O)$R^6$;

$R^5$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl or $C_{1-6}$alkylcarbonyloxy; or $C_{1-6}$alkyloxy$C_{1-6}$alkylcarbonyl substituted with $C_{1-6}$alkyloxycarbonyl;

$R^6$ represents $C_{1-6}$alkyl, amino, mono- or di($C_{1-4}$alkyl)amino or polyhalo$C_{1-4}$alkyl;

$R^7$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may, whenever possible, optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$alkanediyl-;

$R^{7a}$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$);

$R^8$ represents hydrogen, $C_{1-4}$alkyl optionally substituted with aryl, or aryl;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(=N$R^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalo$C_{1-4}$alkyl, polyhalo$C_{1-4}$alkyloxy, polyhalo$C_{1-4}$alkylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$, or $R^7$; or $R^9$ and $R^{10}$ may be taken together to form a bivalent or trivalent radical of formula —CH$_2$—CH$_2$—CH$_2$—CH$_2$— (d-1);

—CH$_2$—CH$_2$—CH$_2$—CH$_2$—CH$_2$— (d-2);

—CH$_2$—CH$_2$—O—CH$_2$—CH$_2$— (d-3);

—CH$_2$—CH$_2$—S—CH$_2$—CH$_2$— (d-4);

—CH$_2$—CH$_2$—NR$^{12}$—CH$_2$—CH$_2$— (d-5);

—CH$_2$—CH=CH—CH$_2$— (d-6); or

=CH—CH=CH—CH=CH— (d-7);

$R^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ represents hydrogen or $C_{1-4}$alkyl;

$R^{13}$ and $R^{14}$ each independently represent $C_{1-6}$alkyl optionally substituted with cyano, aminocarbonyl or mono- or di($C_{1-4}$alkyl)aminocarbonyl; $C_{2-6}$alkenyl optionally substituted with cyano, aminocarbonyl or mono- or di($C_{1-4}$alkyl)aminocarbonyl; $C_{2-6}$alkynyl optionally substituted with cyano, aminocarbonyl or mono- or di($C_{1-4}$alkyl)aminocarbonyl;

$R^{15}$ represents $C_{1-6}$alkyl optionally substituted with cyano, aminocarbonyl or mono- or di($C_{1-4}$alkyl)aminocarbonyl;

$R^{16}$ represents $C_{1-6}$alkyl optionally substituted with cyano, aminocarbonyl or mono- or di($C_{1-4}$alkyl)aminocarbonyl; or $R^7$;

—C-D- represents a bivalent radical of formula

—N=CH—NR$^{17}$— (c-1); or

—NR$^{17}$—CH=N— (c-2);

$R^{17}$ represents hydrogen; $C_{1-6}$alkyl optionally substituted with hydroxy, cyano, aminocarbonyl, mono- or di($C_{1-4}$alkyl)aminocarbonyl, $C_{1-4}$alkyloxycarbonyl or aryl;

p represents an integer of value 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$;

provided that when A represents a radical of formula (a) then B represents a radical of formula (b) and when A represents a radical of formula (b) then B represents a radical of formula (a).

The present invention also relates to a compound of formula (I) as defined hereinabove provided that when $R^2$ represents aminocarbonyl or mono- or di($C_{1-4}$alkyl)aminocarbonyl then $R^3$ represents cyano; —C(=O)—$R^{15}$; —CH=N—NH—C(=O)—$R^{16}$; $C_{1-6}$alkyl substituted with one or more substituents each independently selected from $R^{3b}$; $C_{1-6}$alkyloxy substituted with one or more substituents each independently selected from $R^{3a}$; $C_{1-6}$alkyloxy$C_{1-6}$alkyl optionally substituted with one or more substituents each independently selected from $R^{3a}$; $C_{2-6}$alkenyl optionally substituted with one or more substituents each independently selected from $R^{3a}$; $C_{2-6}$alkynyl optionally substituted with one or more substituents each independently selected from $R^{3a}$; —C(=N—O—$R^8$)—$C_{1-4}$alkyl; $R^7$ or —$X_3$—$R^7$; with $R^{3b}$ representing cyano, hydroxy, NR$^9$R$^{10}$, —C(=O)—NR$^9$R$^{10}$, —C(=O)—$C_{1-6}$alkyl, —C(=O)-polyhalo$C_{1-6}$alkyl, —C(=O)—O-polyhalo$C_{1-6}$alkyl or $R^7$.

Thus, the present invention also relates to a compound of formula

(I)

a N-oxide, a pharmaceutically acceptable addition salt, a quaternary amine or a stereochemically isomeric form thereof, wherein
A and B each represents a radical of formula

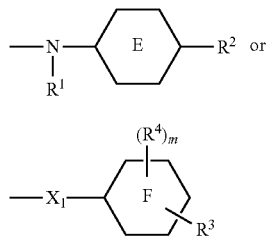

wherein
ring E represents phenyl, pyridyl, pyridazinyl, pyrimidinyl or pyrazinyl;
ring F represents phenyl, pyridyl, pyridazinyl, pyrimidinyl or pyrazinyl;
$R^1$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;
$R^2$ represents cyano; aminocarbonyl; mono- or di($C_{1-4}$alkyl)aminocarbonyl; $C_{1-6}$alkyl optionally substituted with cyano, aminocarbonyl or mono- or di($C_{1-4}$alkyl)aminocarbonyl; $C_{2-6}$alkenyl substituted with cyano, aminocarbonyl or mono- or di($C_{1-4}$alkyl)aminocarbonyl; or $C_{2-6}$alkynyl substituted with cyano, aminocarbonyl or mono- or di($C_{1-4}$alkyl)aminocarbonyl;
$X_1$ represents —$NR^5$—; —NH—NH—; —N=N—; —O—; —C(=O)—; —$C_{1-4}$alkanediyl-; —CHOH—; —S—; —S(=O)$_p$—; —$X_2$—$C_{1-4}$alkanediyl-; —$C_{1-4}$alkanediyl-$X_2$—; or —$C_{1-4}$alkanediyl-$X_2$—$C_{1-4}$alkanediyl-;
$X_2$ represents —$NR^5$—; —NH—NH—; —N=N—; —O—; —C(=O)—; —CHOH—; —S—; or —S(=O)$_p$—;
m represents an integer of value 1, 2, 3 or 4;
$R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from $R^{3a}$; $C_{1-6}$alkyloxy optionally substituted with one or more substituents each independently selected from $R^{3a}$; $C_{1-6}$alkyloxy$C_{1-6}$alkyl optionally substituted with one or more substituents each independently selected from $R^{3a}$; $C_{2-6}$alkenyl optionally substituted with one or more substituents each independently selected from $R^{3a}$; $C_{2-6}$alkynyl optionally substituted with one or more substituents each independently selected from $R^{3a}$; —C(=N—O—$R^8$)—$C_{1-4}$alkyl; $R^7$ or —$X_3$—$R^7$;
$R^{3a}$ represents halo, cyano, hydroxy, $NR^9R^{10}$, —C(=O)—$NR^9R^{10}$, —C(=O)—O—$C_{1-6}$alkyl, —C(=O)-polyhalo$C_{1-6}$alkyl, —C(=O)—O-polyhalo$C_{1-6}$alkyl or $R^7$;
$X_3$ represents —$NR^5$—; —NH—NH—; —N=N—; —O—; —C(=O)—; —S—; —S(=O)$_p$—; —$X_{4a}$—$C_{1-4}$alkanediyl-; —$C_{1-4}$alkanediyl-$X_{4b}$—; —$C_{1-4}$alkanediyl-$X_{4a}$—$C_{1-4}$alkanediyl-; or —C(=N—$OR^8$)—$C_{1-4}$alkanediyl-;
$X_{4a}$ represents —$NR^5$—; —NH—NH—; —N=N—; —C(=O)—; —S—; or —S(=O)$_p$—;
$X_{4b}$ represents —NH—NH—; —N=N—; —O—; —C(=O)—; —S—; or —S(=O)$_p$—;

each $R^4$ independently represents hydroxy; halo; $C_{1-6}$alkyl optionally substituted with one or more substituents each independently selected from $R^{4a}$; $C_{2-6}$alkenyl optionally substituted with one or more substituents each independently selected from $R^{4a}$; $C_{2-6}$alkynyl optionally substituted with one or more substituents each independently selected from $R^{4a}$; $C_{3-7}$cycloalkyl; $C_{1-6}$alkyloxy; $C_{1-6}$alkyloxycarbonyl; $C_{1-6}$alkylcarbonyloxy; carboxyl; formyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; —S(=O)$_p R^6$; —NH—S(=O)$_p R^6$; —C(=O)$R^6$; —NHC(=O)H; —C(=O)$NHNH_2$; NHC(=O)$R^6$; C(=NH)$R^6$; or $R^7$;
$R^{4a}$ represents halo, cyano, $NR^9R^{10}$, hydroxy or —C(=O)$R^6$;
$R^5$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl or $C_{1-6}$alkylcarbonyloxy; or $C_{1-6}$alkyloxy$C_{1-6}$alkylcarbonyl substituted with $C_{1-6}$alkyloxycarbonyl;
$R^6$ represents $C_{1-6}$alkyl, amino, mono- or di($C_{1-4}$alkyl)amino or polyhalo$C_{1-4}$alkyl;
$R^7$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may, whenever possible, optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, cyano, nitro, polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$alkanediyl-;
$R^{7a}$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$);
$R^8$ represents hydrogen, $C_{1-4}$alkyl optionally substituted with aryl, or aryl;
$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(=$NR^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalo$C_{1-4}$alkyl, polyhalo$C_{1-4}$alkyloxy, polyhalo$C_{1-4}$alkylthio, —S(=O)$_p R^6$, —NH—S (=O)$_p$R$^6$, —C(=O)R$^6$, —NHC(=O)H, —C(=O)NHNH$_2$, —NHC(=O)R$^6$, —C(=NH)R$^6$, or R$^7$; or R$^9$ and R$^{10}$ may be taken together to form a bivalent or trivalent radical of formula —CH$_2$—CH$_2$—CH$_2$—CH$_2$— (d-1);

—CH$_2$—CH$_2$—CH$_2$—CH$_2$—CH$_2$— (d-2);

—CH$_2$—CH$_2$—O—CH$_2$—CH$_2$— (d-3);

—CH$_2$—CH$_2$—S—CH$_2$—CH$_2$— (d-4);

—CH$_2$—CH$_2$—NR$^{12}$—CH$_2$—CH$_2$— (d-5);

—CH$_2$—CH=CH—CH$_2$— (d-6); or

=CH—CH=CH—CH=CH— (d-7);

R$^{11}$ represents cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

R$^{12}$ represents hydrogen or C$_{1-4}$alkyl;

R$^{13}$ and R$^{14}$ each independently represent C$_{1-6}$alkyl optionally substituted with cyano, aminocarbonyl or mono- or di(C$_{1-4}$alkyl)aminocarbonyl; C$_{2-6}$alkenyl optionally substituted with cyano, aminocarbonyl or mono- or di(C$_{1-4}$alkyl)aminocarbonyl; C$_{2-6}$alkynyl optionally substituted with cyano, aminocarbonyl or mono- or di(C$_{1-4}$alkyl)aminocarbonyl;

R$^{15}$ represents C$_{1-6}$alkyl optionally substituted with cyano, aminocarbonyl or mono- or di(C$_{1-4}$alkyl)aminocarbonyl;

R$^{16}$ represents C$_{1-6}$alkyl optionally substituted with cyano, aminocarbonyl or mono- or di(C$_{1-4}$alkyl)aminocarbonyl; or R$^7$;

—C-D- represents a bivalent radical of formula

—N=CH—NR$^{17}$— (c-1); or

—NR$^{17}$—CH=N— (c-2);

R$^{17}$ represents hydrogen; C$_{1-6}$alkyl optionally substituted with hydroxy, cyano, aminocarbonyl, mono- or di(C$_{1-4}$alkyl)aminocarbonyl, C$_{1-4}$alkyloxycarbonyl or aryl;

p represents an integer of value 1 or 2;

aryl represents phenyl or phenyl substituted with one, two, three, four or five substituents each independently selected from halo, hydroxy, mercapto, hydroxyC$_{1-6}$alkyl, aminoC$_{1-6}$alkyl, mono or di(C$_{1-6}$alkyl)aminoC$_{1-6}$alkyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, R$^7$ or —X$_3$—R$^7$;

provided that when A represents a radical of formula (a) then B represents a radical of formula (b) and when A represents a radical of formula (b) then B represents a radical of formula (a); and provided that when R$^2$ represents aminocarbonyl or mono- or di(C$_{1-4}$alkyl)aminocarbonyl then R$^3$ represents cyano; —C(=O)—R$^{15}$; —CH=N—NH—C(=O)—R$^{16}$; C$_{1-6}$alkyl substituted with one or more substituents each independently selected from R$^{3b}$; C$_{1-6}$alkyloxy substituted with one or more substituents each independently selected from R$^{3a}$; C$_{1-6}$alkyloxyC$_{1-6}$alkyl optionally substituted with one or more substituents each independently selected from R$^{3a}$; C$_{2-6}$alkenyl optionally substituted with one or more substituents each independently selected from R$^{3a}$; C$_{2-6}$alkynyl optionally substituted with one or more substituents each independently selected from R$^{3a}$; —C(=N—O—R$^8$)—C$_{1-4}$alkyl; R$^7$ or —X$_3$—R$^7$; with R$^{3b}$ representing cyano, hydroxy, NR$^9$R$^{10}$, —C(=O)—NR$^9$R$^{10}$, —C(=O)—C$_{1-6}$alkyl, —C(=O)-polyhaloC$_{1-6}$alkyl, —C(=O)—O-polyhaloC$_{1-6}$alkyl or R$^7$.

As used hereinbefore or hereinafter C$_{1-4}$alkyl as a group or part of a group defines straight or branched chain saturated hydrocarbon radicals having from 1 to 4 carbon atoms such as methyl, ethyl, propyl, 1-methylethyl, butyl; C$_{1-6}$alkyl as a group or part of a group defines straight or branched chain saturated hydrocarbon radicals having from 1 to 6 carbon atoms such as the group defined for C$_{1-4}$alkyl and pentyl, hexyl, 2-methylbutyl and the like; C$_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; C$_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; C$_{3-7}$cycloalkyl is generic to cyclopropyl, cyclobutyl, cyclopentyl, cyclohexyl and cycloheptyl; C$_{2-6}$alkenyl defines straight and branched chain hydrocarbon radicals having from 2 to 6 carbon atoms containing a double bond such as ethenyl, propenyl, butenyl, pentenyl, hexenyl and the like; C$_{2-6}$alkynyl defines straight and branched chain hydrocarbon radicals having from 2 to 6 carbon atoms containing a triple bond such as ethynyl, propynyl, butynyl, pentynyl, hexynyl and the like; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like.

Particular examples of monocyclic, bicyclic or tricyclic partially saturated carbocycles are cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl and the like.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, as mono- or polyhalosubstituted methyl, in particular methyl with one or more fluoro atoms, for example, difluoromethyl or trifluoromethyl; 1,1-difluoro-ethyl and the like. In case more than one halogen atoms are attached to an alkyl group within the definition of polyhalo$C_{1-4}$alkyl or polyhalo$C_{1-6}$alkyl, they may be the same or different.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (e.g. $R^7$, $X_2$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Whenever used hereinbefore or hereinafter that substituents can be selected each independently out of a list of numerous definitions, such as for example for $R^9$ and $R^{10}$, all possible combinations are intended which are chemically possible and which lead to chemically stable molecules.

Some of the compounds of formula (I) may also exist in their tautomeric form. Such forms although not explicitly indicated in the above formula are intended to be included within the scope of the present invention. For instance, the present invention includes the following compounds

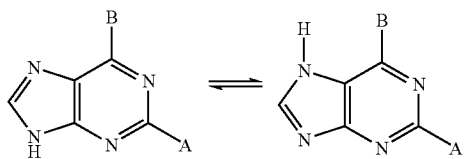

Whenever used hereinafter, the term "compounds of formula (I)" or any subgroup thereof, such as compounds of formula (I-A), (I-A-1), (I-A-2), (I-B), (I-B-1), (I-B-2), (I-C) or (I-D), is meant to also include their N-oxide forms, their salts, their quaternary amines and their stereochemically isomeric forms. Of special interest are those compounds of formula (I) which are stereochemically pure.

A first interesting embodiment of the present invention are those compounds of formula (I) having the following formula

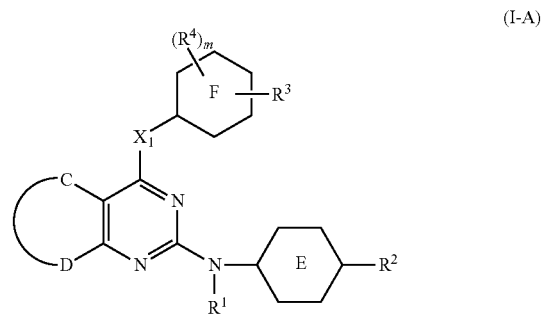

(I-A)

a N-oxide, a pharmaceutically acceptable addition salt, a quaternary amine or a stereochemically isomeric form thereof, wherein $R^1$, $R^2$, $R^3$, $R^4$, ring E, ring F, C, D and m are as defined hereinabove.

A second interesting embodiment of the present invention are those compounds of formula (I-A) having the following formula

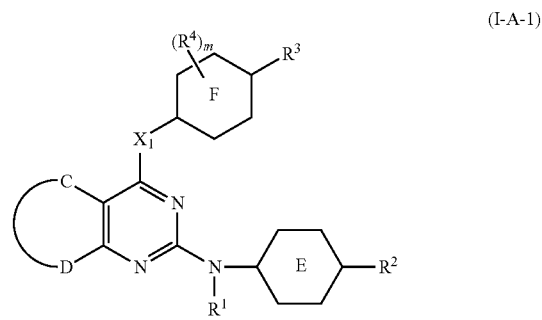

(I-A-1)

a N-oxide, a pharmaceutically acceptable addition salt, a quaternary amine or a stereochemically isomeric form thereof, wherein $R^1$, $R^2$, $R^3$, $R^4$, ring E, ring F, C, D and m are as defined hereinabove.

A third interesting embodiment of the present invention are those compounds of formula (I-A) having the following formula

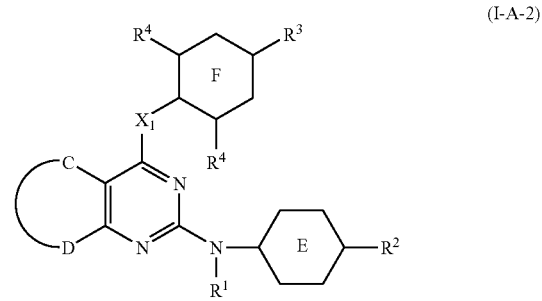

(I-A-2)

a N-oxide, a pharmaceutically acceptable addition salt, a quaternary amine or a stereochemically isomeric form thereof, wherein $R^1$, $R^2$, $R^3$, $R^4$, ring E, ring F, C and D are as defined hereinabove.

A fourth interesting embodiment of the present invention are those compounds of formula (I) having the following formula

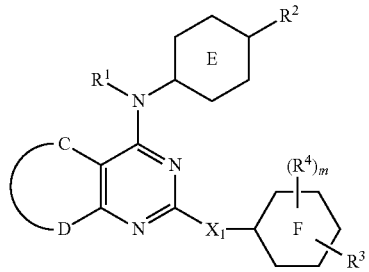

(I-B)

a N-oxide, a pharmaceutically acceptable addition salt, a quaternary amine or a stereochemically isomeric form thereof, wherein $R^1$, $R^2$, $R^3$, $R^4$, ring E, ring F, C, D and m are as defined hereinabove.

A fifth interesting embodiment of the present invention are those compounds of formula (I-B) having the following formula

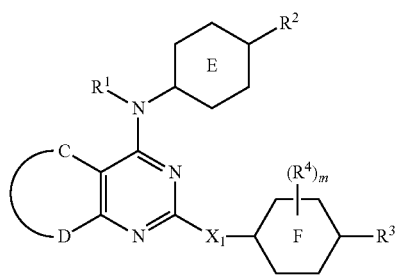

(I-B-1)

a N-oxide, a pharmaceutically acceptable addition salt, a quaternary amine or a stereochemically isomeric form thereof, wherein $R^1$, $R^2$, $R^3$, $R^4$, ring E, ring F, C, D and m are as defined hereinabove.

A sixth interesting embodiment of the present invention are those compounds of formula (I-B) having the following formula

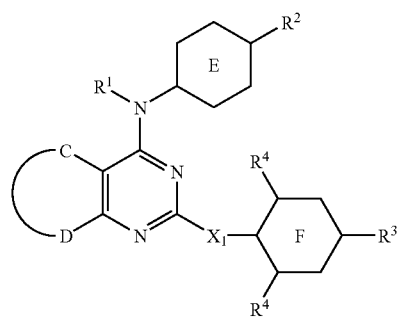

(I-B-2)

a N-oxide, a pharmaceutically acceptable addition salt, a quaternary amine or a stereochemically isomeric form thereof, wherein $R^1$, $R^2$, $R^3$, $R^4$, ring E, ring F, C and D are as defined hereinabove.

A seventh interesting embodiment of the present invention are those compounds of formula (I) having the following formula

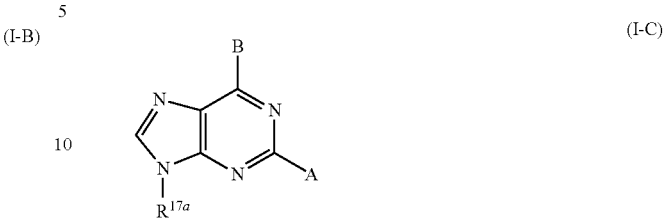

(I-C)

a N-oxide, a pharmaceutically acceptable addition salt, a quaternary amine or a stereochemically isomeric form thereof, wherein A and B are as defined hereinabove and wherein $R^{17a}$ represents $C_{1-6}$alkyl optionally substituted with hydroxy, cyano, aminocarbonyl, mono- or di($C_{1-4}$alkyl)aminocarbonyl, $C_{1-4}$alkyloxycarbonyl or aryl.

An eighth interesting embodiment of the present invention are those compounds of formula (I) having the following formula

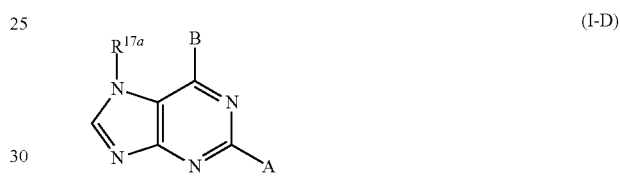

(I-D)

a N-oxide, a pharmaceutically acceptable addition salt, a quaternary amine or a stereochemically isomeric form thereof, wherein A and B are as defined hereinabove and wherein $R^{17a}$ represents $C_{1-6}$alkyl optionally substituted with hydroxy, cyano, aminocarbonyl, mono- or di($C_{1-4}$alkyl)aminocarbonyl, $C_{1-4}$alkyloxycarbonyl or aryl.

A ninth interesting embodiment of the present invention are those compounds of formula (I), (I-A), (I-A-1), (I-A-2), (I-B), (I-B-1), (I-B-2), (I-C) or (I-D) wherein ring E represents phenyl.

A tenth interesting embodiment of the present invention are those compounds of formula (I), (I-A), (I-A-1), (I-A-2), (I-B), (I-B-1), (I-B-2), (I-C) or (I-D) wherein ring F represents phenyl.

A eleventh interesting embodiment of the present invention are those compounds of formula (I), (I-A), (I-A-1), (I-A-2), (I-B), (I-B-1), (I-B-2), (I-C) or (I-D) wherein ring E and ring F represent phenyl.

A twelfth interesting embodiment of the present invention are those compounds of formula (I) or any subgroup thereof as defined hereinabove wherein $R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from $R^{3a}$; $C_{1-6}$alkyloxy optionally substituted with one or more substituents each independently selected from $R^{3a}$; $C_{1-6}$alkyloxy$C_{1-6}$alkyl optionally substituted with one or more substituents each independently selected from $R^{3a}$; $C_{2-6}$alkenyl optionally substituted with one or more substituents each independently selected from $R^{3a}$; $C_{2-6}$alkynyl optionally substituted with one or more substituents each independently selected from $R^{3a}$; or —C(=N—O—$R^8$)—$C_{1-4}$alkyl;

$R^{3a}$ represents halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, or —C(=O)—O-polyhalo$C_{1-6}$alkyl;

each $R^4$ independently represents hydroxy; halo; $C_{1-6}$alkyl optionally substituted with one or more substituents each independently selected from $R^{4a}$; $C_{2-6}$alkenyl optionally substituted with one or more substituents each independently selected from $R^{4a}$; $C_{2-6}$alkynyl optionally substituted with one or more substituents each independently selected from $R^{4a}$; $C_{3-7}$cycloalkyl; $C_{1-6}$alkyloxy; $C_{1-6}$alkyloxycarbonyl; $C_{1-6}$alkylcarbonyloxy; carboxyl; formyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; —S(=O)$_p$R$^6$; —NH—S(=O)$_p$R$^6$; —C(=O)R$^6$; —NHC(=O)H; —C(=O)NHNH$_2$; —NHC(=O)R$^6$; or C(=NH)R$^6$;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(=NR$^{11}$) or R$^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalo$C_{1-4}$alkyl, polyhalo$C_{1-4}$alkyloxy, polyhalo$C_{1-4}$alkylthio, —S(=O)$_p$R$^6$, —NH—S(=O)$_p$R$^6$, —C(=O)R$^6$, —NHC(=O)H, —C(=O)NHNH$_2$, or —NHC(=O)R$^6$, —C(=NH)R$^6$, or $R^9$ and $R^{10}$ may be taken together to form a bivalent or trivalent radical of formula $$—CH_2—CH_2—CH_2—CH_2— \quad (d\text{-}1);$$

$$—CH_2—CH_2—CH_2—CH_2—CH_2— \quad (d\text{-}2);$$

$$—CH_2—CH_2—O—CH_2—CH_2— \quad (d\text{-}3);$$

$$—CH_2—CH_2—S—CH_2—CH_2— \quad (d\text{-}4);$$

$$—CH_2—CH_2—NR^{12}—CH_2—CH_2— \quad (d\text{-}5);$$

$$—CH_2—CH=CH—CH_2— \quad (d\text{-}6); \text{ or}$$

$$=CH—CH=CH—CH=CH— \quad (d\text{-}7);$$

$R^{16}$ represents $C_{1-6}$alkyl optionally substituted with cyano, aminocarbonyl or mono- or di($C_{1-4}$alkyl)aminocarbonyl;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, or aminocarbonyl.

A thirteenth interesting embodiment of the present invention are those compounds of formula (I) or any subgroup thereof as defined hereinabove wherein ring E represents phenyl;
ring F represents phenyl;
$R^1$ represents hydrogen or $C_{1-6}$alkyl;
$R^2$ represents cyano; aminocarbonyl; mono- or di($C_{1-4}$alkyl)aminocarbonyl; $C_{1-6}$alkyl substituted with cyano, aminocarbonyl or mono- or di($C_{1-4}$alkyl)aminocarbonyl; or $C_{2-6}$alkenyl substituted with cyano, aminocarbonyl or mono- or di($C_{1-4}$alkyl)aminocarbonyl; in particular cyano; $C_{1-6}$alkyl substituted with cyano, aminocarbonyl or mono- or di($C_{1-4}$alkyl)aminocarbonyl; or $C_{2-6}$alkenyl substituted with cyano, aminocarbonyl or mono- or di($C_{1-4}$alkyl)aminocarbonyl; more in particular $R^2$ represents cyano or aminocarbonyl; more in particular $R^2$ represents cyano;

$X_1$ represents —NR$^5$—; —O—; —C(=O)—; —$C_{1-4}$alkanediyl-; —CHOH—; —S—; or —S(=O)$_p$—; in particular $X_1$ represents —NR$^5$—; —O— or —S—;

m represents an integer of value 1, 2 or 3; in particular 2;

$R^3$ represents cyano; aminocarbonyl; amino; halo; NHR$^{13}$; NR$^{13}$R$^{14}$; —C(=O)—NHR$^{13}$; —C(=O)—NR$^{13}$R$^{14}$; —C(=O)—R$^{15}$; $C_{1-6}$alkyl optionally substituted with one or more substituents each independently selected from $R^{3a}$; $C_{1-6}$alkyloxy optionally substituted with one or more substituents each independently selected from $R^{3a}$; $C_{1-6}$alkyloxy$C_{1-6}$alkyl optionally substituted with one or more substituents each independently selected from $R^{3a}$; $C_{2-6}$alkenyl optionally substituted with one or more substituents each independently selected from $R^{3a}$; or $C_{2-6}$alkynyl optionally substituted with one or more substituents each independently selected from $R^{3a}$; in particular $R^3$ represents cyano; aminocarbonyl; $C_{1-6}$alkyl optionally substituted with one or more substituents each independently selected from $R^{3a}$; $C_{1-6}$alkyloxy optionally substituted with one or more substituents each independently selected from $R^{3a}$; or $C_{2-6}$alkenyl optionally substituted with one or more substituents each independently selected from $R^{3a}$;

$R^{3a}$ represents halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, or —C(=O)—O-polyhalo$C_{1-6}$alkyl; in particular $R^{3a}$ represents cyano or aminocarbonyl;

each $R^4$ independently represents hydroxy; halo; $C_{1-6}$alkyl optionally substituted with one or more substituents each independently selected from $R^{4a}$; $C_{2-6}$alkenyl optionally substituted with one or more substituents each independently selected from $R^{4a}$; $C_{2-6}$alkynyl optionally substituted with one or more substituents each independently selected from $R^{4a}$; $C_{3-7}$cycloalkyl; $C_{1-6}$alkyloxy; $C_{1-6}$alkyloxycarbonyl; $C_{1-6}$alkylcarbonyloxy; carboxyl; formyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; —S(=O)$_p$R$^6$; —NH—S(=O)$_p$R$^6$; or —C(=O)R$^6$; in particular $R^4$ represents halo; $C_{1-6}$alkyl; $C_{1-6}$alkyloxy; cyano; amino; polyhalo$C_{1-6}$alkyl; or polyhalo$C_{1-6}$alkyloxy;

$R^{4a}$ represents halo, cyano, NR$^9$R$^{10}$, hydroxy or —C(=O)R$^6$;

$R^5$ represents hydrogen or $C_{1-6}$alkyl;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalo$C_{1-4}$alkyl, polyhalo$C_{1-4}$alkyloxy, polyhalo$C_{1-4}$alkylthio, —S(=O)$_p$R$^6$, —NH—S(=O)$_p$R$^6$, or —C(=O)R$^6$; or $R^9$ and $R^{10}$ may be taken together to form a bivalent or trivalent radical of formula $$—CH_2—CH_2—CH_2—CH_2— \quad (d\text{-}1);$$

$$—CH_2—CH_2—CH_2—CH_2—CH_2— \quad (d\text{-}2);$$

$$—CH_2—CH_2—O—CH_2—CH_2— \quad (d\text{-}3);$$

$$—CH_2—CH_2—S—CH_2—CH_2— \quad (d\text{-}4);$$

$$—CH_2—CH_2—NR^{12}—CH_2—CH_2— \quad (d\text{-}5);$$

$$—CH_2—CH=CH—CH_2— \quad (d\text{-}6); \text{ or}$$

$$=CH—CH=CH—CH=CH— \quad (d\text{-}7);$$

in particular $R^9$ and $R^{10}$ each independently represent hydrogen; hydroxy; $C_{1-6}$alkyl or $C_{1-6}$alkyloxy;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, or aminocarbonyl.

A fourteenth interesting embodiment of the present invention are those compounds of formula (I) or any subgroup thereof as defined hereinabove, wherein, whenever the substituents are present, m is 1, 2 or 3; in particular 2.

A fifteenth interesting embodiment of the present invention are those compounds of formula (I) or any subgroup thereof as defined hereinabove, wherein $R^1$ is hydrogen or $C_{1-6}$alkyl; in particular hydrogen.

A sixteenth interesting embodiment of the present invention are those compounds of formula (I) or any subgroup thereof as defined hereinabove wherein $X_1$ represents —$NR^5$—; —O—; —C(=O)—; —$C_{1-4}$alkanediyl-; —CHOH—; —S—; or —S(=O)$_p$—; in particular $X_1$ represents —$NR^5$—; —O—; or —S—; with $R^5$ representing hydrogen or $C_{1-6}$alkyl.

A seventeenth interesting embodiment of the present invention are those compounds of formula or any subgroup thereof as defined hereinabove wherein m is 2 and $R^3$ represents cyano; $C_{1-6}$alkyl optionally substituted with cyano; $C_{1-6}$alkyloxy optionally substituted with cyano; $C_{2-6}$alkenyl substituted with cyano or —C(=O)—$NR^9R^{10}$.

An eighteenth interesting embodiment of the present invention are those compounds of formula (I) as defined above wherein $R^2$ represents cyano; aminocarbonyl; mono- or di($C_{1-4}$alkyl)aminocarbonyl; $C_{1-6}$alkyl substituted with cyano, aminocarbonyl or mono- or di($C_{1-4}$alkyl)aminocarbonyl; $C_{2-6}$alkenyl substituted with cyano, aminocarbonyl or mono- or di($C_{1-4}$alkyl)aminocarbonyl; or $C_{2-6}$alkynyl substituted with cyano, aminocarbonyl or mono- or di($C_{1-4}$alkyl)aminocarbonyl.

A nineteenth interesting embodiment of the present invention are those compounds of formula (I) as defined above wherein $R^2$ represents cyano or aminocarbonyl; in particular cyano.

An twentieth interesting embodiment of the present invention is the use of a compound of formula (I') for the manufacture of a medicament for the prevention or the treatment of HIV infection, wherein the compound of formula (I') is a compound of formula (I')

a N-oxide, a pharmaceutically acceptable addition salt, a quaternary amine or a stereochemically isomeric form thereof, wherein -$a^1$=$a^2$-C($R^2$)=$a^3$-$a^4$=represents a bivalent radical of formula —CH=CH—C($R^2$)=CH—CH=      (a-1);

—N=CH—C($R^2$)=CH—CH=      (a-2);

—CH=N—C($R^2$)=CH—CH=      (a-3);

—N=CH—C($R^2$)=N—CH=      (a-4);

—N=CH—C($R^2$)=CH—N=      (a-5);

—CH=N—C($R^2$)=N—CH=      (a-6); or

—N=N—C($R^2$)=CH—CH=      (a-7);

-$b^1$=$b^2$-$b^3$=$b^4$- represents a bivalent radical of formula

—CH=CH—CH=CH—      (b-1);

—N=CH—CH=CH—      (b-2);

—N=CH—N=CH—      (b-3);

—N=CH—CH=N—      (b-4); or

—N=N—CH=CH—      (b-5);

—C-D- represents a bivalent radical of formula

—N=CH—$NR^{17}$—      (c-1); or

—$NR^{17}$—CH=N—      (c-2);

m represents an integer of value 1, 2, 3 and in case -$b^1$=$b^2$-$b^3$=$b^4$- is (b-1), then m may also be 4;

$R^1$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;

$R^2$ represents cyano; aminocarbonyl; mono- or di($C_{1-4}$alkyl) aminocarbonyl; $C_{1-6}$alkyl optionally substituted with cyano, aminocarbonyl or mono- or di($C_{1-4}$alkyl)aminocarbonyl; $C_{2-6}$alkenyl substituted with cyano, aminocarbonyl or mono- or di($C_{1-4}$alkyl)aminocarbonyl; or $C_{2-6}$alkynyl substituted with cyano, aminocarbonyl or mono- or di($C_{1-4}$alkyl)aminocarbonyl;

$X_1$ represents —$NR^5$—, —NH—NH—, —N=N—, —O—, —C(=O)—, $C_{1-4}$alkanediyl, —CHOH—, —S—, —S(=O)$_p$—, —$X_2$—$C_{1-4}$alkanediyl- or —$C_{1-4}$alkanediyl-$X_2$—;

$X_2$ represents —$NR^5$—, —NH—NH—, —N=N—, —O—, —C(=O)—, —CHOH—, —S—, —S(=O)$_p$—;

$R^3$ represents $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; cyano; halo; $C_{1-6}$alkyl; polyhalo$C_{1-6}$alkyl; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{1-6}$alkyloxy optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl optionally substituted with one or more substituents each independently selected from halo, cyano, $NR^9R^{10}$, —C(=O)—NR$^9$R$^{10}$, —C(=O)—C$_{1-6}$alkyl or R$^7$; C$_{2-6}$alkynyl optionally substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$;

X$_3$ is —NR$^5$—, —NH—NH—, —N=N—, —O—, —C(=O)—, —S—, —S(=O)$_p$—, —X$_{4b}$—C$_{1-4}$alkanediyl-, —C$_{1-4}$alkanediyl-X$_{4a}$—, —C$_{1-4}$alkanediyl-X$_{4b}$—C$_{1-4}$alkanediyl, —C(=N—OR$^8$)—C$_{1-4}$alkanediyl-;

with X$_{4a}$ being —NH—NH—, —N=N—, —O—, —C(=O)—, —S—, —S(=O)$_p$—; and with X$_{4b}$ being —NH—NH—, —N=N—, —C(=O)—, —S—, —S(=O)$_p$—;

each R$^4$ independently represents halo, hydroxy, C$_{1-6}$alkyl, C$_{3-7}$cycloalkyl, C$_{1-6}$alkyloxy, hydroxyC$_{1-6}$alkyl, aminoC$_{1-6}$alkyl, cyano, nitro, polyhaloC$_{1-6}$alkyl, polyhaloC$_{1-6}$alkyloxy, aminocarbonyl, mono- or di(C$_{1-4}$alkyl)aminocarbonyl, C$_{1-6}$alkyloxycarbonyl, C$_{1-6}$alkylcarbonyl, formyl, amino, mono- or di(C$_{1-4}$alkyl)amino or R$^7$;

R$^5$ is hydrogen; aryl; formyl; C$_{1-6}$alkylcarbonyl; C$_{1-6}$alkyloxycarbonyl; C$_{1-6}$alkyl optionally substituted with formyl, C$_{1-6}$alkylcarbonyl, C$_{1-6}$alkyloxycarbonyl or C$_{1-6}$alkylcarbonyloxy; or C$_{1-6}$alkyloxyC$_{1-6}$alkylcarbonyl substituted with C$_{1-6}$alkyloxycarbonyl;

R$^6$ is C$_{1-4}$alkyl, amino, mono- or di(C$_{1-4}$alkyl)amino or polyhaloC$_{1-4}$alkyl;

R$^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted where possible with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ or R$^{7a}$—C$_{1-4}$alkanediyl-;

R$^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted where possible with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, or —CH(=N—O—R$^8$);

R$^8$ is hydrogen, C$_{1-4}$alkyl optionally substituted with aryl, or aryl;

R$^9$ and R$^{10}$ each independently are hydrogen; C$_{1-6}$alkyl; C$_{1-6}$alkylcarbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, hydroxyC$_{1-6}$alkyloxy, carboxyl, C$_{1-6}$alkyloxycarbonyl, cyano, amino, imino, mono- or di(C$_{1-4}$alkyl)amino, polyhaloC$_{1-4}$alkyl, polyhaloC$_{1-4}$alkyloxy, polyhaloC$_{1-4}$alkylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, R$^7$; or R$^9$ and R$^{10}$ may be taken together to form a bivalent or trivalent radical of formula —CH$_2$—CH$_2$—CH$_2$—CH$_2$— (d-1);

—CH$_2$—CH$_2$—CH$_2$—CH$_2$—CH$_2$— (d-2);

—CH$_2$—CH$_2$—O—CH$_2$—CH$_2$— (d-3);

—CH$_2$—CH$_2$—S—CH$_2$—CH$_2$— (d-4);

—CH$_2$—CH$_2$—NR$^{12}$—CH$_2$—CH$_2$— (d-5);

—CH$_2$—CH=CH—CH$_2$— (d-6); or

=CH—CH=CH—CH=CH— (d-7);

R$^{11}$ represents cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

R$^{12}$ represents hydrogen or C$_{1-4}$alkyl;

R$^{13}$ and R$^{14}$ each independently represent C$_{1-6}$alkyl optionally substituted with cyano, aminocarbonyl or mono- or di(C$_{1-4}$alkyl)aminocarbonyl; C$_{2-6}$alkenyl optionally substituted with cyano, aminocarbonyl or mono- or di(C$_{1-4}$alkyl)aminocarbonyl; C$_{2-6}$alkynyl optionally substituted with cyano, aminocarbonyl or mono- or di(C$_{1-4}$alkyl)aminocarbonyl;

R$^{15}$ represents C$_{1-6}$alkyl substituted with cyano, aminocarbonyl or mono- or di(C$_{1-4}$alkyl)aminocarbonyl;

R$^{16}$ represents C$_{1-6}$alkyl optionally substituted with cyano, aminocarbonyl or mono- or di(C$_{1-4}$alkyl)aminocarbonyl; or R$^7$;

R$^{17}$ represents hydrogen; C$_{1-6}$alkyl; or C$_{1-6}$alkyl substituted with aryl;

p is 1 or 2;

aryl represents phenyl or phenyl substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, R$^7$ or —X$_3$—R$^7$.

A twenty first interesting embodiment of the present invention are those compounds of formula (I') as defined hereinabove provided that when R$^2$ represents aminocarbonyl or mono- or di(C$_{1-4}$alkyl)aminocarbonyl then R$^3$ represents —C(=O)—R$^{15}$; —CH=N—NH—C(=O)—R$^{16}$; cyano; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$; C$_{1-6}$alkyl substituted with hydroxy and a second substituent selected from cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from cyano, NR$^9$R$^{10}$, —C(=O)—NR$^9$R$^{10}$, —C(=O)—C$_{1-6}$alkyl or R$^7$; C$_{1-6}$alkyloxy substituted with one or more substituents each independently selected from cyano, NR$^9$R$^{10}$, —C(=O)—NR$^9$R$^{10}$, —C(=O)—C$_{1-6}$alkyl or R$^7$; C$_{2-6}$alkenyl optionally substituted with one or more substituents each independently selected from halo, cyano, NR$^9$R$^{10}$, —C(=O)—C$_{1-6}$alkyl or R$^7$; C$_{2-6}$alkynyl optionally substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$.

A twenty second interesting embodiment of the present invention are those compounds of formula (I) or any subgroup thereof as defined hereinabove wherein $R^3$ is $R^7$, $NR^{13}R^{14}$, —C(=O)$R^{15}$, —CH=N—NH—C(=O)$R^{16}$, —C(=O)NHR$^{13}$, —C(=O)NR$^{13}$R$^{14}$, —C(=N—OR$^8$)—C$_{1-4}$alkyl, C$_{1-6}$alkyl substituted with cyano, C$_{1-6}$alkyl substituted twice with cyano, C$_{1-6}$alkyl substituted with NR$^9$R$^{10}$, C$_{1-6}$alkyl substituted with hydroxy and cyano, C$_{1-6}$alkyl substituted with hydroxy and R$^7$, C$_{1-6}$alkyloxy C$_{1-6}$alkyl, C$_{1-6}$alkyloxy C$_{1-6}$alkyl substituted with cyano, C$_{2-6}$alkenyl substituted with R$^7$, C$_{2-6}$alkenyl substituted with cyano, C$_{2-6}$alkenyl substituted twice with cyano, C$_{2-6}$alkenyl substituted with cyano and R$^7$, C$_{2-6}$alkenyl substituted with cyano and —C(=O)—C$_{1-6}$alkyl, C$_{2-6}$alkenyl substituted with cyano and halo, C$_{2-6}$alkenyl substituted with —C(=O)—NR$^9$R$^{10}$, C$_{2-6}$alkenyl substituted with halo, C$_{2-6}$alkenyl substituted twice with halo or C$_{2-6}$alkenyl substituted with NR$^9$R$^{10}$.

A twenty third interesting embodiment of the present invention are those compounds of formula (I) or any subgroup thereof as defined hereinabove wherein $R^3$ is cyano; aminocarbonyl; C$_{1-6}$alkyl optionally substituted with cyano or aminocarbonyl; C$_{1-6}$alkyloxy optionally substituted with cyano or aminocarbonyl; C$_{2-6}$alkenyl substituted with cyano or aminocarbonyl.

A twenty fourth interesting embodiment of the present invention are those compounds of formula (I) or any subgroup thereof as defined hereinabove wherein $R^3$ represents cyano; C$_{1-6}$alkyl; C$_{1-6}$alkyl substituted with cyano; C$_{1-6}$alkyloxy optionally substituted with cyano; C$_{2-6}$alkenyl substituted with cyano or —C(=O)—NR$^9$R$^{10}$;

A twenty fifth interesting embodiment of the present invention are those compounds of formula (I) or any subgroup thereof as defined hereinabove wherein m is 2 and each $R^4$ independently represents halo, C$_{1-6}$alkyl or C$_{1-6}$alkyloxy.

A twenty sixth interesting embodiment of the present invention are those compounds of formula (I) or any subgroup thereof as defined hereinabove wherein $R^{17}$ represents hydrogen.

A twenty seventh interesting embodiment of the present invention are those compounds of formula (I) as defined hereinabove wherein $R^{17}$ represents C$_{1-6}$alkyl or C$_{1-6}$allyl substituted with hydroxy, cyano or aryl.

A twenty eighth interesting embodiment of the present invention are those compounds of formula (I) or any subgroup thereof as defined hereinabove wherein ring F is 2,4,6-trisubstituted phenyl.

A twenty ninth interesting embodiment of the present invention are those compounds of formula (I) or any subgroup thereof as defined hereinabove wherein the following definitions, apply:
ring E represents phenyl;
ring F represents phenyl;
m is 2;
$R^1$ represents hydrogen;
$R^2$ represents cyano, aminocarbonyl or C$_{1-6}$alkyl, in particular cyano or C$_{1-6}$alkyl; more in particular cyano;
$R^3$ represents cyano; C$_{1-6}$alkyl; C$_{1-6}$alkyl substituted with cyano; C$_{1-6}$alkyloxy optionally substituted with cyano; C$_{2-6}$alkenyl substituted with cyano or —C(=O)—NR$^9$R$^{10}$;
each $R^4$ independently represents halo, C$_{1-6}$alkyl or C$_{1-6}$alkyloxy;
$X_1$ represents —NR$^5$— or —O—;
$R^5$ represents hydrogen;
$R^9$ and $R^{10}$ each independently are hydrogen or C$_{1-6}$alkyl; or $R^9$ and $R^{10}$ may be taken together to form a bivalent radical of formula —CH$_2$—CH$_2$—O—CH$_2$—CH$_2$— (d-3);

$R^{17}$ is hydrogen; C$_{1-6}$alkyl optionally substituted with hydroxy, cyano, aminocarbonyl, C$_{1-4}$alkyloxycarbonyl or aryl;
aryl is phenyl substituted with C$_{1-6}$alkyloxy.

A thirtieth interesting embodiment of the present invention are those compounds of formula (I-A) or (I-B) as defined hereinabove wherein the following definitions, apply:
$R^1$ is hydrogen;
$R^2$ is cyano or aminocarbonyl, in particular cyano;
$R^3$ is C$_{2-6}$alkenyl substituted with cyano; C$_{1-6}$alkyloxy optionally substituted with cyano; cyano; C$_{1-6}$alkyl optionally substituted with cyano;
$R^4$ is C$_{1-6}$alkyl, halo, C$_{1-6}$alkyloxy;
$X_1$ is NH or O;
ring E is phenyl;
ring F is phenyl;
m is 2.

Preferred compounds of formula (I) are compounds 13, 26, 19, 54, 55, 45, 46, 72, 64, 53, 62, 52, 48, 50, 63, 49, 34, 2, 6, 31, 32, 73, 70 and 47, (see Tables 1, 2, 3 and 4), their N-oxides, pharmaceutically acceptable addition salts, quaternary amines and stereochemically isomeric forms thereof.

In general, compounds of formula (I) wherein $R^{17}$ represents C$_{1-6}$alkyl optionally substituted with aryl, said $R^{17}$ being represented by $R^{17b}$, and said compounds being represented by formula (I-a) or (I-b), can be prepared by reacting an intermediate of formula (II-a) or (II-b) wherein $W_1$ represents a suitable leaving group, such as for example halogen, e.g. chloro and the like, with an intermediate of formula (III) in the presence of a suitable catalyst, such as for example Pd(OAc)$_2$, Pd$_2$(dba)$_3$ and the like, a suitable ligand, such as for example a mixture of (+) and (−) 2,2'-bis(diphenylphosphino)-1,1'-binaphthyl, a suitable base, such as for example Cs$_2$CO$_3$ or Na$_3$PO$_4$, and a suitable solvent, such as for example toluene or dioxane.

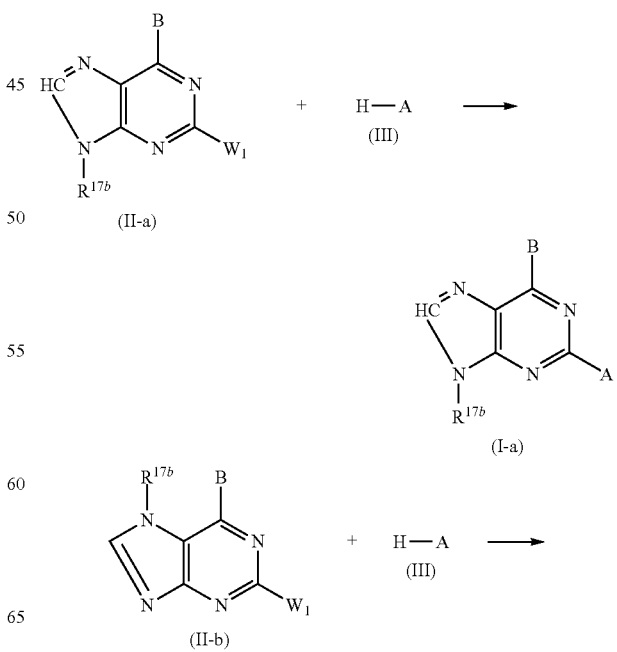

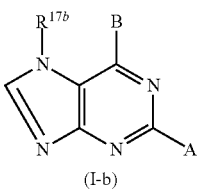

Compounds of formula (I-a) or (I-b) may also be prepared by reacting an intermediate of formula (II'-a) or (II'-b) wherein $W_1$ represents a suitable leaving group, such as for example halogen, e.g. chloro and the like, with an intermediate of formula (III') in the presence of a suitable catalyst, such as for example $Pd(OAc)_2$, $Pd_2(dba)_3$ and the like, a suitable ligand, such as for example a mixture of (+) and (−) 2,2'-bis(diphenylphosphino)-1,1'-binaphthyl, a suitable base, such as for example $Cs_2CO_3$ or $Na_3PO_4$, and a suitable solvent, such as for example toluene or dioxane.

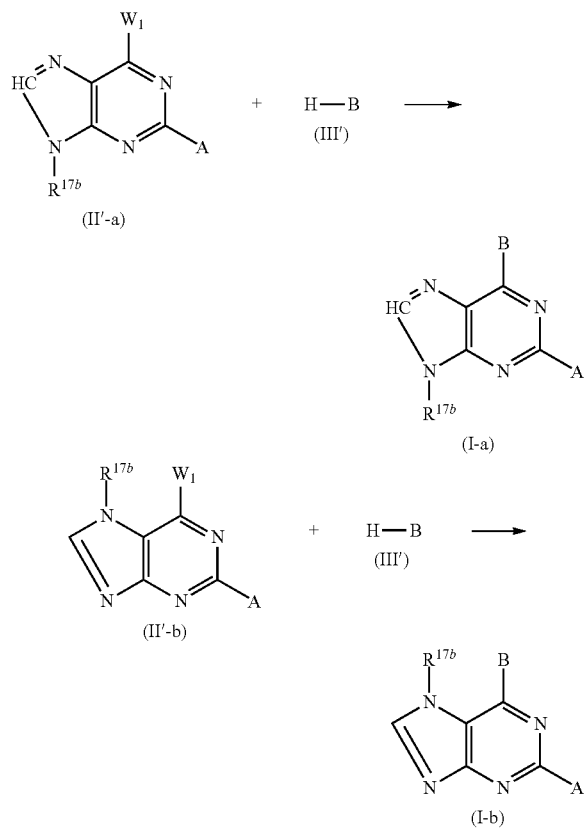

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, a compound of formula (I) wherein $R^3$ comprises cyano, can be converted into a compound of formula (I) wherein $R^3$ comprises aminocarbonyl, by reaction with HCOOH, in the presence of a suitable acid, such as hydrochloric acid. A compound of formula (I) wherein $R^3$ comprises cyano, can also further be converted into a compound of formula (I) wherein $R^3$ comprises tetrazolyl, by reaction with sodium azide in the presence of ammonium chloride and N,N-dimethylacetamide.

Compounds of formula (I) wherein $R^3$ comprises aminocarbonyl, can be converted to a compound of formula (I) wherein $R^3$ comprises cyano, in the presence of a suitable dehydrating agent. The dehydration can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein by reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, TsCl, $P_2O_5$, $(Ph_3PO_3SCF_3)$ $O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, $ClCOCOCl$, $ClCO_2Me$, $Cl_3CCOCl$, $(CF_3CO)_2O$, $Cl_3CN\!=\!\!CCl_2$, 2,4,6-trichloro-1,3,5-triazine, $NaCl.AlCl_3$, $HN(SiMe_2)_3$, $N(SiMe_2)_4$, $LiAlH_4$ and the like. All the reagents listed in said publication are incorporated herein by reference.

Compounds of formula (I) wherein $R^3$ represents optionally substituted $C_{2-6}$alkenyl, can be converted into a compound of formula (I) wherein $R^3$ represents optionally substituted $C_{1-6}$alkyl, by reduction in the presence of a suitable reducing agent, such as for example $H_2$, in the presence of a suitable catalyst, such as for example palladium on charcoal, and in the presence of a suitable solvent, such as for example an alcohol, e.g. methanol.

Compounds of formula (I) wherein $R^3$ represents $CH(OH)$—$R^{16}$, can be converted into a compound of formula (I) wherein $R^3$ represents $C(\!=\!O)$—$R^{16}$ by reaction with Jones's reagent in the presence of a suitable solvent, such as for example 2-propanone.

Compound of formula (I) wherein $R^3$ represents $C(\!=\!O)$—$CH_2$—$R^{16a}$, wherein $R^{16a}$ represents cyano, aminocarbonyl or mono- or di($C_{1-4}$alkyl)aminocarbonyl, can be converted into a compound of formula (I) wherein $R^3$ represents $C(Cl)\!=\!CH$—$R^{16a}$ by reaction with $POCl_3$.

Compounds of formula (I) wherein $R^3$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; each of the ring systems being substituted with formyl can be converted into compounds of formula (I) wherein $R^3$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; each of the ring systems being substituted with CH(=N—O—R$^8$) by reaction with NH$_2$OR$^8$ in the presence of a suitable base, such as for example sodium hydroxide and a suitable solvent, such as for example an alcohol, e.g. ethanol and the like. Compounds of formula (I) wherein R$^3$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; each of the ring systems being substituted with CH(=N—O—R$^8$) can be converted into a compound of formula (I) wherein R$^3$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; each of the ring systems being substituted with CN by reaction with a carbodiimide in the presence of a suitable solvent, such as for example tetrahydrofuran.

Compounds of formula (I) wherein R$^4$ represents nitro, can be converted into a compound of formula (I) wherein R$^4$ is amino, in the presence of a suitable reducing agent, such as for example H$_2$, in the presence of a suitable catalyst, such as for example Raney Nickel, and in the presence of a suitable solvent, such as for example an alcohol, e.g. methanol.

Compounds of formula (I) wherein R$^1$ is hydrogen, can be converted into a compound of formula (I) wherein R$^1$ is C$_{1-6}$alkyl, by reaction with a suitable alkylating agent, such as for example iodo-C$_{1-6}$alkyl, in the presence of a suitable base, such as for example sodium hydride, and a suitable solvent, such as for example tetrahydrofuran.

Compounds of formula (I-a) or (I-b) can be converted into a compound of formula (I) wherein R$^{17}$ represents hydrogen, said compounds being represented by formula (I-c) and (I-d) by reaction with a suitable acid, such as for example trifluoroacetic acid.

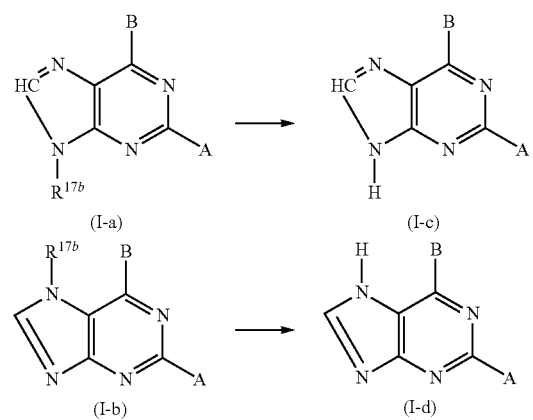

Compounds of formula (I-c) can be converted into a compound of formula (I) wherein R$^{17}$ represents C$_{1-6}$alkyl optionally substituted with cyano or C$_{1-4}$alkyloxycarbonyl, said R$^{17}$ being represented by formula R$^{17c}$ and said compound being represented by formula (I-e), by reaction with an intermediate of formula R$^{17c}$—W$_2$, wherein W$_2$ represents a suitable leaving group, such as for example bromo, iodo and the like, in the presence of a suitable base, such as for example K$_2$CO$_3$, and a suitable solvent, such as for example acetonitrile.

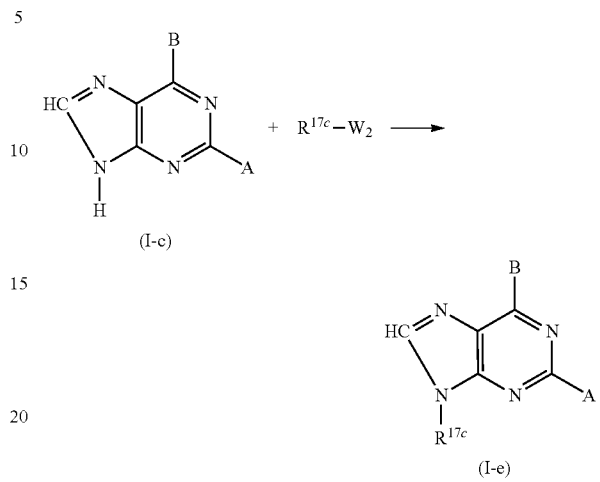

Compounds of formula (I-e) wherein R$^{17c}$ represents C$_{1-6}$alkyl substituted with C$_{1-4}$-alkyloxycarbonyl, said compounds being represented by formula (I-e-1), can be converted into a compound of formula (I) wherein R$^{17}$ represents aminocarbonylC$_{1-6}$alkyl, said compound being represented by formula (I-f), by reaction with NH$_3$ in the presence of a suitable solvent, such as tetrahydrofuran or an alcohol, e.g. methanol. Compounds of formula (I-e-1) can also be converted into a compound of formula (I) wherein R$^{17}$ represents hydroxyC$_{1-6}$alkyl, said compound being represented by formula (I-g), by reaction with NaBH$_4$ in the presence of a suitable solvent, such as for example tetrahydrofuran, an alcohol, e.g. ethanol.

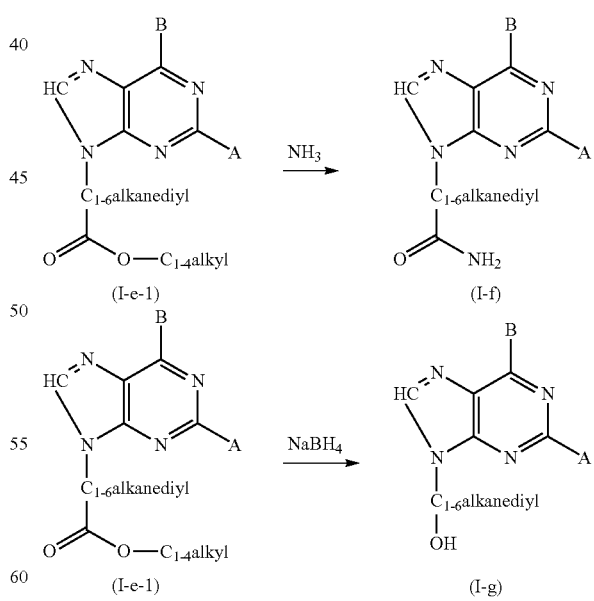

Compounds of formula (I-f) can be converted into a compound of formula (I) wherein R$^{17}$ represents cyanoC$_{1-6}$alkyl, said compound being represented by formula (I-h), by reaction with POCl$_3$ in the presence of a suitable solvent, such as for example tetrahydrofuran.

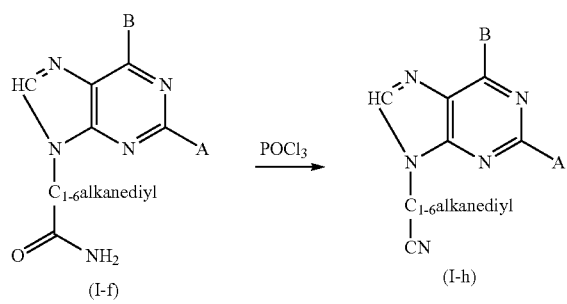

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures or some of the compounds of formula (I) or the described intermediates may be prepared according to the procedures described in WO 99/50250, WO 00/27825 and WO03/016306.

Intermediates of formula (II-a) or (II-b) can be prepared by reacting an intermediate of formula (IV-a) or (IV-b) wherein $W_1$ is as defined above, with an intermediate of formula (III') in the presence of a suitable solvent, such as for example an alcohol, e.g. 2-butanol, a mixture of an alcohol and water, e.g. EtOH and water, or tetrahydrofuran, optionally in the presence of a suitable base, such as for example $K_2CO_3$, K OtertBu, collidine.

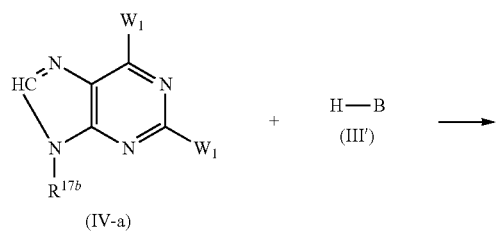

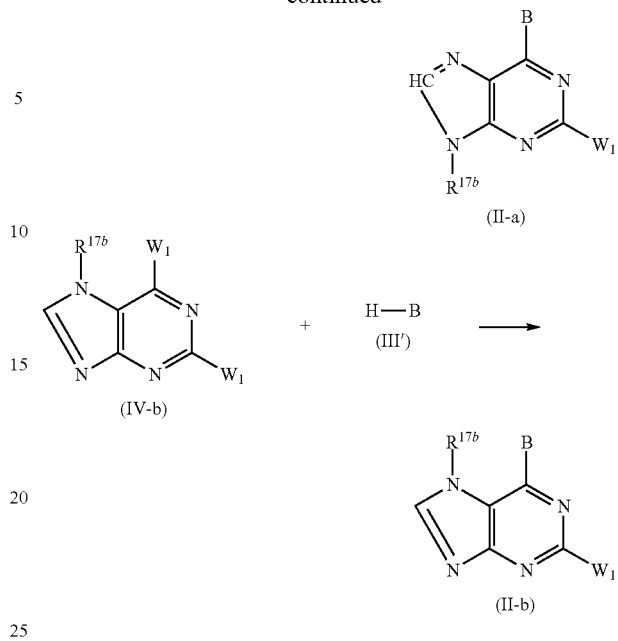

Intermediates of formula (II-a) or (II-b) wherein $R^3$ represents $C_{2-6}$alkenyl substituted with aminocarbonyl, can be converted into an intermediate of formula (II-a) or (II-b) wherein $R^3$ represents $C_{2-6}$alkenyl substituted with cyano, in the presence of $POCl_3$.

Intermediates of formula (II-a) and (II-b) wherein B represents a radical of formula (b) and wherein $X_1$ represents $NR^5$, said intermediates being represented by formula (II-a-1) and (II-b-1), can be prepared by reacting an intermediate of formula (IV-a) or (IV-b) with an intermediate of formula (V) in the presence of a suitable solvent, such as for example tetrahydrofuran, t-amylOH or 1,2-dimethoxy ethane, and a suitable base, such as for example $K_2CO_3$.

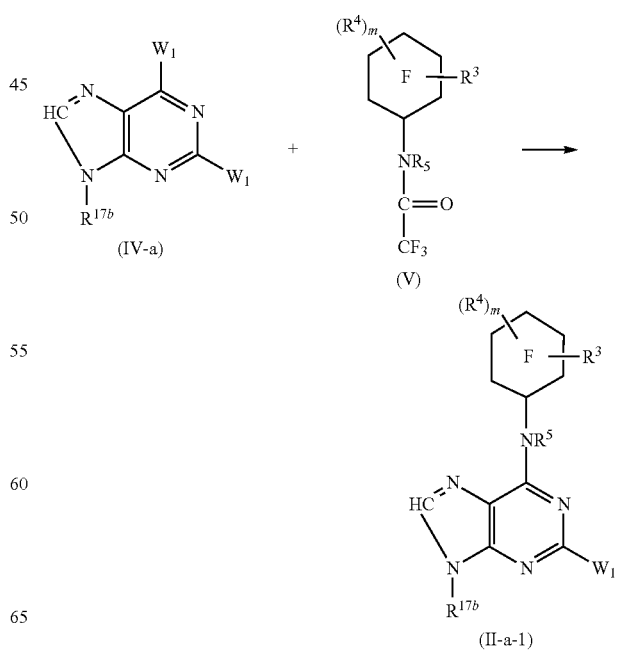

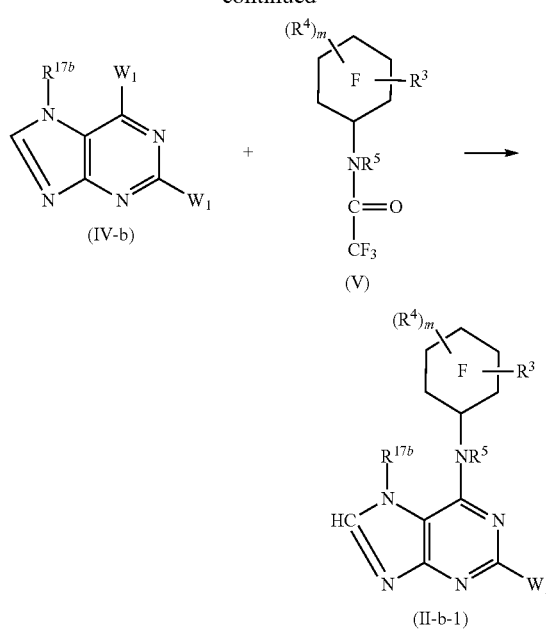

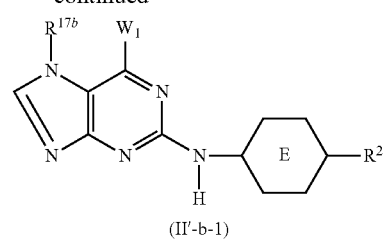

Intermediates of formula (II'-a) and (II'-b) wherein A represents a radical of formula (a) wherein $R^1$ represents hydrogen, said intermediates being represented by formula (II'-a-1) and (II'-b-1), can be prepared by reacting an intermediate of formula (VI-a) or (VI-b) with an intermediate of formula (VI') wherein $W_{1a}$ represents a suitable leaving group, such as for example halogen, e.g. iodo, chloro and the like, in the presence of a suitable catalyst, such as for example Pd(OAc)$_2$, a suitable ligand, such as for example a mixture of (+) and (−) 2,2'-bis(diphenylphosphino)-1,1'-binaphthyl, a suitable base, such as for example Cs$_2$CO$_3$, and a suitable solvent, such as for example toluene or dioxane.

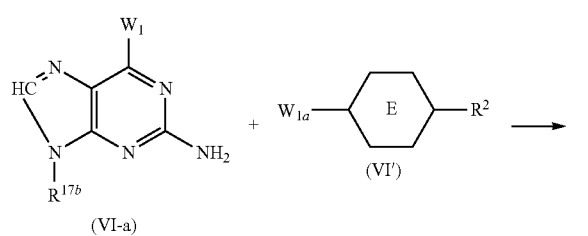

Intermediates of formula (IV-a) and (IV-b) can be prepared by reacting an intermediate of formula (VII) wherein $W_1$ is as defined hereinabove, with an intermediate of formula (VIII) wherein $W_3$ represents a suitable leaving group, such as for example halogen, e.g. chloro, iodo and the like, in the presence of a suitable solvent, such as for example N,N-dimethylformamide or acetonitrile, and a suitable base, such as for example K$_2$CO$_3$.

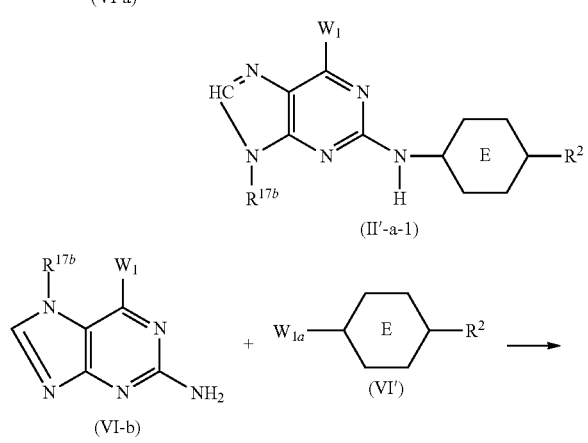

Intermediates of formula (VI-a) and (VI-b) can be prepared by reacting an intermediate of formula (IX) with an intermediate of formula (VIII) in the presence of a suitable solvent, such as for example N,N-dimethylformamide or acetonitrile, and a suitable base, such as for example K$_2$CO$_3$.

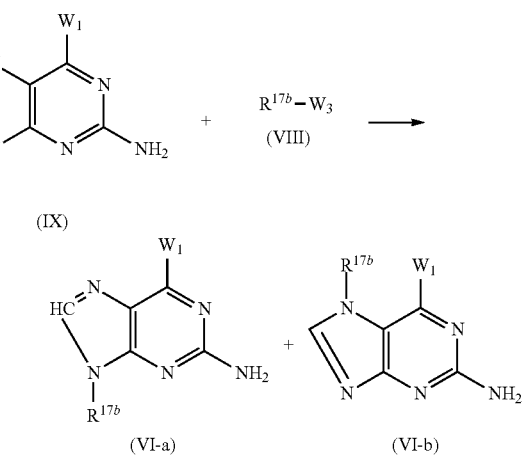

Intermediates of formula (V) can be prepared by reacting an intermediate of formula (X) with trifluoroacetic anhydride in the presence of a suitable solvent, such as for example 1,2-dimethoxy ethane.

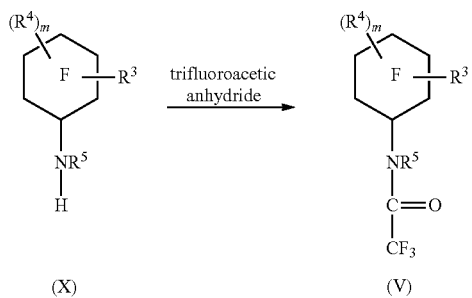

Intermediates of formula (III) or (III') wherein A respectively B represents a radical of formula (b) wherein $R^3$ represents substituted $C_{2-6}$alkenyl, said $R^3$ being represented by $C_{2-6}$alkenyl-$R^{3a}$ and said intermediates being represented by formula by formula (XI), can be prepared by reacting an intermediate of formula (XII) wherein $W_4$ represents a suitable leaving group, such as for example halogen, e.g. bromo and the like, with an intermediate of formula (XIII) in the presence of a suitable catalyst, such as for example $Pd(OAc)_2$, a suitable ligand, such as for example tris(2-methylphenyl)phosphine, a suitable base, such as for example N,N-diethylethanamine, and a suitable solvent, such as for example MeCN.

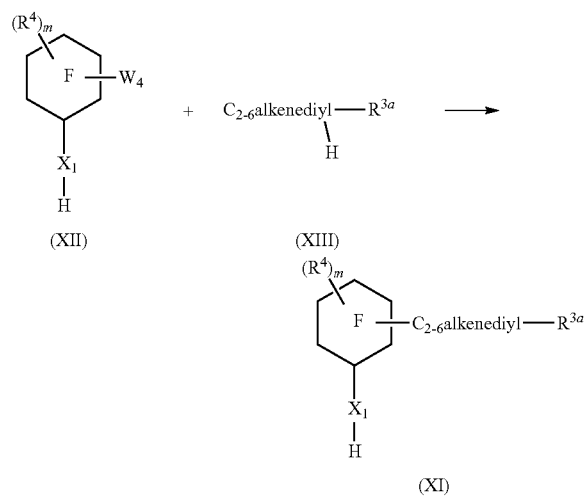

Intermediates of formula (XI) wherein $R^{3a}$ represents —C(=O)—$NH_2$, can be converted into an intermediate of formula (XI) wherein $R^{3a}$ represents CN by reaction with $POCl_3$, optionally in the presence of dichloromethane.

Intermediates of formula (XI) wherein $R^3$ represents $C_{2-6}$alkenyl-CN, can be converted into an intermediate of formula (XI) wherein $R^3$ represents $C_{2-6}$alkyl-CN by reaction with $H_2$, in the presence of a suitable catalyst, such as for example palladium on charcoal, and in the presence of a suitable solvent, such as for example an alcohol, e.g. ethanol.

Intermediates of formula (XI) wherein $R^3$ represents halo, can be converted into an intermediate of formula (XI) wherein $R^3$ represents C(=O)—$CH_3$, by reaction with n-butylvinyl ether, in the presence of a suitable catalyst, such as for example. $Pd(OAc)_2$, a suitable ligand, such as for example 1,3-bis(diphenylphosphino)propane, a suitable base, such as for example $K_2CO_3$, and a suitable solvent, such as for example N,N-dimethylformamide and $H_2O$.

Intermediates of formula (XI) wherein $R^3$ represents C(=O)H respectively C(=O)—$CH_3$, can be converted into an intermediate of formula (XI) wherein $R^3$ represents CH=CH—CN respectively C($CH_3$)=CH—CN, by reaction with cyanomethylphosphonic acid diethylester in the presence of a suitable alcoholate, such as for example sodium methanolate, and a suitable solvent, such as for example an alcohol, e.g. methanol.

Intermediates of formula (XII) wherein $W_4$ represents bromo, said intermediates being represented by formula (XII-a), can be prepared by reacting an intermediate of formula (XIV) with $Br_2$ in the presence of a suitable acid, such as for example acetic acid, and a suitable solvent, such as an alcohol, e.g. methanol.

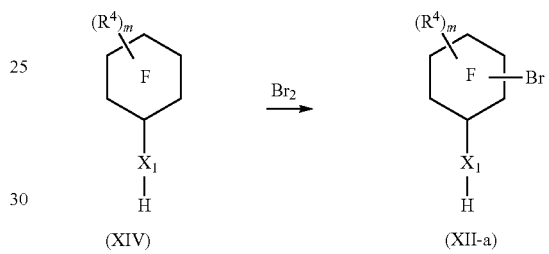

Intermediates of formula (III) or (III') wherein A respectively B represents a radical of formula (b) wherein $X_1$ represents NH, said intermediates being represented by formula (XV), can be prepared by reducing an intermediate of formula (XV') in the presence of a suitable reducing agent, such as for example Fe, in the presence of $NH_4Cl$, and a suitable solvent, such as for example alcohol/water mixture, e.g. MeOH/$H_2O$ (1:2).

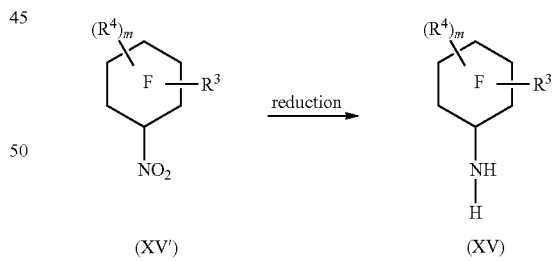

Inter mediates of formula (XV') wherein $R^3$ represents substituted $C_{1-6}$alkyloxy, said $R^3$ being represented by $R^{3a}$—$C_{1-6}$alkyloxy, and said intermediates being represented by formula (XV'-a), can be prepared by reacting an intermediate of formula (XVI) with an intermediate of formula (XVII) wherein $W_5$ represents a suitable leaving group, such as for example halogen, e.g. chloro and the like, in the presence of a suitable base, such as NaI, $K_2CO_3$, and a suitable solvent, such as for example acetone.

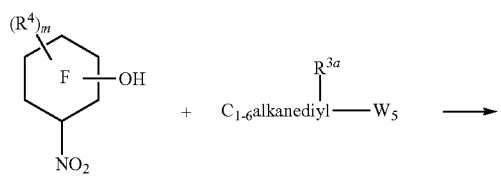

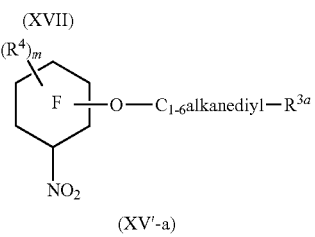

Intermediates of formula (XVI) can be prepared by reacting an intermediate of formula (XVIII) with NaNO$_3$ in the presence of a suitable solvent, such as for example MeSO$_3$H.

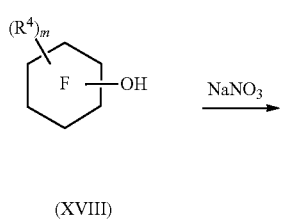

Intermediates of formula (III) or (III') wherein A respectively B represents a radical of formula (b) wherein X$_1$ represents O, said intermediates being represented by formula (XIX), can be prepared by deprotecting an intermediate of formula (XX) wherein P represents a suitable protecting group, such as for example —Si(CH$_3$)$_2$C(CH$_3$)$_3$ or those protecting groups mentioned in Chapter 7 of 'Protective Groups in Organic Synthesis' by T Greene and P. Wuyts (John Wiley & Sons Inc., 1991), in the presence of 4-methylbenzenesulfonic acid and a suitable solvent, such as for example an alcohol, e.g. methanol.

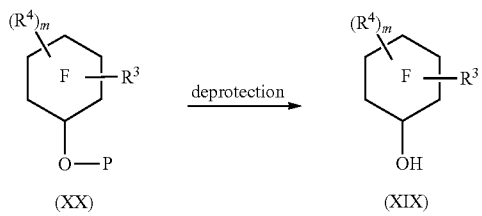

Intermediates of formula (XX) wherein R$^3$ represents CH═CH—CN respectively C(CH$_3$)═CH—CN, said intermediates being represented by formula (XX-a) respectively (XX-b), can be prepared by reacting an intermediate of formula (XXI-a) respectively (XXI-b) with cyanomethylphosphonic acid diethylester in the presence of a suitable alcoholate, such as for example sodium methanolate, and a suitable solvent, such as for example tetrahydrofuran.

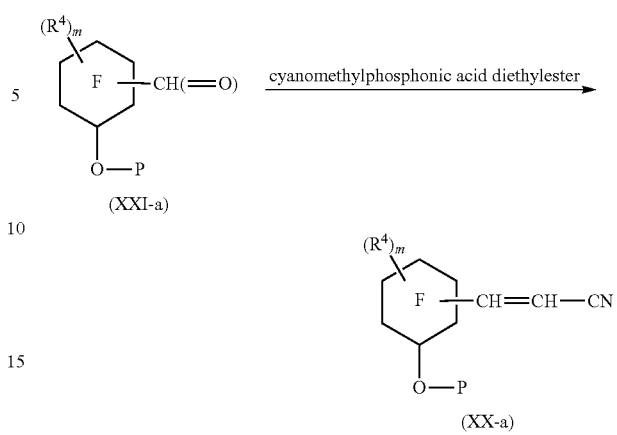

Intermediates of formula (XXI-a) respectively (XXI-b) can be prepared by reacting an intermediate of formula (XXII) with an intermediate of formula (XXIII) wherein W$_6$ represents a suitable leaving group, such as for example halogen, e.g. chloro and the like, and P is as defined hereinabove, in the presence of a suitable solvent, such as for example N,N-dimethylformamide, and a suitable base, such as for example diisopropylethanamine.

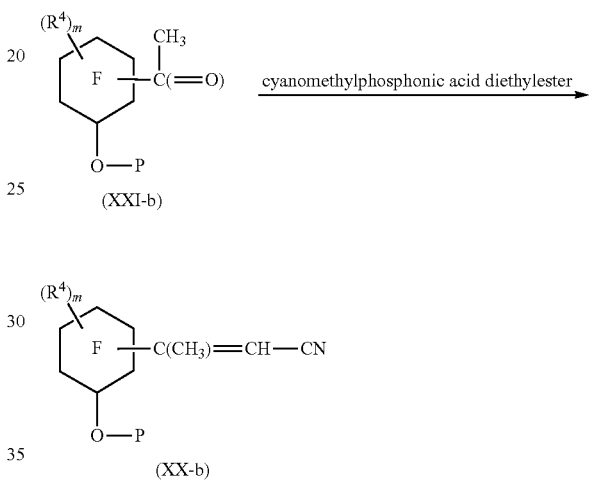

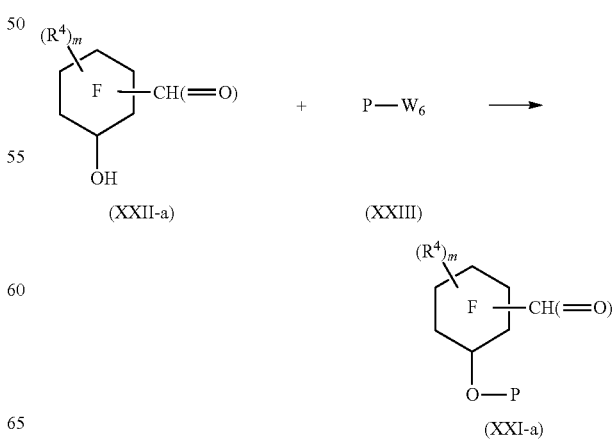

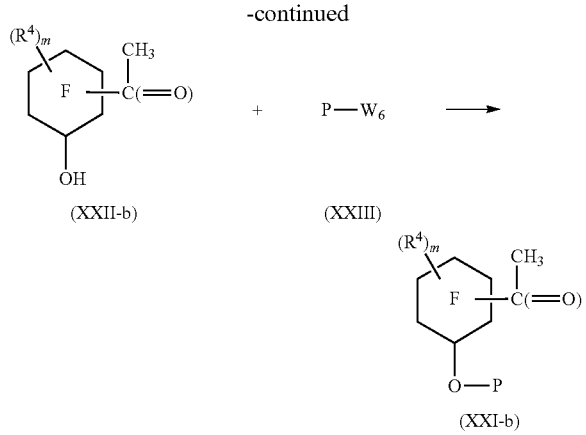

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include ten-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The compounds of formula (I) or any subgroup thereof show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against drug or multidrug resistant HIV strains, in particular drug or multidrug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I) or any subgroup thereof, their N-oxides, pharmaceutically acceptable addition salts, quaternary amines or stereochemically isomeric forms thereof, are useful in the treatment of individuals infected by HIV and for the prophylaxis of these infections. In general, the compounds of the present invention may be useful in the treatment of warm-blooded mammals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) or any subgroup thereof, their N-oxides, pharmaceutically acceptable addition salts, quaternary amines or stereochemically isomeric forms thereof, may be used for the manufacture of a medicament for the treatment or the prevention of HIV infections.

In view of the utility of the compounds of formula (I) or any subgroup thereof, there is provided a method of treating warm-blooded mammals, including humans, suffering from or a method of preventing warm-blooded mammals, including humans, to suffer from viral infections, especially HIV infections. Said method comprises the administration, preferably oral administration, of an effective amount of a compound of formula (I) or any subgroup thereof, a N-oxide form, a pharmaceutically acceptable addition salt, a quaternary amine or a possible stereoisomeric form thereof, to warm-blooded mammals, including humans.

The present invention also provides compositions for treating viral infections comprising a therapeutically effective amount of a compound of formula (I) or any subgroup thereof, a N-oxide, pharmaceutically acceptable addition salt, quaternary amine or stereochemically isomeric form thereof, and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I) or any subgroup thereof, suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) or any subgroup thereof and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) or any subgroup thereof and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I) or any subgroup thereof, or amorphous, microcrystalline or crystalline water-soluble polymer, or both, are dispersed more or less evenly in another phase comprising water-soluble polymer, or compound of formula (I) or any subgroup thereof, or a solid solution comprising compound of formula (I) or any subgroup thereof and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) or any subgroup thereof and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) or any subgroup thereof and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 µm, preferably less than 400 µm and most preferably less than 125 µm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) or any subgroup thereof over the water soluble polymer may vary widely. For example ratios of 1/100 to 100/1 may be applied. Interesting ratios of the compound of formula (I) or any subgroup thereof over cyclodextrin range from about 1/10 to 10/1. More interesting ratios range from about 1/5 to 5/1.

It may further be convenient to formulate the compounds of formula (I) or any subgroup thereof in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) or any subgroup thereof involves a pharmaceutical composition whereby the compounds of formula (I) or any subgroup thereof are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) or any subgroup thereof and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) or any subgroup thereof, used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) or any subgroup thereof can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of an antiretroviral compound and a compound of formula (I) or any subgroup thereof can be used as a medicine. Thus, the present invention also relates to a product containing (a) a compound of formula (I) or any subgroup thereof, and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-dihydro-4-methyl-6H-dipyrido-[3,2-b:2',3'-e][1,4]diazepin-6-one), efavirenz, delavirdine, TMC-120, TMC-125, 4-[[4-[[4-(2-cyanoethenyl)-2,6-dimethylphenyl]-amino]-2-pyrimidinyl]amino] benzonitrile, and the like; phosphonate reverse transcriptase inhibitors, e.g. tenofovir and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl) amino]-2,6-di-chlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) or any subgroup thereof can also be combined with another compound of formula (I) or any subgroup thereof.

Although the present invention focuses on the use of the present compounds for preventing or treating HIV infections, the present compounds may also be used as inhibitory agents for other viruses which depend on similar reverse transcriptases for obligatory events in their life cycle.

The following examples illustrate the present invention.
Experimental Part

Hereinafter, "DMF" is defined as N,N-dimethylformamide, "DME" is defined as 1,2-dimethoxyethane, "THF" is defined as tetrahydrofuran, "BINAP" is defined as a mixture of (+) and (−) [1,1'-binaphthalene]-2,2'-diylbis[diphenylphosphine, "TFA" is defined as trifluoroacetic acid, "TFAA" is defined as trifluoroacetic anhydride, "DCE" is defined as 1,2-dichloro ethane and "DIPEA" is defined as diisopropylethanamine.

A. Preparation of the Intermediate Compounds

EXAMPLE A1 a) Preparation of Intermediate 1

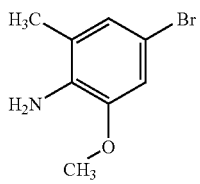

2-Methoxy-6-methylbenzenamine (12.12 g) was dissolved in 100 ml of MeOH and 10 ml of HOAc. Temperature was lowered to 0° C. A solution of 14.12 g $Br_2$ in 50 ml of MeOH was added with careful temperature-control. After addition, the solvents were evaporated and the residue was dissolved in 300 ml of diethyl ether and 100 ml of 2M NaOH. The layers were separated. The ether-layer was dried (NaCl (saturated) and $Na_2SO_4$), filtered and concentrated. Yield: 18.68 g of intermediate 1 (4-bromo-2-methoxy-6-methylbenzenamine) 98%).

b) Preparation of Intermediate 2

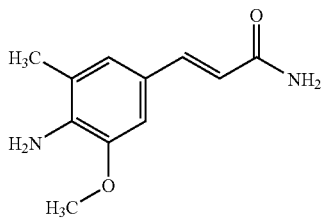

0.1 eq of Pd(OAc)$_2$ (1.23 g), 0.3 eq of tris(2-methylphenyl)phosphine (5.0 g), 1.5 eq of Et$_3$N (8.31 g), 4-bromo-2-methoxy-6-methylbenzenamine (intermediate 1) (11.83 g) and 2-propenamide (1.5 eq., 5.84 g) were brought in 150 ml of MeCN and N$_2$ was bubbled through the suspension for at least 20 minutes. Then a cooler was mounted strictly under nitrogen atmosphere. The reaction was heated at 70° C. overnight. The reaction mixture was allowed to cool to 20° C. and was diluted with 700 ml of CH$_2$Cl$_2$ and washed with saturated aqueous NaHCO$_3$ (2×100 ml) and dried with brine and Na$_2$SO$_4$. The residue was triturated in iPr$_2$O, filtered off and air-dried. Yield: 11.65 g of intermediate 2 (99%).

c) Preparation of Intermediate 3

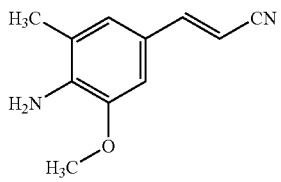

Intermediate 2 (11.65 g) was dissolved in 50 ml of POCl$_3$ at 20° C. The reaction mixture was stirred at 20° C. and checked by TLC. The reaction mixture was added dropwise to 500 ml of diisopropyl ether. The precipitate was filtered off, the residue was added to 350 ml of EtOAc and 250 ml of NaHCO$_3$ (saturated). The layers were separated. The water-layer was washed with 150 ml of EtOAc once. The combined EtOAc-layers were dried (NaCl (saturated) and Na$_2$SO$_4$), filtered and concentrated. Yield: 9.55 g of intermediate 3 (85%).

EXAMPLE A2

Preparation of Intermediate 4

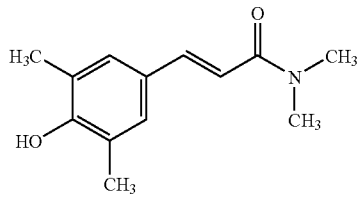

0.1 eq (335 mg) of Pd(OAc)$_2$, 0.2 eq (908 mg) of tris(2-methylphenyl)phosphine, 1.5 eq (3.11 ml) of Et$_3$N, 4-bromo-2,6-dimethylphenol (3.00 g) and N,N-dimethyl-2-propenamide (1.5 eq., 2.31 ml) were brought in 100 ml of MeCN and N$_2$ was bubbled through the suspension for at least 20 minutes. Then a cooler was mounted strictly under nitrogen atmosphere. The reaction was heated at 70° C. overnight. The reaction mixture was allowed to cool to 20° C. and was diluted with 500 ml of CH$_2$Cl$_2$ and washed with saturated aqueous NaHCO$_3$ (2×100 ml) and dried with brine and Na$_2$SO$_4$. The residue was sonicated in iPr$_2$O and filtered off. Yield: 2.26 g of intermediate 4 (69%).

EXAMPLE A3 a) Preparation of Intermediate 6

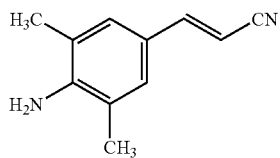

Intermediate 5

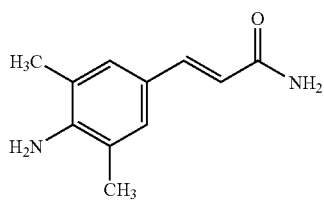

(prepared according to A1b) (6.81 g) was dissolved in 26 ml of POCl$_3$ at 20° C. The reaction mixture was stirred at 20° C. and checked by TLC. The reaction mixture was added dropwise to 500 ml of diisopropyl ether. The precipitate was filtered off, the residue was added to 250 ml of EtOAc and 150 ml of NaHCO$_3$ (saturated) (aqueous). The layers were separated. The water-layer was washed with 100 ml of EtOAc once. The combined EtOAc-layers were dried (NaCl (saturated) and Na$_2$SO$_4$), filtered and concentrated. Yield: 5.37 g of intermediate 6 (87%).

b) Preparation of Intermediate 7

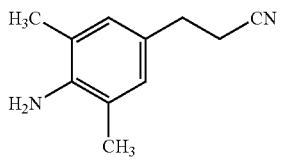

Hydrogenation at P=P$^0$ using 0.05 eq (0.88 g) of 5% Pd/C in 200 ml of EtOH with 1.40 gram of intermediate 6. After 4 hours, the Pd/C was filtered off and the filtrate was evaporated and stripped with 50 ml of EtOAc and with 50 ml of CH$_2$Cl$_2$. Yield: 1.35 g of intermediate 7 (93%).

EXAMPLE A4

Preparation of Intermediate 8

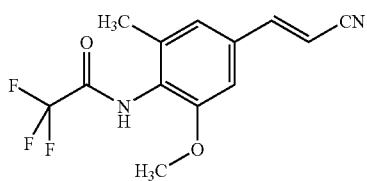

Intermediate 3 (3.81 g) was suspended in 100 ml of 1,2-dimethoxyethane (DME) at 0° C. and stirred vigorously. At 0° C., a solution of TFAA (2.0 eq., 8.48 g) in DME was added dropwise. After vigorously stirring for 30 minutes at 0° C., the reaction mixture was stirred vigorously at 20° C. and checked by TLC. The reaction was quenched by adding 400 ml of NaHCO$_3$ (saturated) (aqueous). EtOAc (200 ml) was added to the quenched reaction mixture. The layers were separated. The water-layer was washed with EtOAc (100 ml) once. The combined EtOAc-layers were dried (NaCl (saturated) and Na$_2$SO$_4$), filtered and concentrated. Yield: 5.77 g of intermediate 8 (98%).

EXAMPLE A5 a) Preparation of Intermediate 9

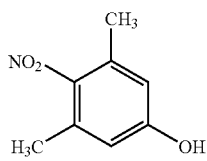

3,5-Dimethylphenol (50 g) was dissolved in 200 ml of MeSO$_3$H and cooled to 0° C. 1 eq (34.8 g) of NaNO$_3$ was added portion-wise at 0° C. After 18 hours, the reaction mixture was poured into 4 liter of ice-H$_2$O under vigorous stirring. The water was decanted. The residue was dissolved in 400 ml of EtOAc. The EtOAc extract was washed with saturated aqueous NaHCO$_3$ (2×200 ml), dried using brine and Na$_2$SO$_4$, and purified using a mixture of EtOAc and n-heptane (4:1) on silica gel. Yield: 7.86 g of intermediate 9 (11%).

b) Preparation of Intermediate 10

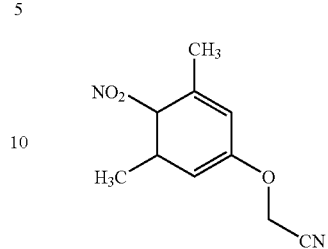

Intermediate 9 (1.40 g) was dissolved in 40 ml of acetone. Subsequently, K$_2$CO$_3$ (2.0 eq., 2.31 g) and NaI (0.1 eq., 126 mg) were added, followed by ClCH$_2$CN (1.5 eq., 0.95 g). After completion of the reaction (GC), the reaction-mixture was filtered and concentrated. The residue was dissolved in 100 ml of EtOAc. The EtOAc extract was washed with saturated aqueous NaHCO$_3$ (2×200 ml), dried using brine and Na$_2$SO$_4$. Yield: 1.91 g of intermediate 10 (99%).

c) Preparation of Intermediate 11

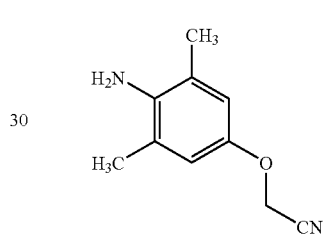

5 eq. (1.30 g) of NH$_4$Cl was dissolved in 20 ml of H$_2$O and 3 eq (0.81 g) of Fe was added. Intermediate 10 (1.00 g) was dissolved in 40 ml of MeOH. The solution was added to the aqueous solution. The reaction was stirred at 50° C. and checked by TLC. The reaction-mixture was filtered hot. The filtrate was poured in 200 ml of EtOAc. The EtOAc extract was washed with saturated aqueous NaHCO$_3$ (2×200 ml), dried using brine and Na$_2$SO$_4$. Yield: 0.92 g of intermediate 11 (100%).

EXAMPLE A6-1 a) Preparation of Intermediate 12

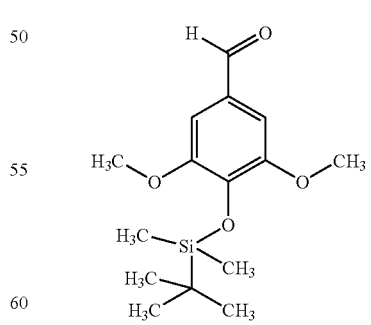

4-Hydroxy-3,5-dimethoxybenzaldehyde (2.00 g) and DIPEA (2.0 eq., 2.84 g) was dissolved in 25 ml of DMF. A solution of chloro(1,1-dimethylethyl)dimethylsilane (1.1 eq., 1.82 g) in 10 ml of DMF was added dropwise. After 18 hours, the reaction mixture was poured into 150 ml of water, followed by extraction with ethyl ether (2×100 ml). The organic layer was dried (NaCl (saturated) and Na₂SO₄), filtered and concentrated. Yield: 2.91 g of intermediate 12 (97%).

b) Preparation of Intermediate 13 and 14

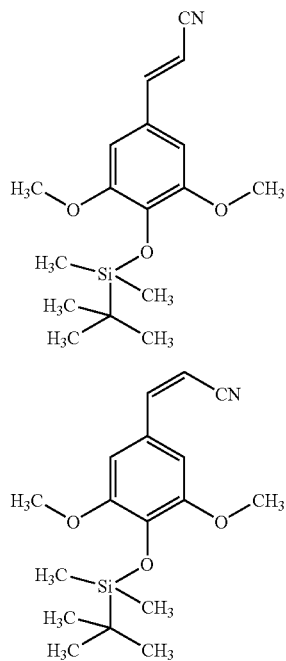

Intermediate 13

Intermediate 14

NaOMe (2.0 eq., 0.73 g) was suspended in 20 ml of THF. A solution of intermediate 12 (2.00 g) in 10 ml of THF was added dropwise. After stirring for 15 minutes, a solution of cyanomethylphosphonic acid diethyl ester (1.0 eq., 1.20 g) was added dropwise. After stirring for 18 hours, the reaction was quenched by adding 0.5 M HCl until the pH was below 1. The quenched reaction mixture was extracted with 150 ml of EtOAc. The layers were separated. The water-layer was washed with 50 ml of EtOAc once. The combined EtOAc-layers were dried (NaCl (saturated) and Na₂SO₄), filtered and concentrated. The residue was dissolved in ethyl ether (50 ml). By adding heptane, the main product from the reaction (the trans-isomer, intermediate 13) precipitated. The mother liquid contained both the cis- and the trans-isomer. Yield: 0.58 g of intermediate 13 (27%).

c) Preparation of Intermediate 15

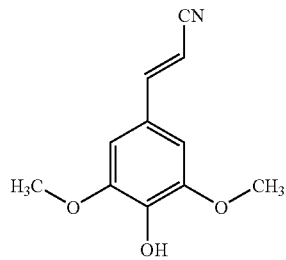

Intermediate 13 (580 mg) was dissolved in 15 ml of MeOH. p-Toluenesulfonic acid (0.05 eq., 20 mg) was added. After 40 hours at 60° C., the deprotection was complete. The reaction-mixture was poured in 50 ml of water and extracted with 150 ml of EtOAc. The layers were separated. The water-layer was washed with 50 ml of EtOAc once. The combined EtOAc-layers were washed with 50 ml of NaHCO₃ (saturated) (aqueous), dried (NaCl (saturated) and Na₂SO₄), filtered and concentrated. Yield: 0.33 g of intermediate 15 (89%).

EXAMPLE A6-2 a) Preparation of Intermediate 41

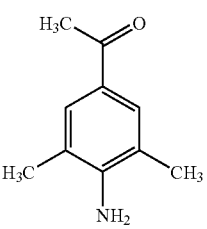

4-Bromo-2,6-dimethylaniline (4.0 gram), n-butyl vinyl ether (3.0 eq., 6.0 gram), K₂CO₃ (1.2 eq., 3.32 gram), Pd(OAc)₂ (0.03 eq., 135 mg) and 1,3-bis(diphenylphosphino)propane (0.66 eq., 0.54 gram) were dissolved in 25 mL of DMF and 3 mL of H₂O and N₂ was bubbled through the suspension for at least 20 minutes. After 24 hours at 80° C., the same amounts of palladium and 1,3-bis(diphenylphosphino)propane were added. Subsequently, the reaction mixture was kept at 80° C. for 16 hours. The reaction mixture was dissolved in 150 ml of Et₂O and 50 ml of 1 N HCl was added. After stirring for 1 hour, the acid aqueous layer was basified with 2 N NaOH. The layers were separated. The water-layer was washed with 50 ml of Et₂O once more. The combined Et₂O-layers were dried (NaCl (saturated) and Na₂SO₄), filtered and concentrated. Yield: 2.72 gr of intermediate 41.

b) Preparation of Intermediate 42 and 43

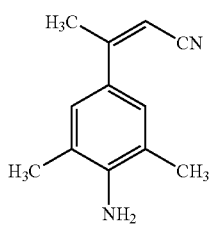

Intermediate 42

(E)

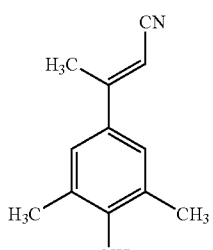

Intermediate 43

NaOMe (3.0 eq., 0.33 g) was dissolved in 20 ml of MeOH. Intermediate 41 (0.33 g) was added in one portion. After stirring for 15 minutes, cyanomethyl phosphonic acid diethyl ester (1.5 eq., 0.53 g) was added dropwise. After stirring for 3 days at 20° C., another portion of cyanomethyl phosphonic acid diethyl ester (1.5 eq., 0.53 g) was added dropwise. After stirring for 4 days at 20° C., another portion of cyanomethylphosphonic acid diethyl ester (1.5 eq., 0.53 g) was added dropwise, followed by NaOMe (1.5 eq., 0.17 g). After total 7 days, the reaction mixture was concentrated. The residue was dissolved in 150 ml of EtOAc and 100 ml of aqueous NaHCO$_3$ (saturated). The layers were separated. The aqueous layer was washed with 50 ml of EtOAc once. The combined EtOAc-layers were dried (NaCl (saturated) and Na$_2$SO$_4$), filtered and concentrated. Separation by flash chromatography using n-heptane/EtOAc 4:1 yielded intermediate 42 and 0.24 g (65%) of intermediate 43 (E).

EXAMPLE A7-1

Preparation of Intermediate 33 and 40

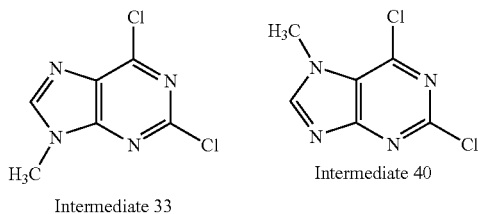

Intermediate 33       Intermediate 40

2,6-dichloropurine (5.0 gram), methyl iodide (1.1 eq., 1.81 mL) and K$_2$CO$_3$ (1.2 eq., 4.39 gram) were dissolved in 200 mL of MeCN. After stirring for 70 hours at 20° C., the MeCN was evaporated. Both isomers were separated by column chromatography using CH$_2$Cl$_2$/MeOH (90/10). Yield: 3.55 g (66%) of intermediate 33 and 1.61 g (30%) of intermediate 40.

EXAMPLE A7-2

Preparation of Intermediate 16 and 17

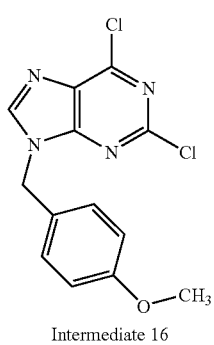

Intermediate 16

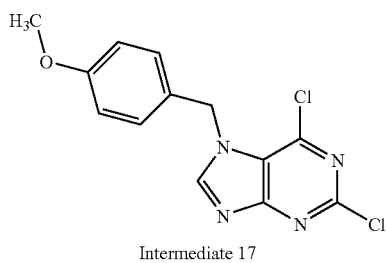

Intermediate 17

2,6-dichloro-1H-purine (18.32 g) and p-methoxybenzylchloride (1.0 eq., 15.72 g) were mixed with K$_2$CO$_3$ (1.0 eq, 15 g) in 100 ml of DMF. The reaction mixture was stirred vigorously and checked by TLC. The solvent was removed and the residue was dissolved in 500 ml of EtOAc and 0.1 M NaOH (100 ml). The layers were separated. The EtOAc-layer was washed with 0.1 M NaOH (2×100 ml), dried (NaCl (saturated) and Na$_2$SO$_4$), filtered and concentrated. The residue was purified by column chromatography using n-heptane/EtOAc (1/1) as the eluent. The first fraction yielded 14.39 g of intermediate 16, the second fraction yielded 8.54 g of intermediate 17.

EXAMPLE A8 a) Preparation of Intermediate 18

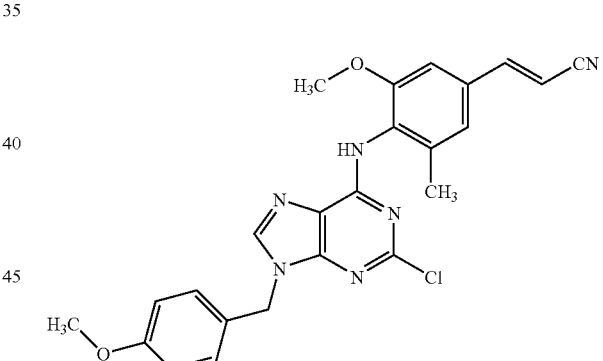

Intermediate 8 (prepared according to A4) (2.32 g) and intermediate 16 (prepared according to A7-2) (1.0 eq., 2.52 g) were mixed with K$_2$CO$_3$ (3.0 eq., 3.38 g) in 50 ml of DME. The reaction mixture was stirred vigorously at 80° C. and checked by TLC and LC/MS. The organic solvents were removed and the residue was dissolved in 300 ml of EtOAc and 100 ml of NaHCO$_3$ (saturated) (aqueous). The layers were separated. The water-layer was washed with 100 ml of EtOAc once, subsequently two times with 150 ml of CH$_2$Cl$_2$. The combined EtOAc-layers were dried (NaCl (saturated) and Na$_2$SO$_4$), filtered and concentrated. The combined CH$_2$Cl$_2$-layers were dried (NaCl (saturated) and Na$_2$SO$_4$), filtered and combined with the residue from the EtOAc-washings. The residue was purified by trituration with 100 ml of ethanol. Yield: 2.69 g of intermediate 18 (72%).

b) Preparation of Intermediate 20

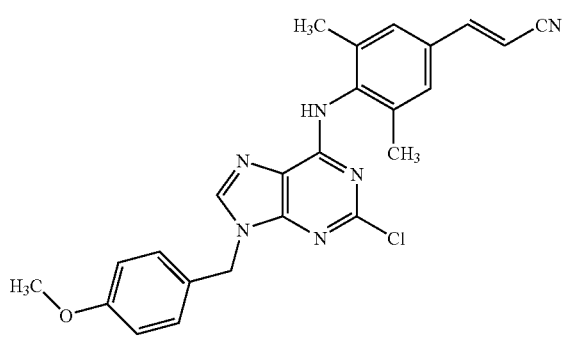

Intermediate 19

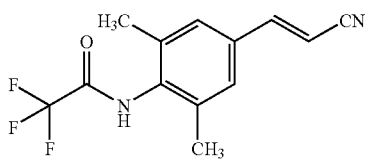

(1.0 eq.; 5.81 g) (prepared according to A4) and intermediate 16 (prepared according to A7) (1.0 eq, 2.52 g)) were mixed with $K_2CO_3$ (3.0 eq; 3.38 g)) in 100 ml of THF. The reaction mixture was stirred vigorously at 80° C. and checked by TLC and LC/MS. The reaction mixture was dissolved in 400 ml of EtOAc and 100 ml of $NaHCO_3$ (saturated) (aqueous). The layers were separated. The water-layer was washed with 100 ml of EtOAc once. The combined EtOAc-layers were dried (NaCl (saturated) and $Na_2SO_4$), filtered and concentrated. The residue was purified by trituration with ethanol. Yield: 0.24 g of intermediate 20 (54%).

c) Preparation of Intermediate 22

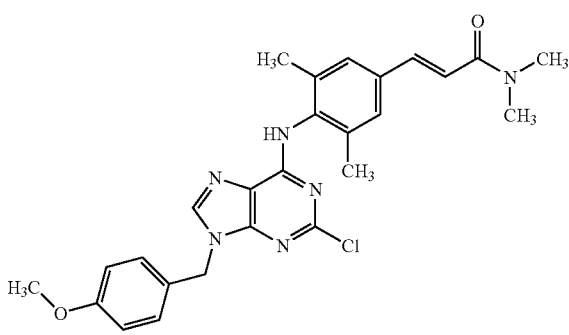

Intermediate 21

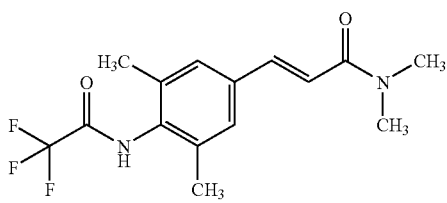

(1.0 eq.; 290 mg) (prepared according to A4) and intermediate 16 (prepared according to A7) (1.0 eq, 2.52 g)) were mixed with $K_2CO_3$ (3.0 eq; 3.38 g)) in 15 ml of t-amyl-OH. The reaction mixture was stirred vigorously at 80° C. and checked by TLC and LC/MS. The organic solvents were removed and the residue was dissolved in 200 ml of EtOAc and 50 ml of $NaHCO_3$ (saturated) (aqueous). The layers were separated. The water-layer was washed with 50 ml of EtOAc once. The combined EtOAc-layers were dried (NaCl (saturated) and $Na_2SO_4$), filtered and concentrated. The residue was purified by preparative TLC using n-heptane/$MeOCH_2CH_2OMe$ (2/3) as the eluent. Yield: 0.10 g of intermediate 22 (20%).

EXAMPLE A9 a) Preparation of Intermediate 23

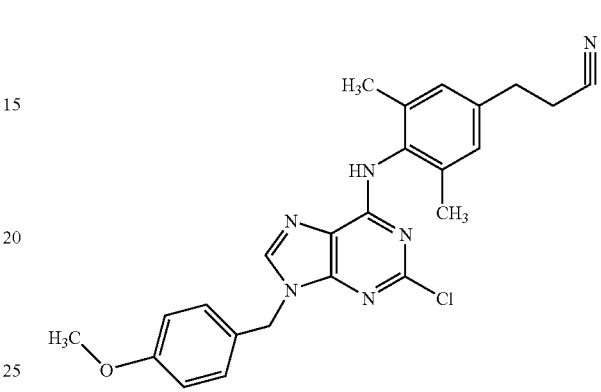

Intermediate 16 (prepared according to A7) (50 mg) and intermediate 7 (prepared according to A3b) (5 eq., 144 mg) were dissolved in EtOH and water (3:1, 4 ml). The reaction mixture was stirred at 80° C. and checked by TLC and LC/MS. The organic solvents were removed and the residue was dissolved in 100 ml of EtOAc and 50 ml of water. The layers were separated. The water-layer was washed with 50 ml of EtOAc once. The combined EtOAc-layers were washed with 1 M HCl (2×50 ml), 50 ml of $NaHCO_3$ (saturated) (aqueous), dried (NaCl (saturated) and $Na_2SO_4$), filtered and concentrated. The residue was purified by preparative TLC using n-heptane/EtOAc (1/1) as the eluent. Yield: 0.04 g of intermediate 23 (49%).

b) Preparation of Intermediate 24

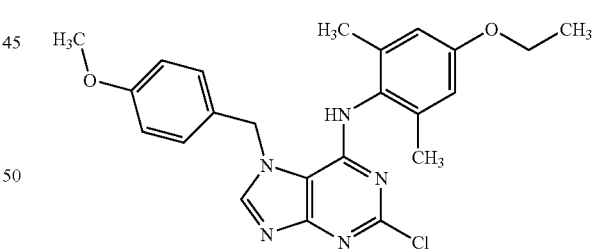

Intermediate 17 (prepared according to A7-2) (150 mg) and 4-ethoxy-2,6-dimethylbenzenamine (5 eq., 241 mg) were dissolved in EtOH and water (3:1, 8 ml). The reaction mixture was stirred at 80° C. and checked by TLC and LC/MS. The organic solvents were removed and the residue was dissolved in 150 ml of EtOAc and 50 ml of water. The layers were separated. The water-layer was washed with 50 ml EtOAc once. The combined EtOAc-layers were washed with 1 M HCl (2×50 ml), 50 ml of $NaHCO_3$ (saturated) (aqueous), dried (NaCl (saturated) and $Na_2SO_4$), filtered and concentrated. The residue was purified by preparative TLC using n-heptane/$MeOCH_2CH_2OMe$ (2/3) as the eluent. Yield: 0.15 g of intermediate 24 (63%).

EXAMPLE A10 a) Preparation of Intermediate 26

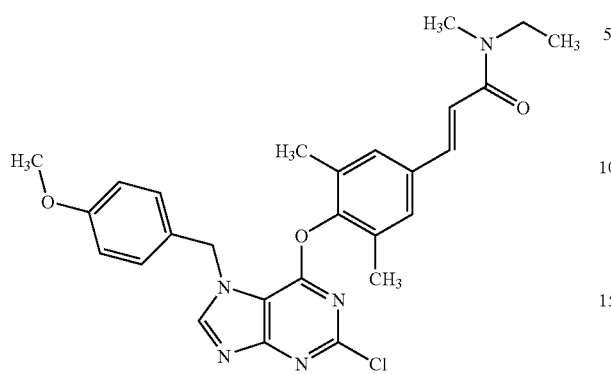

Intermediate 25

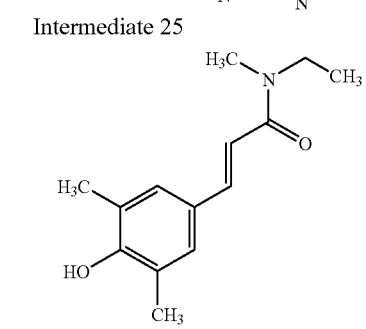

(prepared according to A2) (113 mg) was suspended in 10 ml of THF at 20° C. and stirred KOtBu (1.0 eq., 60 mg) was added at once. After stirring for 30 minutes at 20° C., a solution of intermediate 17 (prepared according to A7-2) (1.0 eq., 150 mg) in 10 ml of THF was added dropwise. The reaction mixture was stirred at 20° C. and checked by TLC and LC/MS. The organic solvents were removed and the residue was dissolved in 15 ml of $CH_2Cl_2$ and 5 ml of $NaHCO_3$ (saturated) (aqueous). The layers were separated. The $CH_2Cl_2$-layer was dried ($Na_2SO_4$), filtered and concentrated. The residue was purified by preparative TLC using n-heptane/$MeOCH_2CH_2OMe$ (2/3) as the eluent. Yield: 0.14 g of intermediate 26 (46%).

b) Preparation of Intermediate 28

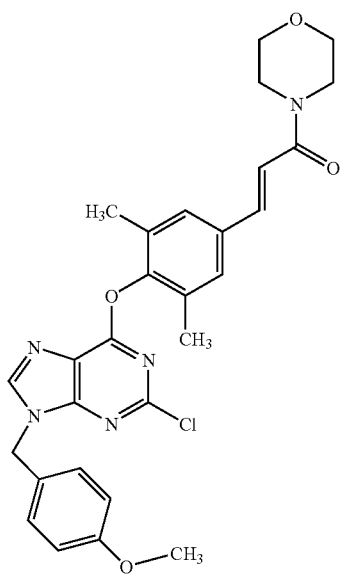

Intermediate 27

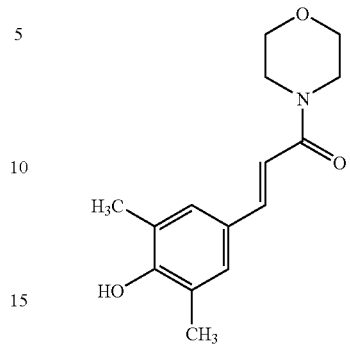

(prepared according to A2) (84.5 mg) was suspended in 10 ml of THF at 20° C. and stirred KOtBu (1.0 eq., 36.3 mg) was added at once. After stirring for 30 minutes at 20° C., a solution of intermediate 16 (prepared according to A7-2) (1.0 eq., 100 mg) in 10 ml of THF was added dropwise. The reaction mixture was stirred at 20° C. and checked by TLC and LC/MS. The reaction-mixture was dissolved in 100 ml of EtOAc and 50 ml of $NaHCO_3$ (saturated) (aqueous). The layers were separated. The water-layer was washed with 50 ml of EtOAc once. The combined EtOAc-layers were dried (NaCl (saturated) and $Na_2SO_4$), filtered and concentrated. The residue was triturated with diisopropyl ether, filtered and air-dried. Yield: 0.17 g of intermediate 28 (96%).

c) Preparation of Intermediate 29

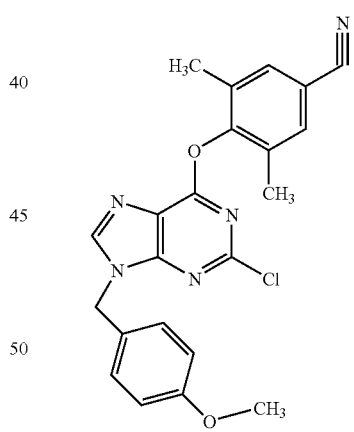

4-Hydroxy-3,5-dimethylbenzonitrile (143 mg) and intermediate 16 (prepared according to A7-2) (1.0 eq., 300 mg) were mixed with $K_2CO_3$ (3.0 eq, 402 mg) in 10 ml of 2-BuOH. The reaction mixture was stirred at 100° C. and checked by TLC and LC/MS. The organic solvents were removed and the residue was dissolved in 100 ml of EtOAc and 50 ml of $NaHCO_3$ (saturated) (aqueous). The layers were separated. The water-layer was washed with 50 ml of EtOAc once. The combined EtOAc-layers were dried (NaCl (saturated) and $Na_2SO_4$), filtered and concentrated. The residue was purified by trituration with 10 ml of ethanol. Yield: 0.26 g of intermediate 29 (64%).

EXAMPLE A11

Preparation of Intermediate 31

Intermediate 30

(100 mg) (prepared according to A10a) was dissolved in 3 ml POCl$_3$ at 20° C. The reaction mixture was stirred at 20° C. and checked by TLC. The reaction mixture was added dropwise to 200 ml of diisopropyl ether. The precipitate was filtered off and was dissolved in 200 ml of EtOAc and 200 ml of NaHCO$_3$ (saturated) (aqueous). The layers were separated. The water-layer was washed with 50 ml of EtOAc once. The combined EtOAc-layers were dried (NaCl (saturated) and Na$_2$SO$_4$), filtered and concentrated. Yield: 0.08 g of intermediate 31 (87%).

EXAMPLE A12

Preparation of Intermediate 32

Intermediate 16 (prepared according to A7-2) (3.09 gram), 4-cyanoaniline (1.3 eq., 1.54 gram) and collidine (2.3 eq., 3.03 ml) were dissolved in EtOH and water (3:1, 150 ml). The reaction mixture was stirred at 85° C. and checked by TLC and LC/MS. After 150 hours, the reaction was cooled to ambient temperature and the solid was filtered off. Yield: 1.84 g of intermediate 32 (47%).

EXAMPLE A13 a. Preparation of Intermediate 34 and 35

Intermediate 34

Intermediate 35

2-Amino-6-chloropurine (5.88 gram), methyl iodide (1.0 eq., 2.39 mL) and K$_2$CO$_3$ (1.0 eq., 4.88 gram) were dissolved in 100 ml of DMF. After stirring for 20 hours at 20° C., the solid material was filtered off and the DMF was evaporated. The residue was used for column chromatography using CH$_2$Cl$_2$/MeOH (95/5). Yield: 2.77 gr (43%) of intermediate 34 and a mix-fraction. This mix-fraction was used for flash chromatography using CH₂Cl₂/MeOH 95/5, slowly raised to 9/1. Yield: 0.39 gram (6%) of intermediate 34 and 0.60 g (9%) of intermediate 35. Total yield of intermediate 34: 3.16 g (49%), total yield of intermediate 35: 0.60 g (9%).

b. Preparation of Intermediate 36

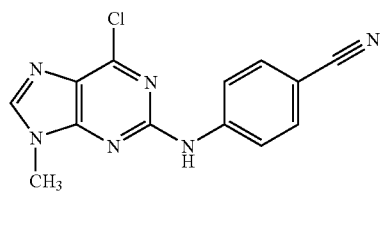

Intermediate 34 (prepared according to A13.a) (370 mg), 4-iodobenzonitrile (1.3 eq, 600 mg), Pd(OAc)₂ (0.15 eq., 68 mg) and BINAP (0.3 eq., 380 mg) were mixed with Cs₂CO₃ (1.4 eq, 920 mg) in 35 ml of dioxane and N₂ was bubbled through the suspension for at least 20 minutes. The reaction mixture was stirred vigorously at 95° C. in a sealed reaction-vessel for 48 hours and checked by TLC and LC/MS. Then the dioxane was evaporated and the residue was purified by column chromatography using CH₂Cl₂/MeOH 99/1. Yield: 151 mg of intermediate 36 (26%).

EXAMPLE A14 a. Preparation of Intermediate 37 and 38

Intermediate 37

Intermediate 38

2-Amino-6-chloropurine (5.47 gram), p-methoxy benzylchloride (1.0 eq., 5.05 gram) and K₂CO₃ (1.1 eq., 4.90 gram) were dissolved in 75 ml of DMF. After stirring for 20 hours at 20° C., the solid material was filtered off and the DMF was evaporated. Both isomers were separated by trituration with EtOAc. Yield: 6.73 gram (72%) of intermediate 37 and 0.48 gram (5%) of intermediate 38.

b. Preparation of Intermediate 39

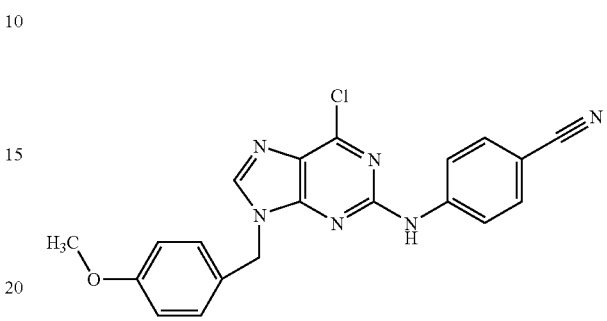

Intermediate 37 (prepared according to A14.a) (1.86 gram), 4-bromobenzonitrile (1.3 eq, 1.52 gram), Pd(OAc)₂ (0.03 eq., 43 mg) and BINAP (0.06 eq., 240 mg) were mixed with Cs₂CO₃ (1.4 eq, 2.93 gram) in 370 ml of toluene and N₂ was bubbled through the suspension for at least 20 minutes. The reaction mixture was stirred vigorously at 80° C. in a sealed reaction-vessel for 80 hours and checked by TLC and LC/MS. Then the toluene was evaporated and the residue was purified by column chromatography using CH₂Cl₂/MeOH (97.5/2.5). Yield: 0.67 gram of intermediate 39 (27%).

B. Preparation of the Final Compounds

EXAMPLE B1 a) Preparation of Compound 1

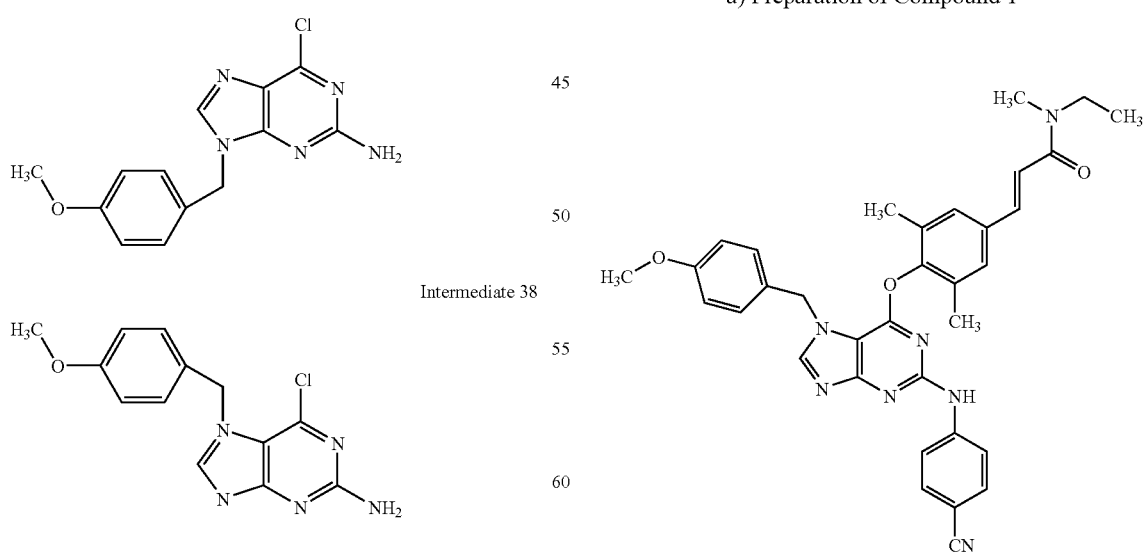

Intermediate 26 (prepared according to A10a) (117 mg), 4-cyanoaniline (1.5 eq., 48 mg), Pd(OAc)₂ (0.06 eq., 6.1 mg) and BINAP (0.12 eq., 34 mg) were mixed with Cs₂CO₃ (1.2 eq, 107 mg) in 20 ml of toluene and N$_2$ was bubbled through the suspension for at least 20 minutes. The reaction mixture was stirred vigorously at 80° C. in a sealed reaction-vessel and checked by TLC and LC/MS. The reaction mixture was dissolved in 150 ml of EtOAc and 50 ml of NaHCO$_3$ (saturated) (aqueous). The layers were separated. The water-layer was washed with 50 ml of EtOAc once. The combined EtOAc-layers were dried (NaCl (saturated) and Na$_2$SO$_4$), filtered and concentrated. The residue was purified by preparative TLC using n-heptane/MeOCH$_2$CH$_2$OMe (2/3) as the eluent. Yield: 0.11 g of compound 1 (82%).

b) Preparation of Compound 2

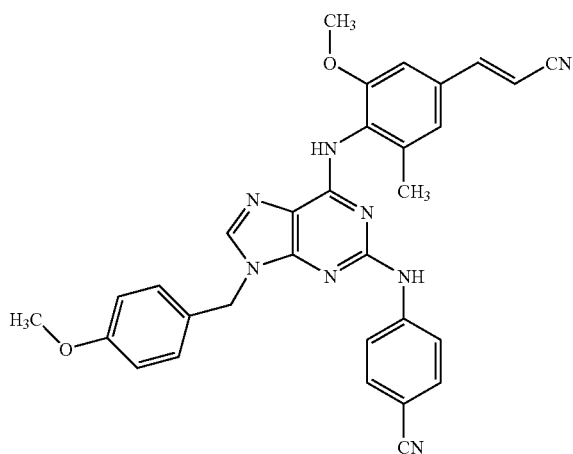

Intermediate 18 (prepared according to A8a) (2.69 g), 4-cyanoaniline (1.5 eq., 1.03 g), Pd(OAc)$_2$ (0.05 eq., 66 mg) and BINAP (0.10 eq., 363 mg) were mixed with Cs$_2$CO$_3$ (1.2 eq, 2.47 g) in 75 ml of toluene and argon was bubbled through the suspension for at least 20 minutes. The reaction mixture was stirred vigorously at 80° C. in a sealed reaction-vessel and checked by TLC and LC/MS. The reaction mixture was filtered off. The residue was washed once with 25 ml of toluene and dissolved in 300 ml of EtOAc and 100 ml of NaHCO$_3$ (saturated) (aqueous). The layers were separated. The EtOAc-layer was dried (Na$_2$SO$_4$), filtered and concentrated. The residue was dissolved in 50 ml of CH$_2$Cl$_2$/MeOH (25:1), followed by addition of 500 ml of diisopropylether. The precipitate was filtered off and air-dried. Yield: 2.05 g of compound 2 (65%).

c) Preparation of Compound 3

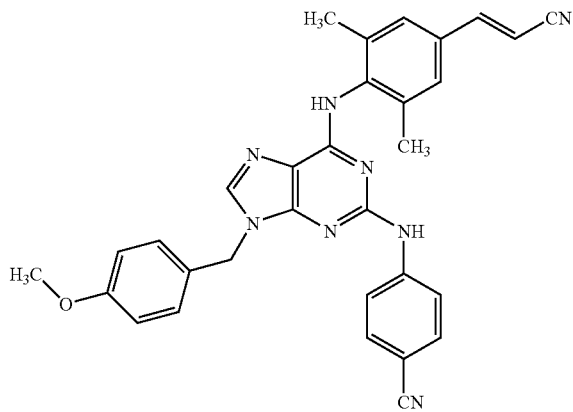

Intermediate 20 (prepared according to A8b) (242 mg), 4-cyanoaniline (1.5 eq.; 96 mg), Pd$_2$(dba)$_3$ (0.03 eq.; 15 mg) and BINAP (0.06 eq.; 20 mg) were mixed with Cs$_2$CO$_3$ (1.2 eq; 212 mg) in 20 ml of toluene and N$_2$ was bubbled through the suspension for at least 20 minutes. The reaction mixture was stirred at 80° C. in a sealed reaction-vessel and checked by TLC and LC/MS. The reaction mixture was dissolved in 150 ml of EtOAc and 50 ml of NaHCO$_3$ (saturated) (aqueous). The layers were separated. The water-layer was washed with 50 ml of EtOAc once. The combined EtOAc-layers were dried (NaCl (saturated) and Na$_2$SO$_4$), filtered and concentrated. The residue was purified by preparative TLC using n-heptane/MeOCH$_2$CH$_2$OMe (2/3) as the eluent. Yield: 0.13 g of compound 3 (46%).

d) Preparation of Compound 4

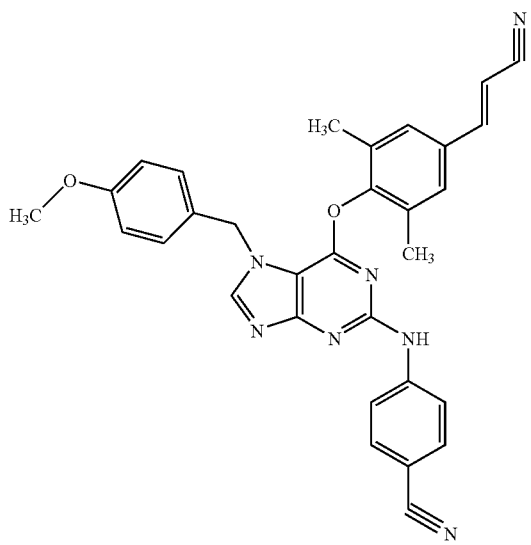

Intermediate 31 (prepared according to A11) (80 mg), 4-cyanoaniline (1.5 eq.; 32 mg), Pd$_2$(dba)$_3$ (0.07 eq.; 12 mg) and BINAP (0.14 eq.; 16 mg) were mixed with Cs$_2$CO$_3$ (1.2 eq.) in 20 ml of toluene and N$_2$ was bubbled through the suspension for at least 20 minutes. The reaction mixture was stirred at 80° C. in a sealed reaction-vessel and checked by TLC and LC/MS. The reaction mixture was dissolved in 150 ml of EtOAc and 50 ml of NaHCO$_3$ (saturated) (aqueous). The layers were separated. The water-layer was washed with 50 ml of EtOAc once. The combined EtOAc-layers were dried (NaCl (saturated) and Na$_2$SO$_4$), filtered and concentrated. The residue was purified by preparative TLC using n-heptane/MeOCH$_2$CH$_2$OMe (2/3) as the eluent. Yield: 0.08 g of compound 4 (84%).

e) Preparation of Compound 73

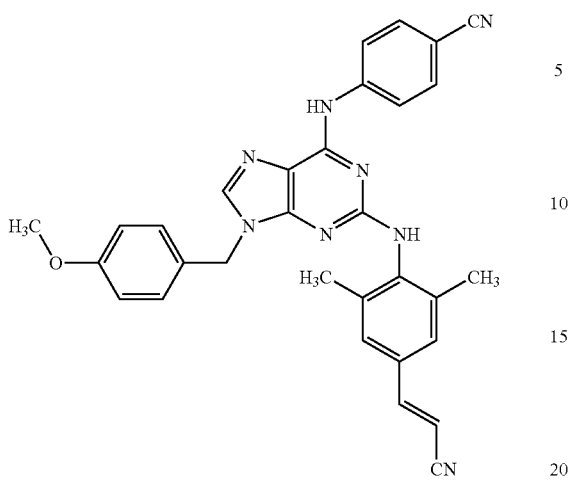

Intermediate 32 (prepared according to A12) (150 mg), intermediate 6 (prepared according to A3.a) (1.5 eq., 99 mg), Pd(OAc)$_2$ (0.07 eq., 6 mg) and BINAP (0.14 eq., 33 mg) were mixed with Cs$_2$CO$_3$ (1.2 eq, 150 mg) in 15 ml of toluene and N$_2$ was bubbled through the suspension for at least 20 minutes. The reaction mixture was stirred vigorously at 80° C. in a sealed reaction-vessel and checked by TLC and LC/MS. The reaction mixture was dissolved in 150 ml of EtOAc and 50 ml of NaHCO$_3$ (saturated) (aqueous). The layers were separated. The water-layer was washed with 50 ml of EtOAc once. The combined EtOAc-layers were dried (NaCl (saturated) and Na$_2$SO$_4$), filtered and concentrated. The residue was purified by preparative TLC using CH$_2$Cl$_2$/MeOH (95/5) as the eluent. Yield: 0.12 g of compound 73 (59%).

f) Preparation of Compound 57

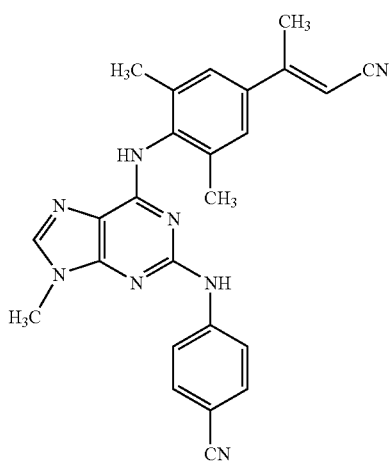

Intermediate 36 (40 mg) (prepared according to A13.b), intermediate 43 (1.3 eq., 34 mg) (prepared according to A6-1.b), Pd(OAc)$_2$ (0.20 eq., 6.3 mg) and BINAP (0.40 eq., 35 mg) were mixed with Cs$_2$CO$_3$ (1.3 eq, 60 mg) in 25 ml of dioxane and argon was bubbled through the suspension for at least 40 minutes. The reaction mixture was stirred vigorously at 95° C. in a sealed reaction-vessel. After 20 hours, the reaction mixture was concentrated. The residue was used for flash chromatography using CH$_2$Cl$_2$/MeOH 99:1. Yield: 23 mg of compound 57 (38%).

EXAMPLE B2 a) Preparation of Compound 5

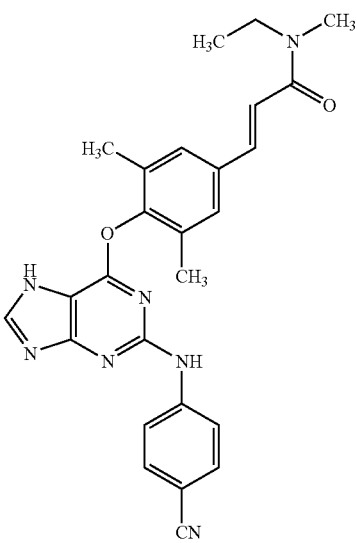

Compound 1 (100 mg) was dissolved in 2 ml of TFA. The reaction mixture was stirred at 40° C. and checked by TLC and LC/MS. The reaction mixture was diluted with 150 ml of CH$_2$Cl$_2$ and added dropwise to a concentrated aqueous solution of K$_2$CO$_3$ (200 ml), checking pH continuously. Extra CH$_2$Cl$_2$ (100 ml) was added to dissolve all material. The layers were separated. The CH$_2$Cl$_2$-layer was dried (NaCl (saturated) and Na$_2$SO$_4$), filtered and concentrated till around 5 ml. The precipitated solid was filtered off and washed once with 5 ml of CH$_2$Cl$_2$. Yield: 0.01 g of compound 5 (15%).

b) Preparation of Compound 6

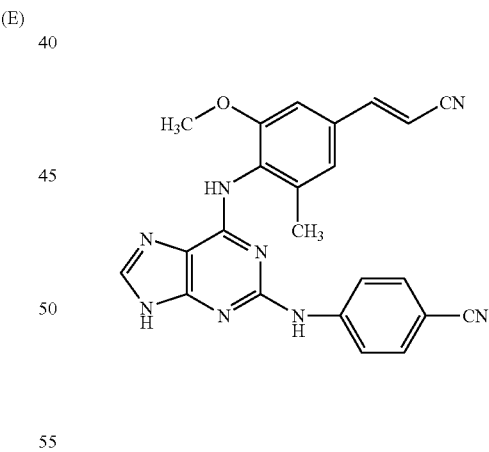

Compound 2 (1.79 g) was dissolved in 8 ml of TFA. The reaction mixture was stirred at 60° C. and checked by TLC and LC/MS. The reaction mixture was added dropwise to a 2M aqueous solution of NaOH (400 ml), checking pH continuously. EtOAc (800 ml) was added to dissolve all material. The layers were separated. The EtOAc-layer was dried (NaCl (saturated) and Na$_2$SO$_4$), filtered and concentrated. The residue was purified by column chromatography using CH$_2$Cl$_2$/MeOH (95/5) as the eluent. The product was isolated by trituation with 500 ml of diisopropylether. The precipitate was filtered off and air-dried. Yield: 0.71 g of compound 6 (51%).

c) Preparation of Compound 70

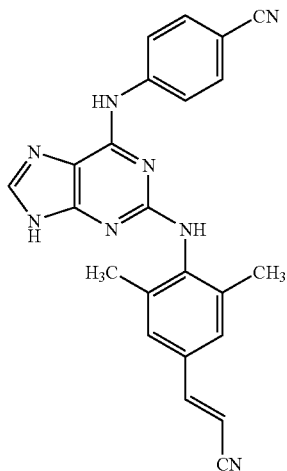

Compound 73 (prepared according to B1.e) (108 mg) was dissolved in 2 ml of TFA. The reaction mixture was stirred at 60° C. and checked by TLC and LC/MS. The reaction mixture was diluted with 150 ml of $CH_2Cl_2$ and added dropwise to a concentrated aqueous solution of $K_2CO_3$ (200 ml), checking pH continuously. Extra $CH_2Cl_2$ (100 ml) was added to dissolve all material. The layers were separated. The $CH_2Cl_2$-layer was dried (NaCl (saturated) and $Na_2SO_4$), filtered and concentrated till around 5 ml and purified by preparative TLC using, $CH_2Cl_2$/MeOH (95/5) as the eluent. Yield: 0.034 g of compound 70 (44%).

EXAMPLE B3 a) Preparation of Compound 49

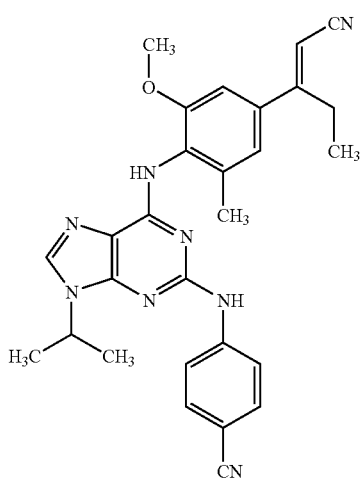

Compound 6 (prepared according to B2.b) (30 mg) was dissolved in 20 ml of MeCN, and isopropyliodide (1.0 eq., 12 mg) and $K_2CO_3$ (3 eq, 29 mg) were added. Stirring for 17 days at 20° C. The MeCN was evaporated and the residue was purified by preparative TLC using $CH_2Cl_2$/MeOH (9/1) as the eluent. Yield: 12 mg of compound 49 (34%).

b) Preparation of Compound 60

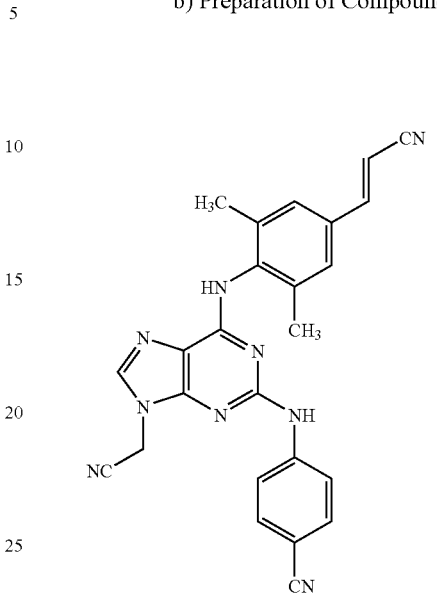

Compound 6 (prepared according to B2.b) (30 mg) was dissolved in 20 ml of MeCN, and iodo acetonitrile (1.0 eq.) and $K_2CO_3$ (3 eq, 29 mg) were added. Stirring for 17 days at 20° C. The MeCN was evaporated and the residue was purified by preparative TLC using $CH_2Cl_2$/MeOH (9/1) as the eluent. Yield: compound 60 (52%).

c) Preparation of Compound 48

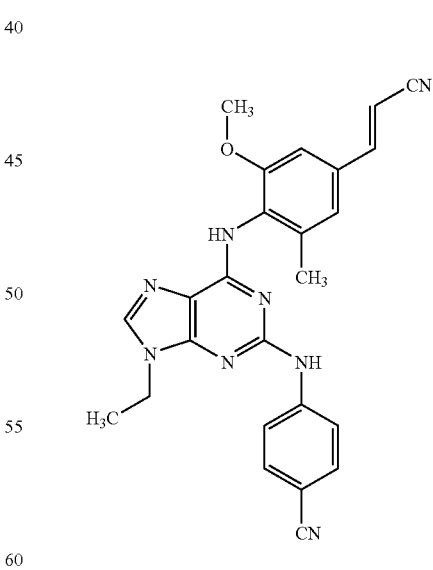

Compound 6 (prepared according to B2.b) (30 mg) was dissolved in 20 ml of MeCN, and ethyl iodide (1.0 eq.) and $K_2CO_3$ (3 eq, 29 mg) were added. Stirring for 17 days at 20° C. The MeCN was evaporated and the residue was purified by preparative TLC using $CH_2Cl_2$/MeOH (9/1) as the eluent. Yield: compound 48 (67%).

EXAMPLE B4 a) Preparation of Compound 75

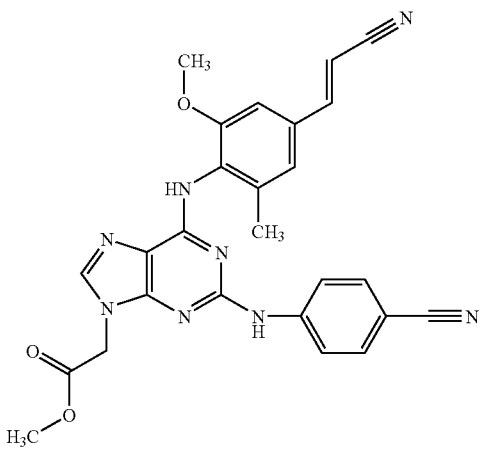

Final compound 6 (prepared according to B2.b) (214 mg) was dissolved in 60 ml of MeCN and 2-bromo methyl acetate (1.0 eq., 48 microliter) and $K_2CO_3$ (3 eq, 210 mg) were added. Stirring for 100 hours at 20° C. The MeCN was evaporated and the residue was purified by Flash chromatography using $CH_2Cl_2$/MeOH: 99/1 to 96/4 as the gradient eluent. Yield: 139 mg of compound 75 (56%).

b. Preparation of Compound 50

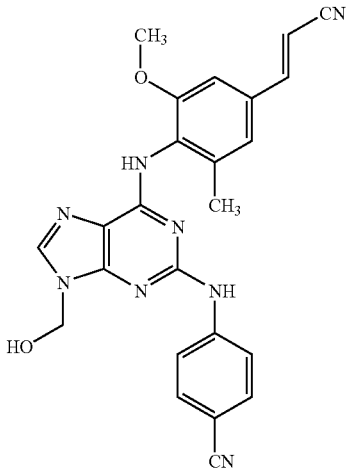

Compound 75 (prepared according to B4a) (50 mg) was dissolved in 10 ml of THF and 50 ml of EtOH and 3 portions of 0.20 gram of $NaBH_4$ were added initially and every half hour. Stirring for 2 hours at 0° C. The reaction mixture was diluted with EtOAc and washed with 1 N HCl, with saturated aqueous $NaHCO_3$ and dried (NaCl (saturated) and $Na_2SO_4$), filtered and concentrated and the residue was purified by preparative TLC using $CH_2Cl_2$/MeOH (95/5) as the eluent. Yield: 15 mg of compound 50 (32%).

EXAMPLE B5 a. Preparation of Compound 51

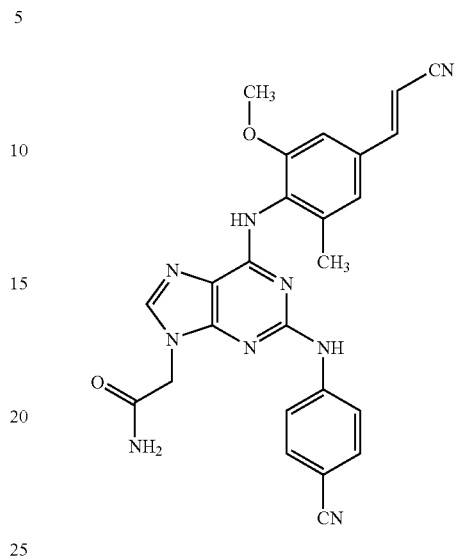

Compound 75 (prepared according to B4a) (15 mg) was dissolved in 2 ml of THF and $NH_3$ 7 N in MeOH (1 ml) was added. Stirring for 100 hours at 20° C. The solvents were evaporated and the residue was stirred in i-$Pr_2O$ and filtered off. Yield: 15 mg of compound 51 (99%).

b. Preparation of Compound 52

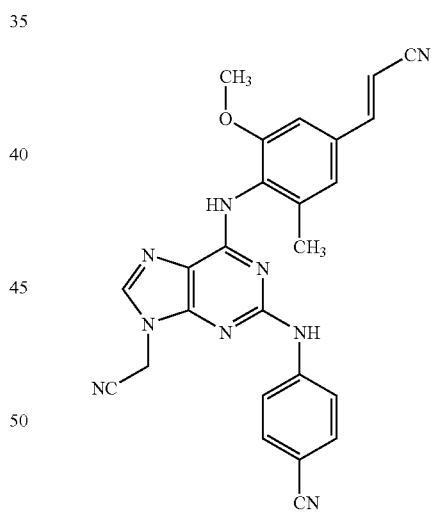

Compound 51 (prepared according to B5.a) (27 mg) was dissolved in 2 ml of THF and $POCl_3$ (4 ml) was added. Stirring for 120 hours at 50° C. The reaction mixture was diluted with i-$Pr_2O$; an oil was formed on the bottom of the flask. The i-$Pr_2$ was decanted and the oil was stirred with 2 N NaOH and EtOAc. The EtOAc fraction was dried (NaCl (saturated) and $Na_2SO_4$), filtered and concentrated and the residue was purified by preparative TLC using $CH_2Cl_2$/MeOH (95/5) as the eluent. Yield: 15 mg of compound 52 (60%).

Tables 1 to 4 list the compounds of formula (I) which were prepared according to one of the above examples.

TABLE 1

(I)

| Co. no. | Exp. no. | R² | R³ | R⁴ᵃ | R⁴ᵇ | X₁ | Physico-chem data. |
|---|---|---|---|---|---|---|---|
| 7 | B1c | CN | CH₃ | CH₃ | CH₃ | O | |
| 8 | B1b | CN | CH₃ | CH₃ | CH₃ | NH | |
| 9 | B1c | CN | C(CH₃)₃ | CH₃ | CH₃ | NH | |
| 10 | B1c | CN | OCH₃ | OCH₃ | OCH₃ | NH | |
| 11 | B1c | CN | CN | CH₃ | CH₃ | O | |
| 12 | B1c | CN | CN | CH₃ | CH₃ | NH | |
| 13 | B1c | CN | -CH₂CH₂CH₂C≡N | CH₃ | CH₃ | NH | |
| 3 | B1c | CN | -CH=CH-C≡N | CH₃ | CH₃ | NH | |
| 14 | B1b | CN | -CH=CH-C≡N | Cl | CH₃ | NH | |
| 2 | B1b | CN | -CH=CH-C≡N | OCH₃ | CH₃ | NH | |
| 40 | B1.f | CN | -C(CH₃)=CH-C≡N | CH₃ | CH₃ | NH | |
| 41 | B1.f | CN | -CH=C(CH₃)-C≡N | CH₃ | CH₃ | NH | (Z) |
| 42 | B1.f | CN | -CH=C(CH₃)-C≡N | CH₃ | CH₃ | NH | (E) |
| 43 | B1.f | CN | -CH=C(CH₃)-C≡N | OCH₃ | CH₃ | NH | |

TABLE 1-continued (I)

[Structure: phenyl (R³ para, R⁴ᵃ and R⁴ᵇ ortho) — X₁ — purine core with 9-(4-methoxybenzyl) on N9 and NH-phenyl-R² at 2-position]

| Co. no. | Exp. no. | R² | R³ | R⁴ᵃ | R⁴ᵇ | X₁ | Physico-chem data. |
|---|---|---|---|---|---|---|---|
| 15 | B1b | CN | (E)-CH=CH-C(O)-N(CH₃)₂ | CH₃ | CH₃ | NH | |
| 16 | B1c | CN | (E)-CH=CH-C(O)-morpholinyl | CH₃ | CH₃ | O | |
| 17 | B1c | CN | (E)-CH=CH-C(O)-morpholinyl | CH₃ | CH₃ | NH | |

TABLE 2

[Structure: phenyl (R³ para, R⁴ᵃ and R⁴ᵇ ortho) — X₁ — purine core with R¹⁷ on N7 and NH-(4-cyanophenyl) at 2-position]

| Co. no. | Exp. no. | R³ | R⁴ᵃ | R⁴ᵇ | R¹⁷ | X₁ | Physico chem data |
|---|---|---|---|---|---|---|---|
| 18 | B1a | OCH₂CH₃ | CH₃ | CH₃ | CH₂-(4-methoxyphenyl) | NH | |
| 44 | B1.b | (E)-CH=CH-CN | CH₃ | CH₃ | CH₃ | NH | |

TABLE 2-continued

Structure: Purine core with R17 on N7, X1-linked aryl (with R4a, R4b, R3) at C6, and 4-cyanoanilino NH at C2.

| Co. no. | Exp. no. | R³ | R⁴ᵃ | R⁴ᵇ | R¹⁷ | X₁ | Physico chem data |
|---|---|---|---|---|---|---|---|
| 4 | B1d | –CH=CH–CN | CH₃ | CH₃ | –CH₂–(4-methoxyphenyl) | O | |
| 19 | B1d | –CH=CH–CN | OCH₃ | OCH₃ | –CH₂–(4-methoxyphenyl) | O | |
| 20 | B1d | –CH=CH–C(O)NH₂ | CH₃ | CH₃ | –CH₂–(4-methoxyphenyl) | O | |
| 21 | B1d | –CH=CH–C(O)N(CH₃)₂ | CH₃ | CH₃ | –CH₂–(4-methoxyphenyl) | O | |
| 1 | B1a | –CH=CH–C(O)N(CH₃)(C₂H₅) | CH₃ | CH₃ | –CH₂–(4-methoxyphenyl) | O | (E) |

TABLE 3

Structure: Purine core with R17 on N9, X1-linked aryl (with R4a, R4b, R3) at C6, and 4-R2-anilino NH at C2.

| Co. no. | Exp. no. | R² | R³ | R⁴ᵃ | R⁴ᵇ | R¹⁷ | X₁ | Physico chem data |
|---|---|---|---|---|---|---|---|---|
| 22 | B2b | CH₃ | CH₃ | CH₃ | CH₃ | H | NH | |
| 23 | B2b | CN | CH₃ | CH₃ | CH₃ | H | O | |
| 24 | B2b | CN | CH₃ | CH₃ | CH₃ | H | NH | |
| 45 | B1f | CN | CH₃ | CH₃ | CH₃ | CH₃ | NH | |
| 25 | B2b | CN | OCH₃ | CH₃ | CH₃ | H | NH | |
| 26 | B2b | CN | OCH₃ | OCH₃ | OCH₃ | H | NH | |

TABLE 3-continued
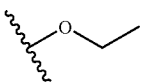
| Co. no. | Exp. no. | R² | R³ | R⁴ᵃ | R⁴ᵇ | R¹⁷ | X₁ | Physico chem data |
|---|---|---|---|---|---|---|---|---|
| 27 | B2b | CN | C(CH₃)₃ | CH₃ | CH₃ | H | NH | |
| 28 | B2b | CN | CN | CH₃ | CH₃ | H | O | |
| 29 | B2b | CN | CN | CH₃ | CH₃ | H | NH | |
| 46 | B1.b | CN | CN | CH₃ | CH₃ | CH₃ | NH | |
| 30 | B2a | CN | 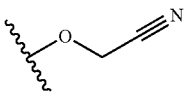 | CH₃ | CH₃ | H | NH | |
| 31 | B2b | CN | 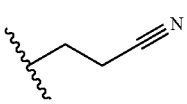 | CH₃ | CH₃ | H | NH | |
| 32 | B2b | CN | 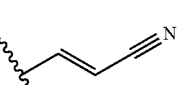 | CH₃ | CH₃ | H | NH | |
| 33 | B2a | CN | 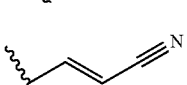 | CH₃ | CH₃ | H | O | |
| 34 | B2b | CN | 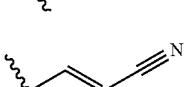 | CH₃ | CH₃ | H | NH | |
| 47 | B1.b | CN | 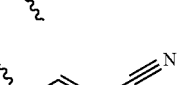 | CH₃ | CH₃ | CH₃ | NH | |
| 6 | B2b | CN |  | OCH₃ | CH₃ | H | NH | |
| 48 | B3c | CN |  | OCH₃ | CH₃ |  | NH | |
| 49 | B3.a | CN |  | OCH₃ | CH₃ |  | NH | |
| 50 | B4.b | CN |  | OCH₃ | CH₃ | (CH₂CH₂OH) | NH | |

TABLE 3-continued
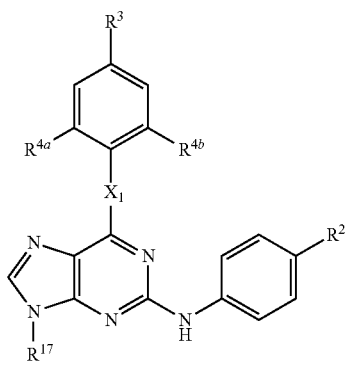
| Co. no. | Exp. no. | R² | R³ | R⁴ᵃ | R⁴ᵇ | R¹⁷ | X₁ | Physico chem data |
|---|---|---|---|---|---|---|---|---|
| 51 | B5.a | CN | 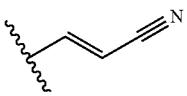 | OCH₃ | CH₃ |  | NH | |
| 52 | B5.b | CN | 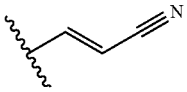 | OCH₃ | CH₃ | 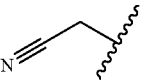 | NH | |
| 35 | B2a | CN | 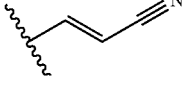 | OCH₃ | OCH₃ | H | O | |
| 53 | B2.b | CN | 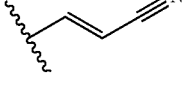 | OCH₃ | Cl | H | NH | |
| 54 | B2.b | CN | 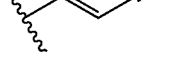 | Cl | CH₃ | H | NH | (E) |
| 55 | B2.b | CN | 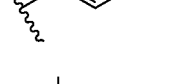 | Cl | Cl | H | NH | (E) |
| 56 | B2.b | CN | 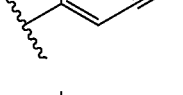 | CH₃ | CH₃ | H | NH | |
| 57 | B1.f | CN | 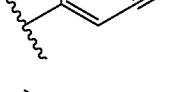 | CH₃ | CH₃ | CH₃ | NH | (E) |
| 58 | B2.b | CN | 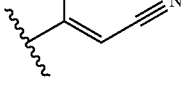 | CH₃ | CH₃ | H | NH | (E) |
| 59 | B1.f | CN | 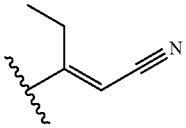 | CH₃ | CH₃ | CH₃ | NH | |

TABLE 3-continued
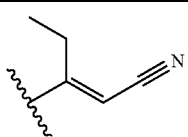
| Co. no. | Exp. no. | R² | R³ | R⁴ᵃ | R⁴ᵇ | R¹⁷ | X₁ | Physico chem data |
|---|---|---|---|---|---|---|---|---|
| 60 | B3.b | CN | 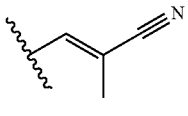 | CH₃ | CH₃ | 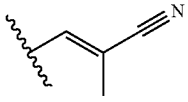 | NH | (E) |
| 61 | B2.b | CN | 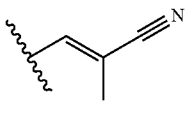 | CH₃ | CH₃ | H | NH | (Z) |
| 62 | B2.b | CN | 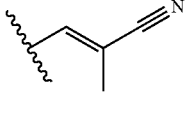 | CH₃ | CH₃ | H | NH | |
| 63 | B2.b | CN | 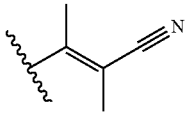 | OCH₃ | CH₃ | H | NH | |
| 64 | B1.b | CN | 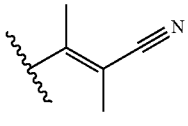 | CH₃ | CH₃ | CH₃ | NH | |
| 65 | B2.b | CN | 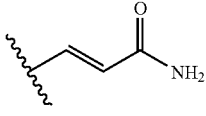 | CH₃ | CH₃ | H | NH | (E) |
| 66 | B1.f | CN | 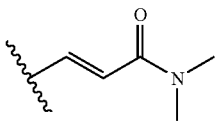 | CH₃ | CH₃ | CH₃ | NH | (E) |
| 36 | B2a | CN |  | CH₃ | CH₃ | H | O | |
| 37 | B2b | CN |  | CH₃ | CH₃ | H | NH | |

TABLE 3-continued
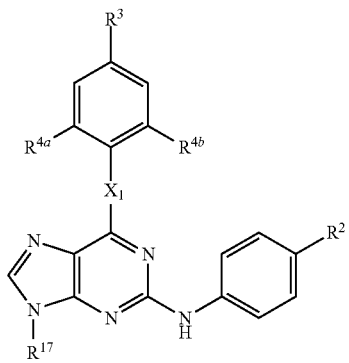
| Co. no. | Exp. no. | R² | R³ | R⁴ᵃ | R⁴ᵇ | R¹⁷ | X₁ | Physico chem data |
|---|---|---|---|---|---|---|---|---|
| 67 | B2.a | CN | 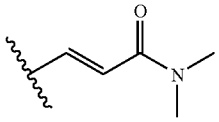 | CH₃ | CH₃ | H | O | |
| 5 | B2a | CN | 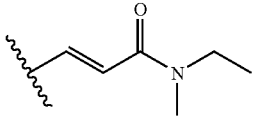 | CH₃ | CH₃ | H | O | |
| 38 | B2b | CN | 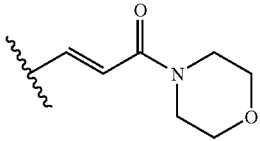 | CH₃ | CH₃ | H | NH | |
| 39 | B2b | CN | 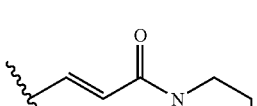 | CH₃ | CH₃ | H | O | |
| 68 | B1.b | 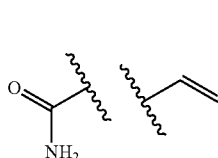 | 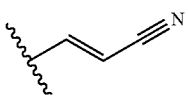 | CH₃ | CH₃ | CH₃ | NH | (E) |
| 75 | B4.a | CN | 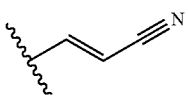 | OCH₃ | CH₃ | CH₂—C(=O)—OCH₃ | NH | |

TABLE 4

[Structure: purine core with 4-cyanophenyl-NH at position 6, and 2,6-dimethyl-4-R²ᵃ-phenyl-NH at position 2, with R¹⁷ on N9]

| Co. no. | Exp. no. | R²ᵃ | R¹⁷ | Physico chem data |
|---|---|---|---|---|
| 69 | B2.c | CN | H | |
| 70 | B2.c | -CH=CH-CN | H | |
| 71 | B1.e | CH₃ | 4-methoxybenzyl | |
| 72 | B1.e | CN | 4-methoxybenzyl | |
| 73 | B1.e | -CH=CH-CN | 4-methoxybenzyl | |
| 74 | B2c | CH₃ | H | |

C. Analytical Data

Table 5 lists ¹H NMR data for the compounds of formula (I). All spectra were recorded (300 MHz) in DMSO-d6, unless otherwise specified. The shifts (δ) are in ppm, relative to TMS. Between parenthesis, the number of H's, the peak-form and the coupling (J) in Hz are indicated. The following abbreviations were used: s: singlet, bs: broad singlet, ds: double singlet, d: doublet, dd: double doublet, t: triplet, dt: double triplet, q: quartet, dq: double quartet, h: heptet, m: multiplet.

TABLE 5

| Co. No. | NMR results |
|---|---|
| 67 | δ=13.23(1, bs), 8.23(1, s), 7.61(2, d, 9), 7.60(2, s), 7.50(1, d, 15), 7.40(2, d, 9), 7.23(1, d, 15), 2.95 & 3.20(6, ds), 2.11(6, s) |
| 54 | δ=12.70(1, bs), 9.46(2, bs), 7.98(1, s), 7.79(1, bs), 7.50-7.75(4, m), 7.39(2, d, 9), 6.59(1, d, 17), 2.24(3, s) |
| 55 | δ=12.74(1, bs), 9.77(1, bs), 9.51(1, bs), 7.99(1, bs), 7.95(2, s), 7.60-7.80(3, m), 7.42(2, d, 9), 6.72(1, d, 17) |
| 45 | δ=9.53(1, bs), 9.13(1, bs), 7.95(1, s), 7.66(2, d, 8), 7.31(2, d, 8), 6.97(2, s), 3.69(3, s), 2.33(3, s), 2.10(6, s) |
| 44 | δ=9.41(1, bs), 8.44(1, bs), 8.12(1, bs), 7.69(1, d, 17), 7.50-7.60(4, m), 7.28(2, d, 9), 6.51(1, d, 17), 4.10(3, s), 2.21(6, s) |
| 70 | δ=12.55(1, bs), 9.99(1, bs), 8.44(1, bs), 8.00(2, bs), 7.90(1, bs), 7.62(1, d, 17), 7.44(2, s), 7.44(2, bs), 6.41(1, d, 17), 2.18(6, s) |
| 73 | δ=10.06(1, bs), 8.60(1, bs), 8.03(1, s), 7.89(2, bs), 7.64(1, d, 17), 7.47(2, s), 7.40(2, bs), 7.23(2, d, 9), 6.89(2, d, 9), 6.44(1, d, 17), 5.15(2, bs), 3.73(3, s), 2.16(6, s) |
| 47 | δ=9.58(1, bs), 9.37(1, bs), 7.97(1, s), 7.60-7.70(3, m), 7.48(2, s), 7.33(2, d, 9), 6.47(1, d, 17), 3.70(3, s), 2.17(6, s) |

TABLE 5-continued

| Co. No. | NMR results |
|---|---|
| 53 | δ=12.65(1, bs), 9.46(1, bs), 9.24(1, bs), 7.96(1, bs), 7.60-7.80(3, m), 7.52(1, s), 7.30-7.48(3, m), 6.69(1, d, 17), 3.77(3, s) |
| 46 | δ=9.61(1, bs), 9.51(1, bs), 7.99(1, s), 7.69(2, s), 7.64(2, d, 8), 7.38(2, d, 8), 3.70(3, s), 2.20(6, s) |
| 63 | δ=12.61(1, bs), 9.41(1, bs), 8.93(1, bs), 7.94(1, s), 7.70(2, d, 8), 7.30-7.50(3, m), 7.05(2, s), 3.70(3, s), 2.20(6, s) |
| 43 | δ=9.49(1, bs), 9.04(1, bs), 8.08(1, s), 7.70(2, d, 8), 7.35-7.50(3, m), 7.31(2, d, 9), 7.05(1, s), 7.04(1, s), 6.92(2, d, 9), 5.25(2, s), 3.71(3, s), 3.70(3, s), 2.20(6, s) |
| 62 | δ=12.64(1, bs), 9.41(1, bs), 9.25(1, bs), 7.97(1, s), 7.69(2, d, 8), 7.30-7.45(3, m), 7.28(2, s), 2.19(9, m) |
| 42 | δ=9.49(1, bs), 9.35(1, bs), 8.10(1, s), 7.69(2, d, 8), 7.30-7.45(5, m), 7.27(2, s), 6.92(2, d, 9), 5.25(2, s), 3.72(3, s), 2.18(9, s) |
| 71 | δ=10.00(1, bs), 7.80-8.50(4, m), 7.20-7.40(4, m), 6.95(2, s), 6.88(2, d, 8), 5.15(2, bs), 3.73(3, s), 2.32(3, s), 2.10(6, s) |
| 61 | δ=12.66(1, bs), 9.43(1, bs), 9.27(1, bs), 7.96(1, s), 7.70(2, d, 8), 7.50(2, s) 7.39(2, d, 8), 7.27(1, s), 2.19(6, s), 2.17(3, s) |
| 41 | δ.=9.50(1, bs), 9.36(1, bs), 8.10(1, s), 7.70(2, d, 8), 7.49(2, s) 7.40(2, d, 8), 7.33(2, d, 9), 7.27(1, s), 6.92(2, d, 9), 5.25(2, s), 3.72(3, s), 2.18(6, s), 2.16(3, s) |
| 69 | δ=12.60(1, bs), 10.04(1, bs), 8.59(1, bs), 8.01(2, d, 8), 7.93(1, s), 7.62(2, s) 7.52(2, d, 8), 2.20(6, s) |
| 72 | δ=10.11(1, bs), 8.75(1, bs), 8.05(1, s), 7.89(2, d, 8), 7.66(2, s) 7.45(2, d, 8), 7.22(2, d, 9), 6.89(2, d, 9), 5.15(2, s), 3.73(3, s), 2.18(6, s) |
| 64 | δ=9.58(1, bs), 9.34(1, bs), 7.97(1, s), 7.65(2, d, 8), 7.43(1, s), 7.33(2, d, 8), 7.29(2, s) 3.70(3, s), 2.18(9, s) |
| 51 | δ=9.53(1, bs), 9.08(1, bs), 7.92(1, s), 7.60-7.70(4, m), 7.00-7.40(5, m), 6.57(1, d, 17), 4.75(2, s) 3.73(3, s), 2.20(3, s) |
| 52 | δ=9.66(1, bs), 9.26(1, bs), 8.05(1, s), 7.60-7.75(3, m), 7.00-7.40(4, m), 6.58(1, d, 17), 5.36(2, s) 3.72(3, s), 2.19(3, s) |
| 50 | δ=9.53(1, bs), 9.06(1, bs), 7.94(1, s), 7.60-7.75(3, m), 7.25-7.40(3, m), 7.22(1, s), 6.57(1, d, 16), 5.01(1, t, 5), 4.14(2, t, 5), 3.70-3.80(5, m), 2.19(3, s) |
| 48 | δ=9.54(1, bs), 9.06(1, bs), 8.02(1, s), 7.60-7.75(3, m), 7.25-7.40(3, m), 7.21(1, s), 6.57(1, d, 17), 4.13(2, q, 7), 3.72(3, s), 2.18(3, s), 1.43(3, t, 7) |
| 49 | δ=9.49(1, bs), 9.05(1, bs), 8.10(1, s), 7.60-7.75(3, m), 7.25-7.40(3, m), 7.21(1, s), 6.56(1, d, 17), 4.67(1, h, 7), 3.72(3, s), 2.19(3, s), 1.55(6, d, 7) |
| 56 | δ=12.66(1, bs), 9.41(1, bs), 9.26(1, bs), 7.96(1, s), 7.71(2, d, 8), 7.46(2, s), 7.38(2, d, 8), 6.14(1, s), 2.46(3, s), 2.20(6, s) |
| 40 | δ=9.48(1, bs), 9.35(1, bs), 8.11(1, bs), 7.71(2, d, 8), 7.45(2, s), 7.39(2, d, 8), 7.34(2, d, 9), 6.92(2, d, 9), 6.14(1, s), 5.25(2, s), 3.71(3, s), 2.46(3, s), 2.18(6, s) |
| 58 | δ=12.65(1, bs), 9.42(1, bs), 9.26(1, bs), 7.96(1, s), 7.67(2, d, 8), 7.42(2, s), 7.35(2, d, 8), 6.03(1, s), 2.90(2, q, 8), 2.20(6, s), 1.12(3, t, 8) |
| 57 | δ=9.56(1, bs), 9.34(1, bs), 7.97(1, bs), 7.67(2, d, 8), 7.47(2, s), 7.33(2, d, 8), 6.15(1, s), 3.70(3, s), 2.47(3, s), 2.19(6, s) |
| 59 | δ=9.59(1, bs), 9.34(1, bs), 7.97(1, bs), 7.64(2, d, 8), 7.43(2, s), 7.31(2, d, 8), 6.03(1, s), 3.70(3, s), 2.91(2, q, 8), 2.19(6, s), 1.12(3, t, 8) |
| 65 | δ=12.64(1, bs), 9.43(1, bs), 9.20(1, bs), 7.96(1, s), 7.67(2, d, 8), 7.36(2, d, 8), 7.10(2, s), 2.37(3, s), 2.19(6, s), 1.89(3, s) |
| 66 | δ=9.59(1, bs), 9.28(1, bs), 7.97(1, bs), 7.64(2, d, 8), 7.32(2, d, 8), 7.11(2, s), 3.70(3, s), 2.38(3, s), 2.18(6, s), 1.88(3, s) |
| 68 | δ=9.22(2, bs), 7.92(1, s), 7.45-7.70(9, m), 7.01(1, d, 16), 3.69(3, s), 2.18(6, s) |
| 60 | δ=9.67(1, bs), 9.52(1, bs), 8.08(1, bs), 7.67(2, d, 8), 7.44(2, s), 7.33(2, d, 8), 6.04(1, s), 5.37(2, s), 2.91(2, q, 8), 2.20(6, s), 1.12(3, t, 8) |
| 1 | δ=9.81(H, bs), 8.66(H, s), 7.57(2H, d, 8), 7.54(2H, s), 7.43-7.50(H, m), 7.36(2H, d, 8), 7.20(2H, d, 8), 7.16(H, d, 16), 6.90(2H, d, 8), 5.57(2H, s), 3.71(3H, s), 3.57 & 3.45(2H, dq, 7), 3.15 & 2.93(3H, ds), 1.89(6H, s), 1.17 & 1.07(3H, dt, 7) |
| 2 | δ=9.50(H, bs), 9.07(H, bs), 8.08(H, bs), 7.70(2H, d, 9), 7.65(H, d, 17), 7.40(2H, d, 9), 7.31(2H, d, 8), 7.30(H, s), 7.20(H, s), 6.91(2H, d, 8), 6.55(H, d, 17), 5.25(2H, s), 3.71(6H, s), 2.18 3H, s) |
| 3 | δ=9.52(H, bs), 9.40(H, bs), 8.12(H, bs), 7.60-7.80 3H, m), 7.48(2H, s), 7.30-7.43(4H, m), 6.93(2H, d, 8), 6.47(H, d, 17), 5.26(2H, s), 3.71(3H, s), 2.17(6H, s) |
| 4 | (CDCl3)δ=8.08(H, s), 7.51(2H, d, 9), 7.39(H, d, 17), 7.35(2H, d, 9), 7.24(2H, s), 7.20(H, bs), 7.14(2H, d, 9), 6.87(2H, d, 9), 5.89(H, d, 17), 5.51(2H, s), 3.79(3H, s), 1.97(6H, s) |
| 5 | δ=13.15(H, bs), 9.86(H, s), 8.23(H, s), 7.59(2H, d, 8), 7.58(2H, d, 8), 7.41-7.53 H, m), 7.37(2H, d, 8), 7.18(H, d, 15), 3.59 & 3.42(2H, dq, 7), 3.16 & 2.93(3H, ds), 2.11(6H, s), 1.18 & 1.08(3H, dt, 7) |

TABLE 5-continued

| Co. No. | NMR results |
|---|---|
| 6 | δ=12.61(H, bs), 9.42(H, bs), 8.95(H, bs), 7.95(H, bs), 7.71(2H, d, 9), 7.65(H, d, 17), 7.39(2H, d, 9), 7.30(H, s), 7.21(H, s), 6.55(H, d, 17), 3.73(3H, s), 2.19(3H, s) |
| 7 | (CDCl3)δ=7.79(1, s), 7.35-7.50(4, m), 7.31(2, d, 9), 7.17(1, bs), 6.97(2, s), 6.91(2, d, 9), 5.27(2, s), 3.81(3, s), 2.38(3, s), 2.13(6, s). |
| 8 | δ=9.47(1, bs), 9.17(1, bs), 8.10(1, bs), 7.72(2, d, 8), 7.30-7.45(4, m), 6.90-7.00(4, m), 5.25(2, s), 3.72(3, s), 2.31(3, s), 2.10(6, s) |
| 9 | (CDCl3)δ=7.59(1, bs), 7.52(2, d, 8), 7.35(2, d, 8), 7.27(2, d, 9), 7.16(2, s), 7.03(1, bs), 6.93(1, bs), 6.88(2, d, 9), 5.21(2, s), 3.79(3, s), 2.25(6, s), 1.38(9, s) |
| 10 | (CDCl3)δ=7.55-7.65(3, m), 7.42(2, d, 8), 7.26(2, d, 9), 7.08(1, bs), 6.89(2, d, 9), 6.81(1, bs), 6.25(2, s), 5.21(2, s), 3.89(3, s), 3.80(3, s), 3.76(6, s) |
| 11 | (CDCl3)δ=7.83(1, s), 7.45-7.55(6, m), 7.32(2, d, 9), 7.10(1, bs), 6.92(2, d, 9), 5.30(2, s), 3.81(3, s), 2.20(6, s) |
| 12 | (CDCl3)δ=7.50-7.65(3, m), 7.40-7.50(4, m), 7.20-7.35(3, m), 7.06(1, bs), 6.94(2, d, 9), 5.25(2, s), 3.81(3, s), 2.29(6, s) |
| 13 | (CDCl3)δ=8.19(1, bs), 7.82(1, s), 7.54(2, d, 8), 7.41(2, d, 8), 7.20-7.30(3, m), 7.04(2, s), 6.88(2, d, 9), 5.21(2, s), 3.79(3, s), 2.97(2, t, 6), 2.69(2, t, 6), 2.16(6, s) |
| 14 | δ=9.59(1, bs), 9.54(1, bs), 8.12(1, bs), 7.60-7.80(5, m), 7.30-7.45(4, m), 6.92(2. d, 9), 6.59(1, d, 17), 5.26(2, s), 3.71(3, s), 2.23(3, s) |
| 15 | (CDCl3)δ=7.68(1, d, 15), 7.64(1, s), 7.56(2, d, 8), 7.39(2, d, 8), 7.35(2, s), 7.31(2, d, 9), 7.08(2, bs), 6.85-6.95(3, m), 5.24(2, s), 3.81(3, s), 3.22(3, s), 3.10(3, s), 2.28(6, s) |
| 16 | (CDCl3)δ=7.81(1, s), 7.74(1, d, 17), 7.40-7.50(4, m), 7.27-7.35(4, m), 7.16(1, bs), 6.92(2, d, 9), 6.85(1, d, 17), 5.28(2, s), 3.81(3, s), 3.76(8, bs), 2.18(6, s) |
| 17 | δ=9.58(1, bs), 7.95(2, d, 8), 7.40-7.65(6, m), 7.29(1, d, 17), 7.12(2, d, 9), 6.96(2, d, 9), 5.28(1, s), 5.02(2, s), 3.79(3, s), 3.50-3.78(8, m), 2.31(6, s) |
| 18 | δ=9.44(1, bs), 8.36(1, s), 7.88(1, bs), 7.53(2, d, 8), 7.28(2, d, 8), 7.11(2, d, 9), 6.92(2, d, 9), 6.74(2, s), 5.70(2, s), 4.06(2, q, 7), 3.71(3, s), 1.89(6, s), 1.36(3, t, 7) |
| 19 | (CDCl3)δ=7.99(1, bs), 7.54(2, d, 8), 7.45(1, d, 17), 7.30-7.40(4, m), 7.13(1, bs), 6.87(2, d, 9), 6.78(2, s), 5.94(1, d, 17), 5.50(2, s), 3.80(3, s), 3.77(6, s) |
| 20 | δ=9.83(1, bs), 8.68(1, s), 7.61(2, d, 8), 7.51(1, bs), 7.35-7.50(5, m), 7.21(2, d, 9), 7.11(1, bs), 6.91(2, d, 9), 6.62(1, d, 17), 5.58(2, s), 3.71(3, s), 1.89(6, s) |
| 21 | (CDCl3)δ=8.07(1, s), 7.68(1, d, 17), 7.46(2, d, 8), 7.30-7.36(4, m), 7.24(1, bs), 7.16(2, d, 9), 6.85-6.95(3, m), 5.52(2, s), 3.80(3, s), 3.23(3, s), 3.10(3, s), 1.98(6, s) |
| 23 | δ=9.85(1, bs), 8.20(1, bs), 7.62(2, d, 8), 7.42(2, d, 8), 7.03(2, s), 2.34(3, s), 2.04(6, s) |
| 24 | δ=12.64(1, bs), 9.39(1, bs), 9.07(1, bs), 7.96(1, bs), 7.72(2, d, 8), 7.38(2, d, 8), 6.98(2, s), 2.31(3, s), 2.12(6, s) |
| 25 | δ=12.65(1, bs), 9.43(1, bs), 9.04(1, bs), 8.03(1, s), 7.73(2, d, 8), 7.39(2, d, 8), 6.77(2, s), 3.79(3, s), 2.14(6, s) |
| 26 | δ=12.50(1, bs), 9.39(1, bs), 8.37(1, bs), 7.93(1, bs), 7.76(2, d, 8), 7.43(2, d, 8), 6.38(2, s), 3.86(3, s), 3.69(6, s) |
| 27 | δ=12.64(1, bs), 9.42(1, bs), 9.09(1, bs), 7.97(1, bs), 7.69(2, d, 8), 7.35(2, d, 8), 7.18(2, s), 2.15(6, s), 1.34(9, s) |
| 28 | δ=13.24(1, bs), 9.90(1, bs), 8.27(1, s), 7.80(2, s), 7.60(2, d, 8), 7.48(2, d, 8), 2.14(6, s) |
| 29 | δ=12.73(1, bs), 9.47(2, bs), 8.01(1, s), 7.65-7.75(4, m), 7.44(2, d, 8), 2.21(6, s) |
| 30 | δ=12.73(1, bs), 9.41(1, bs), 9.02(1, bs), 8.03(1, s), 7.69(2, d, 8), 7.36(2, d, 8), 6.73(2, s), 4.06(2, q, 7), 2.12(6, s), 1.36(3, t, 7) |
| 31 | δ=12.61(1, bs), 9.40(1, bs), 9.06(1, bs), 7.95(1, bs), 7.69(2, d, 8), 7.39(2, d, 8), 6.90(2, s), 5.20(2, s), 2.16(6, s) |
| 32 | δ=12.65(1, bs), 9.42(1, bs), 9.12(1, bs), 7.97(1, s), 7.71(2, d, 8), 7.41(2, d, 8), 7.10(2, s), 2.88(4, s), 2.15(6, s) |
| 33 | δ=13.21(1, bs), 9.88(1, bs), 8.25(1, s), 7.70(1, d, 17), 7.60(2, d, 9), 7.56(2, s), 7.42(2, d, 9), 6.49(1, d, 17), 2.11(6, s) |
| 34 | δ=12.66(1, bs), 9.42(1, bs), 9.28(1, bs), 7.96(1, s), 7.60-7.75(3, m), 7.47(2, s), 7.37(2, d, 9), 6.46(1, d, 17), 2.18(6, s) |
| 35 | δ=13.15(1, bs), 9.88(1, bs), 8.24(1, bs), 7.71(1, d, 17), 7.62(2, d, 8), 7.45(2, d, 8), 7.23(2, s), 6.66(1, d, 17), 3.75(6, s) |
| 36 | δ=13.10(1, bs), 9.84(1, bs), 8.22(1, s), 7.30-7.80(8, m), 7.12(1, bs), 6.65(1, d, 17), 2.11(6, s) |
| 37 | δ=12.64(1, bs), 9.41(1, bs), 9.23(1, bs), 7.96(1, s), 7.69(2, d, 8), 7.51(2, s), 7.46(1, d, 15), 7.35(2, d, 8), 7.20(1, d, 15), 3.19(3, s), 2.95(3, s), 2.19(6, s) |
| 38 | δ=12.64(1, bs), 9.42(1, bs), 9.23(1, bs), 7.96(1, bs), 7.67(2, d, 8), 7.40-7.60(3, m), 7.34(2, d, 8), 7.26(1, d, 15), 3.50-3.78(8, m), 2.18(6, s) |

TABLE 5-continued

| Co. No. | NMR results |
|---|---|
| 39 | δ=13.19(1, bs), 9.89(1, bs), 8.25(1, s), 7.45-7.65(5, m), 7.39(2, d, 9), 7.29(1, d, 17), 3.60-3.80(8, m), 2.11(6, s) |

D. Pharmacological Example

The in vitro pharmacological activity of the present compounds was examined using one of the following rapid, sensitive and automated assay methods.

Method A

An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in M) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% effective concentration ($EC_{50}$ in M). The ratio of $CC_{50}$ to $EC_{50}$ was defined as the selectivity index (SI).

Method B

An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. In these cells, engineered with GFP (and an HIV-specific promotor), ongoing HIV-infection was measured fluorometrically. Cytotoxicity is measured in the same cells, but engineered with GFP under a constitutional promotor. The infection (or inhibition thereof) of HIV infected cells and the fluorescence of mock-infected cells is assessed by the fluorescent GFP signal generated by the two above mentioned cell lines.

The 50% effective concentration ($EC_{50}$ in μM) was defined as the concentration of compound that reduced the fluorescence of HIV-infected cells by 50%. The 50% cytotoxic concentration ($CC_{50}$ in μM) was defined as the concentration of compound that reduced fluorescence of the mock-infected cells by 50%. The ratio of $CC_{50}$ to $EC_{50}$ was defined as the selectivity index (SI).

The compounds of formula (I) were shown to inhibit HIV-1 effectively. Particular $EC_{50}$, $CC_{50}$ and SI values are listed in Table 6 hereinbelow.

Table 6 lists the $pEC_{50}$ ($-\log EC_{50}$), $pCC_{50}$ ($-\log CC_{50}$) and pSI ($pCC_{50}-pEC_{50}$) values for the compounds of formula (I). For example, a compound with a $EC_{50}$ value of $10^{-9}$M, i.e. $pEC_{50}=9$, and a $CC_{50}$ value of $10^{-5}$ M, i.e. $pCC_{50}=5$, has a SI of $10^{-5}$ M/$10^{-9}$M=10.000, i.e. a pSI of 5-9=-4.

TABLE 6

| Co. No. | $pEC_{50}$ (M) | $pCC_{50}$ | pSI | Method |
|---|---|---|---|---|
| 25 | 8.5 | <4.5 | <-4 | A |
| 23 | 8.2 | <4.6 | <-3.6 | A |
| 28 | 9.0 | <4.6 | <-4.4 | A |
| 24 | 8.4 | 4.3 | -4.1 | A |
| 21 | 8.4 | 4.8 | -3.6 | B |
| 4 | 8.4 | 5.0 | -3.4 | B |
| 20 | 8.4 | 5.2 | -3.2 | B |
| 33 | 8.5 | 5.0 | -3.5 | B |
| 13 | 8.2 | 5.2 | -3.1 | B |
| 32 | 8.3 | 4.8 | -3.5 | B |
| 26 | 9.3 | 5.0 | -4.3 | B |
| 19 | 9.2 | <4.6 | <-4.6 | B |
| 3 | 8.5 | 5.9 | -2.6 | B |
| 34 | 8.5 | 4.8 | -3.7 | B |
| 35 | 8.4 | 4.9 | -3.5 | B |
| 29 | 8.7 | 4.9 | -3.8 | B |
| 37 | 8.1 | 5.4 | -2.7 | B |
| 30 | 8.8 | 4.8 | -4.0 | B |
| 1 | 8.4 | <4.6 | <-3.8 | B |
| 2 | 9.0 | 5.3 | -3.7 | B |
| 5 | 8.5 | 5.3 | -3.2 | B |
| 6 | 9.0 | 6.1 | -2.9 | B |
| 31 | 9.3 | <4.6 | <-4.7 | B |
| 14 | 8.3 | 5.5 | -2.8 | B |
| 54 | 8.7 | 5.5 | 3.2 | B |
| 55 | 8.6 | 5.6 | 3.0 | B |
| 45 | 9.2 | <4.6 | >4.6 | B |
| 46 | 9.4 | <4.6 | >4.8 | B |
| 72 | 8.5 | <4.6 | >3.9 | B |
| 64 | 9.3 | <4.6 | >4.7 | B |
| 53 | 8.7 | 6.1 | 2.6 | B |
| 42 | 8.0 | <4.6 | >3.4 | B |
| 62 | 8.6 | <4.6 | >4.0 | B |
| 43 | 8.0 | <4.6 | >3.4 | B |
| 52 | 9.3 | 5.7 | 3.6 | B |
| 48 | 9.2 | <4.6 | >4.6 | B |
| 50 | 9.2 | 5.8 | 3.4 | B |
| 63 | 8.4 | 5.1 | 3.3 | B |
| 49 | 9.0 | 5.5 | 3.5 | B |
| 44 | 8.0 | 4.7 | 3.3 | B |
| 57 | 9.0 | <4.6 | >4.4 | B |
| 59 | 8.5 | <4.6 | >3.9 | B |
| 56 | 8.4 | <4.6 | >3.8 | B |
| 58 | 8.3 | 5.1 | 3.2 | B |
| 65 | 8.1 | 5.0 | 3.1 | B |
| 60 | 8.6 | 5.0 | 3.6 | B |
| 68 | 8.0 | <4.6 | >3.4 | B |
| 73 | 8.3 | <4.6 | >3.7 | B |

The invention claimed is:

1. A compound of formula

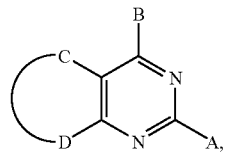

(I)

or a pharmaceutically acceptable addition salt, or a stereochemically isomeric form thereof, wherein
A and B each represents a radical of formula

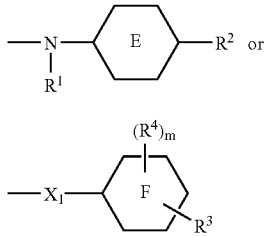

(a)

(b)

wherein
ring E represents phenyl, pyridyl, pyridazinyl, pyrimidinyl or pyrazinyl;
ring F represents phenyl, pyridyl, pyridazinyl, pyrimidinyl or pyrazinyl;
$R^1$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;
$R^2$ represents cyano; $C_{1-6}$alkyl substituted with cyano, aminocarbonyl or mono- or di($C_{1-4}$alkyl)aminocarbonyl; $C_{2-6}$alkenyl substituted with cyano, aminocarbonyl or mono- or di($C_{1-4}$alkyl)aminocarbonyl; or $C_{2-6}$alkynyl substituted with cyano, aminocarbonyl or mono- or di($C_{1-4}$alkyl)aminocarbonyl;
$X_1$ represents —$NR^5$—; —NH—NH—; —N=N—; —O—; —C(=O)—; —$C_{1-4}$alkanediyl-; —CHOH—; —S—; —S(=O)$_p$—; —$X_2$—$C_{1-4}$alkanediyl-; —$C_{1-4}$alkanediyl-$X_2$—; or —$C_{1-4}$alkanediyl-$X_2$—$C_{1-4}$alkanediyl-;
$X_2$ represents —$NR^5$—; —NH—NH—; —N=N—; —O—; —C(=O)—; —CHOH—; —S—; or —S(=O)$_p$—;
m represents an integer of value 1, 2, 3 or 4;
$R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from $R^{3a}$;
$C_{1-6}$alkyloxy optionally substituted with one or more substituents each independently selected from $R^{3a}$; $C_{1-6}$alkyloxy$C_{1-6}$alkyl optionally substituted with one or more substituents each independently selected from $R^{3a}$; $C_{2-6}$alkenyl optionally substituted with one or more substituents each independently selected from $R^{3a}$; $C_{2-6}$alkynyl optionally substituted with one or more substituents each independently selected from $R^{3a}$; —C(=N—O—$R^8$)—$C_{1-4}$alkyl; $R^7$ or —$X_3$—$R^7$;
$R^{3a}$ represents halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$;
$X_3$ represents —$NR^5$—; —NH—NH—; —N=N—; —O—; —C(=O)—; —S—; —S(=O)$_p$—; —$X_{4a}$—$C_{1-4}$alkanediyl-; —$C_{1-4}$alkanediyl-$X_{4b}$—; —$C_{1-4}$alkanediyl-$X_{4a}$—$C_{1-4}$alkanediyl-; or —C(=N—$OR^8$)—$C_{1-4}$alkanediyl-;
$X_{4a}$ represents —$NR^5$—; —NH—NH—; —N=N—; —C(=O)—; —S—; or —S(=O)$_p$—;

$X_{4b}$ represents —NH—NH—; —N=N—; —O—; —C(=O)—; —S—; or —S(=O)$_p$—;
each $R^4$ independently represents hydroxy; halo; $C_{1-6}$alkyl optionally substituted with one or more substituents each independently selected from $R^{4a}$; $C_{2-6}$alkenyl optionally substituted with one or more substituents each independently selected from $R^{4a}$;
$C_{2-6}$alkynyl optionally substituted with one or more substituents each independently selected from $R^{4a}$; $C_{3-7}$cycloalkyl; $C_{1-6}$alkyloxy; $C_{1-6}$alkyloxycarbonyl; $C_{1-6}$alkylcarbonyloxy; carboxyl; formyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; —S(=O)$_p$$R^6$; —NH—S(=O)$_p$$R^6$; —C(=O)$R^6$; —NHC(=O)H; —C(=O)NHNH$_2$; NHC(=O)$R^6$; C(=NH)$R^6$; or $R^7$;
$R^{4a}$ represents halo, cyano, $NR^9R^{10}$, hydroxy or —C(=O)$R^6$;
$R^5$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl or $C_{1-6}$alkylcarbonyloxy; or $C_{1-6}$alkyloxy$C_{1-6}$alkylcarbonyl substituted with $C_{1-6}$alkyloxycarbonyl;
$R^6$ represents $C_{1-6}$alkyl, amino, mono- or di($C_{1-4}$alkyl)amino or polyhalo$C_{1-4}$alkyl;
$R^7$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may, whenever possible, optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro,
polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$alkanediyl-;
$R^{7a}$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may optionally be substituted with one, two, three, four or five substituents each independently selected from halo, hydroxy, mercapto,
$C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy,
$C_{1-6}$alkyloxycarbonyl, $C_{1-6}$alkylthio, cyano, nitro,
polyhalo$C_{1-6}$alkyl, polyhalo$C_{1-6}$alkyloxy, aminocarbonyl, —CH(=N—O—$R^8$);
$R^8$ represents hydrogen, $C_{1-4}$alkyl optionally substituted with aryl, or aryl;
$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl) amino; mono- or di($C_{1-6}$alkyl)aminocarbonyl; —CH(=$NR^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalo$C_{1-4}$alkyl, polyhalo$C_{1-4}$alkyloxy, polyhalo$C_{1-4}$alkylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, or R$^7$; or R$^9$ and R$^{10}$ may be taken together to form a bivalent radical of formula —CH$_2$—CH$_2$—CH$_2$—CH$_2$— (d-1);

—CH$_2$—CH$_2$—CH$_2$—CH$_2$—CH$_2$— (d-2);

—CH$_2$—CH$_2$—O—CH$_2$—CH$_2$— (d-3);

—CH$_2$—CH$_2$—S—CH$_2$—CH$_2$— (d-4);

—CH$_2$—CH$_2$—NR$^{12}$—CH$_2$—CH$_2$— (d-5); or

—CH$_2$—CH=CH—CH$_2$— (d-6);

R$^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

R$^{12}$ represents hydrogen or $C_{1-4}$alkyl;

R$^{13}$ and R$^{14}$ each independently represent $C_{1-6}$alkyl optionally substituted with cyano, aminocarbonyl or mono- or di($C_{1-4}$alkyl)aminocarbonyl; $C_{2-6}$alkenyl optionally substituted with cyano, aminocarbonyl or mono- or di($C_{1-4}$alkyl)aminocarbonyl; $C_{2-6}$alkynyl optionally substituted with cyano, aminocarbonyl or mono- or di($C_{1-4}$alkyl)aminocarbonyl;

R$^{15}$ represents $C_{1-6}$alkyl optionally substituted with cyano, aminocarbonyl or mono- or di($C_{1-4}$alkyl)aminocarbonyl;

R$^{16}$ represents $C_{1-6}$alkyl optionally substituted with cyano, aminocarbonyl or mono- or di($C_{1-4}$alkyl)aminocarbonyl; or R$^7$;

—C-D- represents a bivalent radical of formula

—N=CH—NR$^{17}$— (c-1); or

—NR$^{17}$—CH=N— (c-2);

R$^{17}$ represents hydrogen; $C_{1-6}$alkyl optionally substituted with hydroxy, cyano, aminocarbonyl, mono- or di($C_{1-4}$alkyl)aminocarbonyl, $C_{1-4}$alkyloxycarbonyl or aryl;

p represents an integer of value 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, R$^7$ or —X$_3$—R$^7$;

provided that when A represents a radical of formula (a) then B represents a radical of formula (b) and when A represents a radical of formula (b) then B represents a radical of formula (a).

2. A compound according to claim 1 wherein the compound has the formula

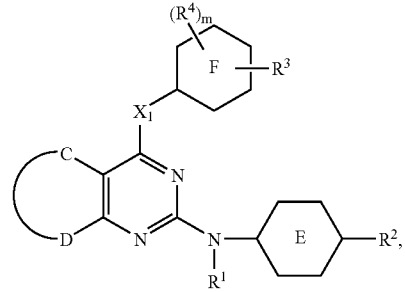
(I-A)

or a pharmaceutically acceptable addition salt, or a stereochemically isomeric form thereof, wherein R$^1$, R$^2$, R$^3$, R$^4$, ring E, ring F, C, D, X$_1$ and m are as defined in claim 1.

3. A compound according to claim 2 wherein the compound of formula (I-A) has the formula

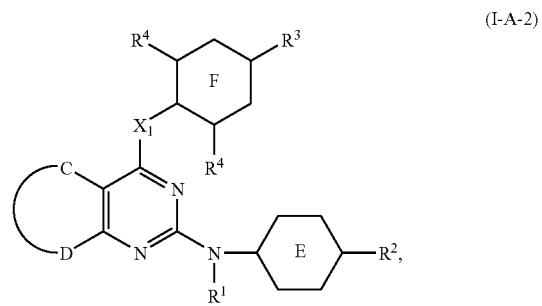
(I-A-2)

or a pharmaceutically acceptable addition salt, or a stereochemically isomeric form thereof, wherein R$^1$, R$^2$, R$^3$, R$^4$, ring E, ring F, C, D and X$_1$ are as defined in claim 2.

4. A compound according to claim 1 wherein the compound has the formula

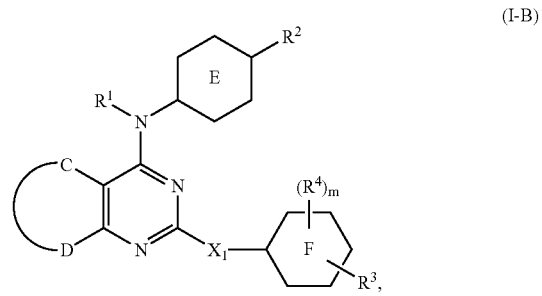
(I-B)

or a pharmaceutically acceptable addition salt or a stereochemically isomeric form thereof, wherein R$^1$, R$^2$, R$^3$, R$^4$, ring E, ring F, C, D, X$_1$ and m are as defined in claim 1.

5. A compound according to claim 4 wherein the compound of formula (I-B) has the formula

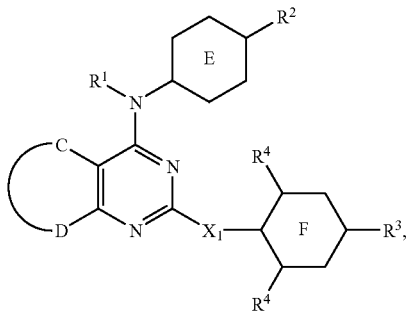

(I-B-2)

or a pharmaceutically acceptable addition salt, or a stereochemically isomeric form thereof,
wherein $R^1$, $R^2$, $R^3$, $R^4$, ring E, ring F, C, D and $X_1$ are as defined in claim 4.

6. A compound according to claim 1 wherein ring E is phenyl.

7. A compound according to claim 1 wherein ring F is phenyl.

8. A compound according to claim 1 wherein the compound has the formula

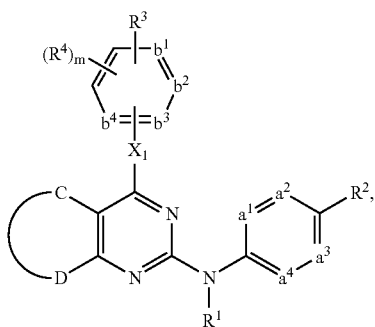

(I')

or a pharmaceutically acceptable addition salt, or a stereochemically isomeric form thereof, wherein
-$a^1$=$a^2$-C($R^2$)=$a^3$-$a^4$=represents a bivalent radical of formula —CH=CH—C($R^2$)=CH—CH=     (a-1);

—N=CH—C($R^2$)=CH—CH=     (a-2);

—CH=N—C($R^2$)=CH—CH=     (a-3);

—N=CH—C($R^2$)=N—CH=     (a-4);

—N=CH—C($R^2$)=CH—N=     (a-5);

—CH=N—C($R^2$)=N—CH=     (a-6); or

—N=N—C($R^2$)=CH—CH=     (a-7);

-$b^1$=$b^2$-$b^3$=$b^4$- represents a bivalent radical of formula

—CH=CH—CH=CH—     (b-1);

—N=CH—CH=CH—     (b-2);

—N=CH—N=CH—     (b-3);

—N=CH—CH=N—     (b-4); or

—N=N—CH=CH—     (b-5);

—C-D- represents a bivalent radical of formula

—N=CH—$NR^{17}$—     (c-1); or

—$NR^{17}$—CH=N—     (c-2);

m represents an integer of value 1, 2, 3 and in case -$b^1$=$b^2$-$b^3$=$b^4$- is (b-1), then m may also be 4;

$R^1$ represents hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;

$R^2$ represents cyano; $C_{1-6}$alkyl substituted with cyano, aminocarbonyl or mono- or di($C_{1-4}$alkyl)aminocarbonyl; $C_{2-6}$alkenyl substituted with cyano, aminocarbonyl or mono- or di($C_{1-4}$alkyl)aminocarbonyl; or $C_{2-6}$alkynyl substituted with cyano, aminocarbonyl or mono- or di($C_{1-4}$alkyl)aminocarbonyl;

$X_1$ represents —$NR^5$—, —NH—NH—, —N=N—, —O—, —C(=O)—, $C_{1-4}$alkanediyl, —CHOH—, —S—, —S(=O)$_p$—, —$X_2$—$C_{1-4}$alkanediyl- or —$C_{1-4}$alkanediyl-$X_2$—;

$X_2$ represents —$NR^5$—, —NH—NH—, —N=N—, —O—, —C(=O)—, —CHOH—, —S—, —S(=O)$_p$—;

$R^3$ represents $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; cyano; halo; $C_{1-6}$alkyl; polyhalo$C_{1-6}$alkyl; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{1-6}$alkyloxy optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl optionally substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl optionally substituted with one or more substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$;

$X_3$ is —$NR^5$—, —NH—NH—, —N=N—, —O—, —C(=O)—, —S—, —S(=O)$_p$—, —$X_{4b}$—$C_{1-4}$alkanediyl-, —$C_{1-4}$alkanediyl-$X_{4a}$—, —$C_{1-4}$alkanediyl-$X_{4b}$—$C_{1-4}$alkanediyl, —C(=N—$OR^8$)—$C_{1-4}$alkanediyl-;

with $X_{4a}$ being —NH—NH—, —N=N—, —O—, —C(=O)—, —S—, —S(=O)$_p$—; and with $X_{4b}$ being —NH—NH—, —N=N—, —C(=O)—, —S—, —S(=O)$_p$—;

each $R^4$ independently represents halo, hydroxy, $C_{1-6}$alkyl, $C_{3-7}$cycloalkyl, $C_{1-6}$alkyloxy, hydroxy$C_{1-6}$alkyl, amino$C_{1-6}$alkyl, cyano, nitro, polyhalo$C_{1-6}$alkyl, polyhalo$C_{1-6}$alkyloxy, aminocarbonyl, mono- or di($C_{1-4}$alkyl)aminocarbonyl, $C_{1-6}$alkyloxycarbonyl, $C_{1-6}$alkylcarbonyl, formyl, amino, mono- or di($C_{1-4}$alkyl)amino or $R^7$;

$R^5$ is hydrogen; aryl; formyl; $C_{1-6}$alkylcarbonyl; $C_{1-6}$alkyloxycarbonyl; $C_{1-6}$alkyl optionally substituted with formyl, $C_{1-6}$alkylcarbonyl, $C_{1-6}$alkyloxycarbonyl or $C_{1-6}$alkylcarbonyloxy; or $C_{1-6}$alkyloxy$C_{1-6}$alkylcarbonyl substituted with $C_{1-6}$alkyloxycarbonyl;

$R^6$ is $C_{1-4}$alkyl, amino, mono- or di($C_{1-4}$alkyl)amino or polyhalo$C_{1-4}$alkyl;

$R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted where possible with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$alkanediyl-;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted where possible with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, or —CH(=N—O—$R^8$);

$R^8$ is hydrogen, $C_{1-4}$alkyl optionally substituted with aryl, or aryl;

$R^9$ and $R^{10}$ each independently are hydrogen; $C_{1-6}$alkyl; $C_{1-6}$alkylcarbonyl; $C_{1-6}$alkyloxycarbonyl; amino; mono- or di($C_{1-4}$alkyl)amino; mono- or di($C_{1-4}$alkyl)aminocarbonyl; —CH(=N$R^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalo$C_{1-4}$alkyl, polyhalo$C_{1-4}$alkyloxy, polyhalo$C_{1-4}$alkylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$, $R^7$; or $R^9$ and $R^{10}$ may be taken together to form a bivalent radical of formula —CH$_2$—CH$_2$—CH$_2$—CH$_2$— (d-1);

—CH$_2$—CH$_2$—CH$_2$—CH$_2$—CH$_2$— (d-2);

—CH$_2$—CH$_2$—O—CH$_2$—CH$_2$— (d-3);

—CH$_2$—CH$_2$—S—CH$_2$—CH$_2$— (d-4);

—CH$_2$—CH$_2$—NR$^{12}$—CH$_2$—CH$_2$— (d-5); or

—CH$_2$—CH=CH—CH$_2$— (d-6);

$R^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ represents hydrogen or $C_{1-4}$alkyl;

$R^{13}$ and $R^{14}$ each independently represent $C_{1-6}$alkyl optionally substituted with cyano, aminocarbonyl or mono- or di($C_{1-4}$alkyl)aminocarbonyl; $C_{2-6}$alkenyl optionally substituted with cyano, aminocarbonyl or mono- or di($C_{1-4}$alkyl)aminocarbonyl;

$C_{2-6}$alkynyl optionally substituted with cyano, aminocarbonyl or mono- or di($C_{1-4}$alkyl)aminocarbonyl;

$R^{15}$ represents $C_{1-6}$alkyl substituted with cyano, aminocarbonyl or mono- or di($C_{1-4}$alkyl)aminocarbonyl;

$R^{16}$ represents $C_{1-6}$alkyl optionally substituted with cyano, aminocarbonyl or mono- or di($C_{1-4}$alkyl)aminocarbonyl; or $R^7$;

$R^{17}$ represents hydrogen; $C_{1-6}$alkyl; or $C_{1-6}$alkyl substituted with aryl;

p is 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$.

9. A compound according to claim 1 wherein $R^2$ represents cyano.

10. A compound according to claim 1 wherein $R^3$ is cyano; aminocarbonyl; $C_{1-6}$alkyl optionally substituted with cyano or aminocarbonyl;

$C_{1-6}$alkyloxy optionally substituted with cyano or aminocarbonyl; $C_{2-6}$alkenyl substituted with cyano or aminocarbonyl.

11. A compound according to claim 1 wherein m is 2; $R^1$ represents hydrogen; $R^2$ represents cyano; $R^3$ represents cyano;

$C_{1-6}$alkyl; $C_{1-6}$alkyl substituted with cyano; $C_{1-6}$alkyloxy optionally substituted with cyano; $C_{2-6}$alkenyl substituted with cyano or —C(=O)—NR$^9$R$^{10}$; each $R^4$ independently represents halo, $C_{1-6}$alkyl or $C_{1-6}$alkyloxy; $X_1$ represents —NR$^5$— or —O—; $R^5$ represents hydrogen; $R^9$ and $R^{10}$ each independently are hydrogen or $C_{1-6}$alkyl; or $R^9$ and $R^{10}$ may be taken together to form a bivalent radical of formula —CH$_2$—CH$_2$—O—CH$_2$—CH$_2$— (d-3); $R^{17}$ is hydrogen; $C_{1-6}$alkyl optionally substituted with hydroxy, cyano, aminocarbonyl, $C_{1-4}$alkyloxycarbonyl or aryl; aryl is phenyl substituted with $C_{1-6}$alkyloxy.

12. A pharmaceutical composition comprising a pharmaceutically acceptable carrier and a therapeutically effective amount of a compound of claim 1.

13. A process for preparing a pharmaceutical composition comprising mixing a therapeutically effective amount of a compound of claim 1 with a pharmaceutically acceptable carrier.

14. A product containing (a) a compound as defined in claim 1, and (b) another antiretroviral compound, as a combined preparation for simultaneous, separate or sequential use in the treatment of HIV infection.

15. A pharmaceutical composition comprising a pharmaceutically acceptable carrier and as active ingredients (a) a compound as defined in claim 1, and (b) another antiretroviral compound.

16. A compound selected from the group consisting of:
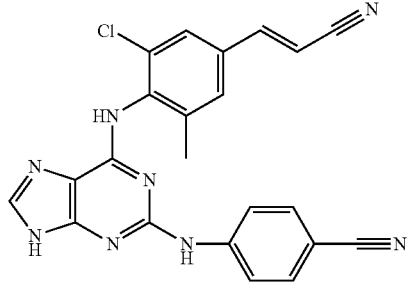 (E)
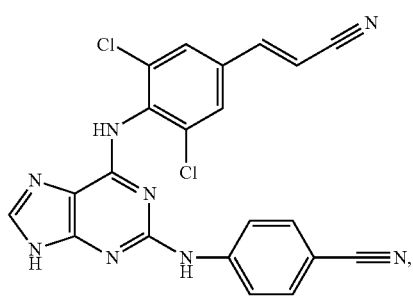 (E)
and pharmaceutically acceptable addition salts thereof.
17. A compound selected from the group consisting of:
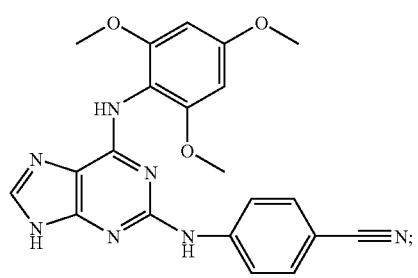
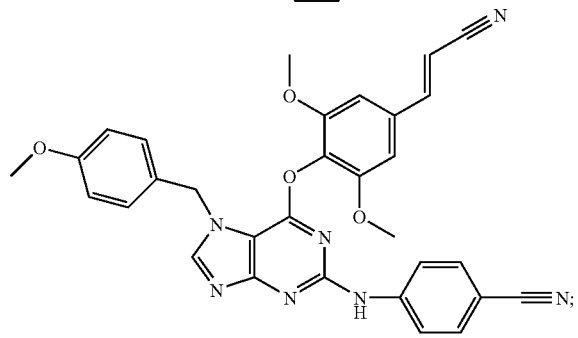
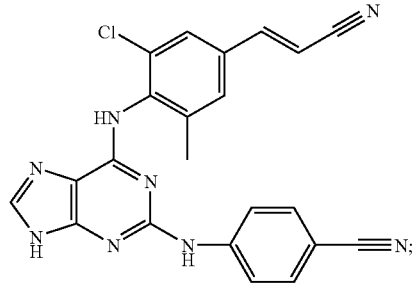
-continued
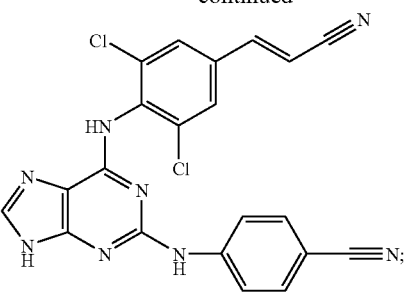
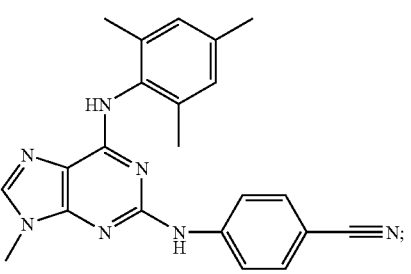
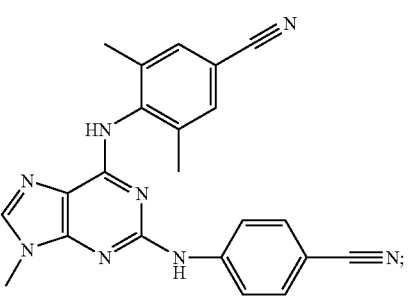
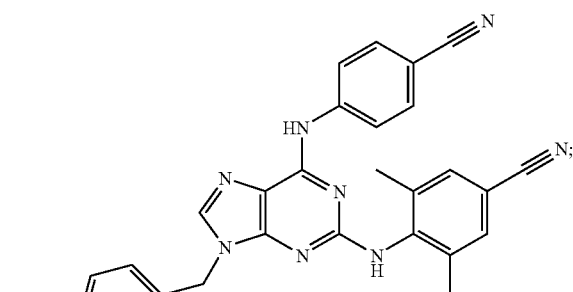
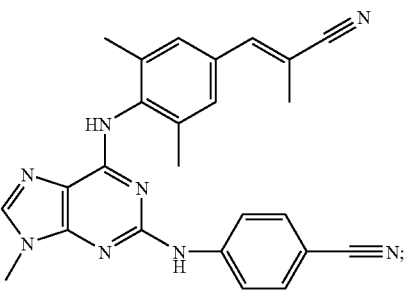

99
-continued
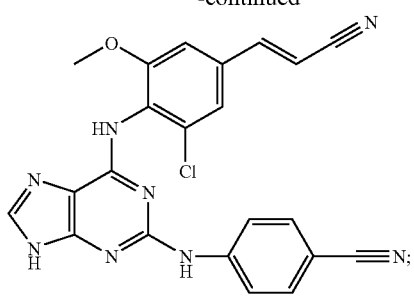
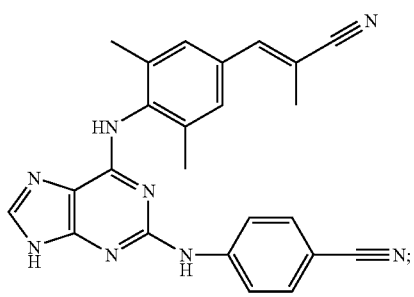
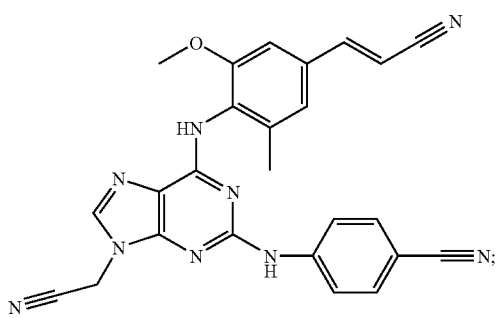
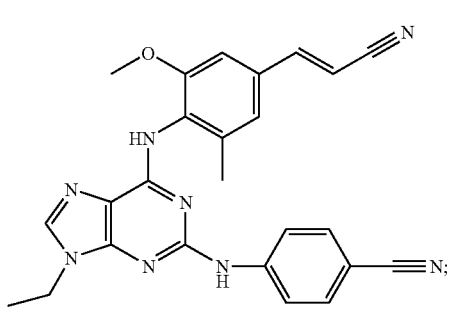
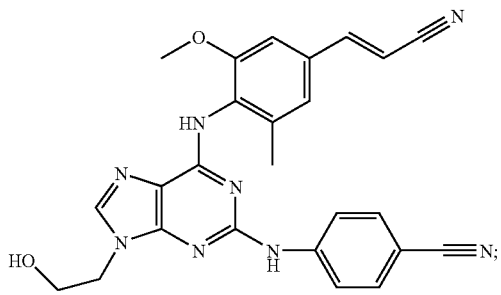
100
-continued
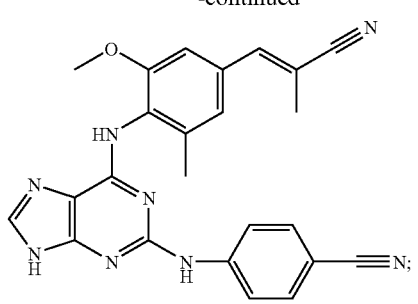
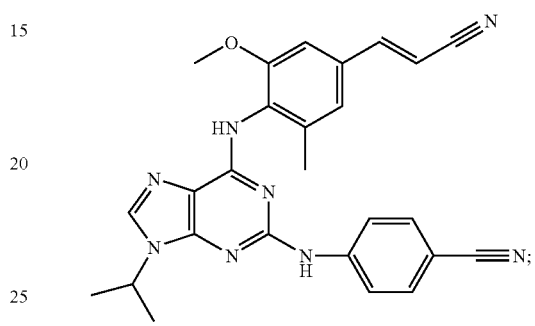
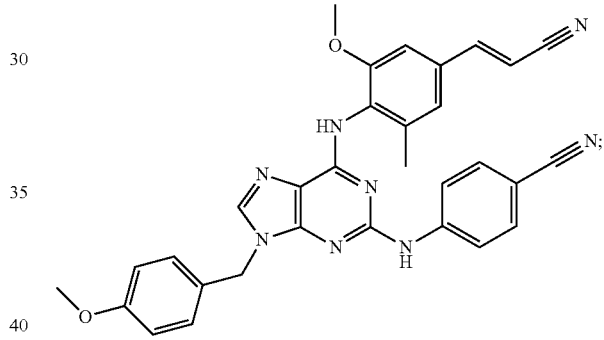
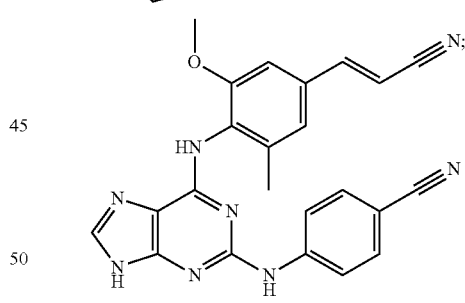
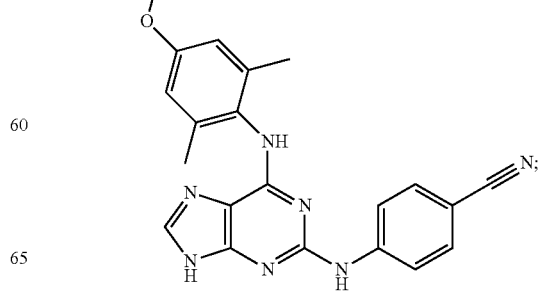

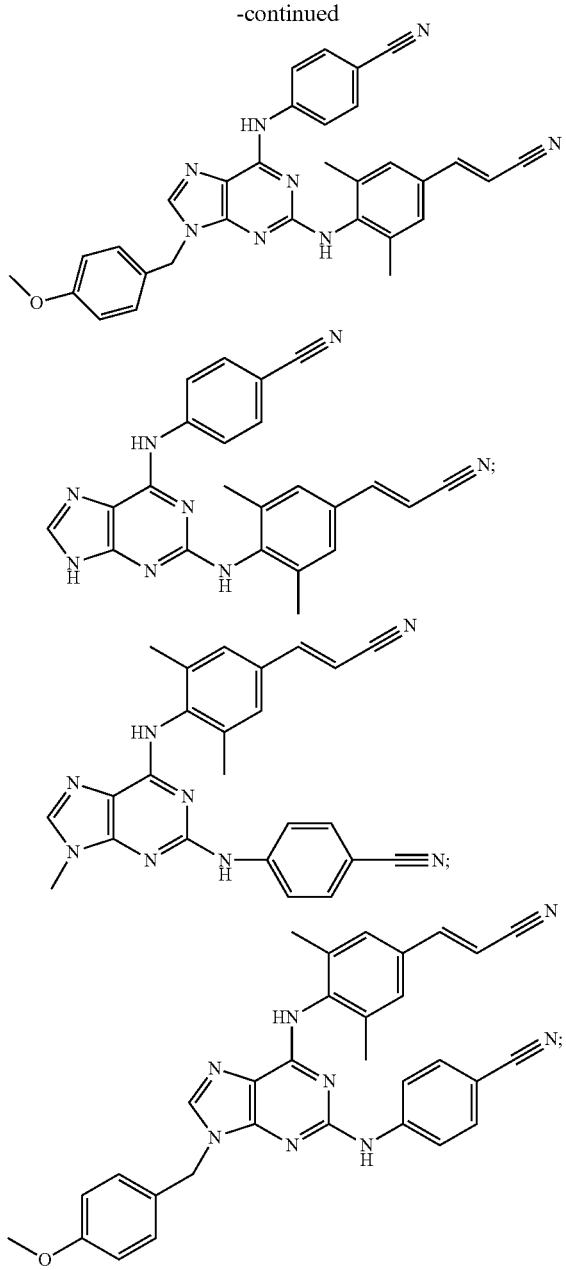

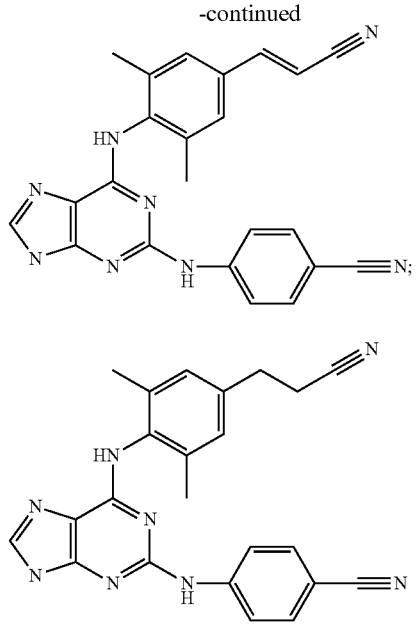

or a pharmaceutically acceptable addition salt thereof.

18. A product containing (a) a compound as defined in claim 17, and (b) another antiretroviral compound, as a combined preparation for simultaneous, separate or sequential use in the treatment of HIV infection.

19. A pharmaceutical composition comprising a pharmaceutically acceptable carrier and as active ingredients (a) a compound as defined in claim 17 and (b) another antiretroviral compound.

20. A pharmaceutical composition comprising a pharmaceutically acceptable carrier and as active ingredient a therapeutically effective amount of a compound as claimed in claim 17.

21. A process for preparing a pharmaceutical composition comprising mixing a therapeutically effective amount of a compound as claimed in claim 17 with a pharmaceutically acceptable carrier.

* * * * *